(12) United States Patent
Chang et al.

(10) Patent No.: US 7,462,323 B1
(45) Date of Patent: *Dec. 9, 2008

(54) APPARATUS FOR PERFORMING HEAT-EXCHANGING CHEMICAL REACTIONS

(75) Inventors: Ronald Chang, Redwood City, CA (US); Douglas B. Dority, Mill Valley, CA (US); Lee A. Christel, Palo Alto, CA (US); Robert Yuan, Belmont, CA (US); Kurt E. Petersen, San Jose, CA (US)

(73) Assignee: Cepheid, Sunnyvale, CA (US)

( * ) Notice: Subject to any disclaimer, the term of this patent is extended or adjusted under 35 U.S.C. 154(b) by 1007 days.

This patent is subject to a terminal disclaimer.

(21) Appl. No.: 10/719,073

(22) Filed: Nov. 21, 2003

Related U.S. Application Data

(60) Division of application No. 09/468,690, filed on Dec. 21, 1999, now Pat. No. 6,660,228, which is a continuation-in-part of application No. 09/194,374, filed on Jul. 25, 2000.

(51) Int. Cl.
   *G01N 15/06* (2006.01)
   *G01N 21/00* (2006.01)
   *G01N 33/00* (2006.01)
   *G01N 1/10* (2006.01)
   *B01L 3/02* (2006.01)

(52) U.S. Cl. .............. 422/68.1; 422/100; 422/102; 422/58; 436/180; 436/172

(58) Field of Classification Search ............... 422/68.1, 422/58, 100, 102, 63, 82.05, 82.12; 436/180, 436/172

See application file for complete search history.

(56) References Cited

U.S. PATENT DOCUMENTS

| | | | |
|---|---|---|---|
| 3,607,098 | A | 9/1971 | Strande |
| 3,708,886 | A | 1/1973 | Ogle |
| 4,154,690 | A | 5/1979 | Ballies |
| 4,192,429 | A | 3/1980 | Yerman |
| 4,479,578 | A | 10/1984 | Brignola et al. |
| 4,810,653 | A | 3/1989 | Helfer et al. |
| 4,902,624 | A | 2/1990 | Columbus et al. |

(Continued)

FOREIGN PATENT DOCUMENTS

EP 0 318 255 5/1989

(Continued)

OTHER PUBLICATIONS

Wittwer, et al. (1997). "The LightCycler.TM.: A Microvolume Multisample Fluorimeter with Rapid Temperature Control," *BioTechniques* 22:176-181.

*Primary Examiner*—Brian R. Gordon
(74) *Attorney, Agent, or Firm*—Townsend and Townsend and Crew LLP

(57) ABSTRACT

An apparatus for controlling the temperature of a reaction mixture contained in a chamber of a reaction vessel comprises a thermal surface for contacting a flexible wall of the chamber and an automated machine for increasing the pressure in the chamber. The pressure increase in the chamber is sufficient to force the flexible wall to conform to the thermal surface for good thermal conductance. The apparatus also includes at least one thermal element for heating or cooling the surface to induce a temperature change within the chamber.

52 Claims, 37 Drawing Sheets

U.S. PATENT DOCUMENTS

| | | | |
|---|---|---|---|
| 5,038,852 A | 8/1991 | Johnson et al. | |
| 5,333,675 A | 8/1994 | Mullis et al. | |
| 5,376,313 A | 12/1994 | Kanewske, III et al. | |
| 5,443,791 A * | 8/1995 | Cathcart et al. | 422/65 |
| 5,460,780 A | 10/1995 | Devaney, Jr. et al. | |
| 5,589,136 A | 12/1996 | Northrup et al. | |
| 5,656,493 A | 8/1997 | Mullis et al. | |
| 5,721,136 A | 2/1998 | Finney et al. | |
| 5,783,148 A | 7/1998 | Cottingham et al. | |
| 5,786,182 A | 7/1998 | Catanzariti et al. | |
| 5,811,296 A | 9/1998 | Chemelli et al. | |
| 5,882,601 A * | 3/1999 | Kath et al. | 422/102 |
| 5,928,907 A | 7/1999 | Woudenberg et al. | |
| 5,945,070 A * | 8/1999 | Kath et al. | 422/101 |
| 5,958,349 A | 9/1999 | Petersen et al. | |
| 6,144,448 A | 11/2000 | Mitoma | |
| 6,325,114 B1 * | 12/2001 | Bevirt et al. | 141/130 |
| 6,447,728 B1 * | 9/2002 | Wilmes et al. | 422/100 |
| 6,509,193 B1 * | 1/2003 | Tajima | 436/49 |
| 7,115,234 B2 * | 10/2006 | Freitag et al. | 422/130 |

FOREIGN PATENT DOCUMENTS

| | | |
|---|---|---|
| EP | 0 436 995 A2 | 7/1991 |
| EP | 0 545 736 A2 | 6/1993 |
| EP | 0 603 411 A1 | 6/1994 |
| EP | 0 606 961 A1 | 7/1994 |
| EP | 0 662 345 A1 | 7/1995 |
| EP | 0 693 560 A2 | 1/1996 |
| EP | 1 045 038 | 10/2000 |
| WO | WO 98/38487 | 9/1998 |
| WO | WO 99/33559 | 7/1999 |
| WO | WO 99/48608 | 9/1999 |
| WO | WO 99/60380 | 11/1999 |

* cited by examiner

APPARATUS FOR PERFORMING HEAT-EXCHANGING CHEMICAL REACTIONS

RELATED APPLICATION INFORMATION

This application is a divisional of U.S. patent application Ser. No. 09/468,690, filed Dec. 21, 1999, which is a continuation in part of U.S. application Ser. No. 09/194,374, filed Jul. 25, 2000, now U.S. Pat. No. 6,565,815, filed as a national phase stage entry (371) of international application PCT/US98/03962, filed Mar. 2, 1998. All of these applications are incorporated by reference herein for all purposes.

FIELD OF THE INVENTION

The present invention relates to an apparatus for performing heat-exchanging, chemical reactions and for optically detecting a reaction product.

BACKGROUND OF THE INVENTION

There are many applications in the field of chemical processing in which it is desirable to precisely control the temperature of reaction mixtures (e.g., biological samples mixed with chemicals or reagents), to induce rapid temperature changes in the mixtures, and to detect target analytes in the mixtures. Applications for such heat-exchanging chemical reactions may encompass organic, inorganic, biochemical and molecular reactions, and the like. Examples of thermal chemical reactions include isothermal nucleic acid amplification, thermal cycling nucleic acid amplification, such as the polymerase chain reaction (PCR), ligase chain reaction (LCR), self-sustained sequence replication, enzyme kinetic studies, homogeneous ligand binding assays, and more complex biochemical mechanistic studies that require complex temperature changes. Temperature control systems also enable the study of certain physiologic processes where a constant and accurate temperature is required.

One of the most popular uses of temperature control systems is for the performance of PCR to amplify a segment of nucleic acid. In this well known methodology, a DNA template is used with a thermostable DNA polymerase, nucleoside triphosphates, and two oligonucleotides with different sequences, complementary to sequences that lie on opposite strands of the template DNA and which flank the segment of DNA that is to be amplified ("primers"). The reaction components are cycled between a first temperature (e.g., 95° C.) for denaturing double stranded template DNA, followed by a second temperature (e.g., 40-60° C.) for annealing of primers, and a third temperature (e.g., 70-75° C.) for polymerization. For some newer assays, the annealing and polymerization may be performed at the same temperature (e.g. 55-60° C.), so that only two set point temperatures are required in each thermal cycle. Repeated cycling provides exponential amplification of the template DNA.

Nucleic acid amplification may be applied to the diagnosis of genetic disorders; the detection of nucleic acid sequences of pathogenic organisms in a variety of samples including blood, tissue, environmental, air borne, and the like; the genetic identification of a variety of samples including forensic, agricultural, veterinarian, and the like; the analysis of mutations in activated oncogenes, detection of contaminants in samples such as food; and in many other aspects of molecular biology. Polynucleotide amplification assays can be used in a wide range of applications such as the generation of specific sequences of cloned double-stranded DNA for use as probes, the generation of probes specific for uncloned genes by selective amplification of particular segments of cDNA, the generation of libraries of cDNA from small amounts of mRNA, the generation of large amounts of DNA for sequencing and the analysis of mutations.

A preferred detection technique for chemical or biochemical analysis is optical interrogation, typically using fluorescence or chemiluminescence measurements. For ligand-binding assays, time-resolved fluorescence, fluorescence polarization, or optical absorption is often used. For PCR assays, fluorescence chemistries are often employed.

Conventional instruments for conducting thermal reactions and for optically detecting the reaction products typically incorporate a block of metal having as many as ninety-six conical reaction tubes. The metal block is heated and cooled either by a Peltier heating/cooling apparatus or by a closed-loop liquid heating/cooling system in which liquid flows through channels machined into the block. Such instruments incorporating a metal block are described in U.S. Pat. No. 5,038,852 to Johnson and U.S. Pat. No. 5,333,675 to Mullis.

These conventional instruments have several disadvantages. First, due to the large thermal mass of a metal block, the heating and cooling rates in these instruments are limited to about 1° C./sec resulting in longer processing times. For example, in a typical PCR application, fifty cycles may require two or more hours to complete. With these relatively slow heating and cooling rates, some processes requiring precise temperature control are inefficient. For example, reactions may occur at the intermediate temperatures, creating unwanted and interfering side products, such as PCR "primer-dimers" or anomalous amplicons, which are detrimental to the analytical process. Poor control of temperature also results in over-consumption of expensive reagents necessary for the intended reaction.

A second disadvantage of these conventional instruments is that they typically do not permit real-time optical detection or continuous optical monitoring of the chemical reaction. For example, in conventional thermal cycling instruments, optical fluorescence detection is typically accomplished by guiding an optical fiber to each of ninety-six reaction sites in a metal block. A central high power laser sequentially excites each reaction site and captures the fluorescence signal through the optical fiber. Since all of the reaction sites are sequentially excited by a single laser and since the fluorescence is detected by a single spectrometer and photomultiplier tube, simultaneous monitoring of each reaction site is not possible.

Some of the instrumentation for newer processes requiring faster thermal cycling times has recently become available. One such device is disclosed by Northrup et al. in U.S. Pat. No. 5,589,136. The device includes a silicon-based, sleeve-type reaction chamber that combines heaters, such as doped polysilicon for heating, and bulk silicon for convection cooling. The device optionally includes a secondary tube (e.g., plastic) for holding the sample. In operation, the tube containing the sample is inserted into the silicon sleeve. Each sleeve also has its own associated optical excitation source and fluorescence detector for obtaining real-time optical data. This device permits faster heating and cooling rates than the instruments incorporating a metal block described above. There are, however, several disadvantages to this device in its use of a micromachined silicon sleeve. A first disadvantage is that the brittle silicon sleeve may crack and chip. A second disadvantage is that it is difficult to micromachine the silicon sleeve with sufficient accuracy and precision to allow the sleeve to precisely accept a plastic tube that holds the sample.

Consequently, the plastic tube may not establish optimal thermal contact with the silicon sleeve.

Another instrument is described by Wittwer et al. in *"The LightCycler™. A Microvolume Multisample Fluorimeter with Rapid Temperature Control"*, BioTechniques, Vol. 22, pgs. 176-181, January 1997. The instrument includes a circular carousel for holding up to thirty-two samples. The temperature of the samples is controlled by a central heating cartridge and a fan positioned in a central chamber of the carousel. In operation, the samples are placed in capillaries which are held by the carousel, and a stepper motor rotates the carousel to sequentially position each of the samples over an optics assembly. Each sample is optically interrogated through a capillary tip by epi-illumination. This instrument also permits faster heating and cooling rates than the metal blocks described above. Unfortunately, this instrument is not easily configured for commercial, high throughput diagnostic applications.

SUMMARY

The present invention overcomes the disadvantages of the prior art by providing an improved apparatus for thermally controlling and optically interrogating a reaction mixture. In contrast to the prior art instruments described above, the apparatus of the present invention permits extremely rapid heating and cooling of the mixture, ensures optimal thermal transfer between the mixture and heating or cooling elements, provides real-time optical detection and monitoring of reaction products with increased detection sensitivity, and is easily configured for automated, high throughput applications. The apparatus is useful for performing heat-exchanging chemical reactions, such as nucleic acid amplification.

In a preferred embodiment, the apparatus includes a reaction vessel having a chamber for holding the mixture. The vessel has a rigid frame defining the side walls of the chamber, and at least one flexible sheet attached to the rigid frame to form a major wall of the chamber. The rigid frame further includes a port and a channel connecting the port to the chamber to permit easy filling, sealing, and pressurization of the chamber. The apparatus also includes at least one thermal surface for contacting the flexible major wall of the chamber. The apparatus further includes a device for increasing the pressure in the chamber. The pressure increase in the chamber is sufficient to force the flexible major wall to contact and conform to the thermal surface, thus ensuring optimal thermal conductance between the thermal surface and the chamber. The apparatus also includes one or more thermal elements (e.g., a heating element, thermoelectric device, heat sink, fan, or peltier device) for heating or cooling the thermal surface to induce a temperature change within the chamber.

In the preferred embodiment, the reaction vessel includes first and second flexible sheets attached to opposite sides of the rigid frame to form opposing major walls of the chamber. In this embodiment, the apparatus includes first and second thermal surfaces formed by first and second opposing plates positioned to receive the chamber of the vessel between. When the pressure in the chamber is increased, the flexible major walls expand outwardly to contact and conform to the inner surfaces of the plates. A resistive heating element, such as a thick or thin film resistor, is coupled to each plate for heating the plates. In addition, the apparatus includes a cooling device, such as a fan, for cooling the plates. Each of the plates is preferably constructed of a ceramic material and has a thickness less than or equal to 1 mm for low thermal mass. In particular, it is presently preferred that each of the plates have a thermal mass less than about 5 J/° C., more preferably less than 3 J/° C., and most preferably less than 1 J/° C. to enable extremely rapid heating and cooling rates.

The apparatus also preferably includes a support structure for holding the plates in an opposing relationship to each other. In the preferred embodiment, the support structure comprises a mounting plate having a slot therein, and spacing posts extending from the mounting plate on opposite sides of the slot. Each of the spacing posts has indentations formed on opposite sides thereof for receiving the edges of the plates. Retention clips hold the edges of the plates in the indentations formed in the spacing posts. The slot in the mounting plate enables insertion of the vessel between the plates.

The pressurization of the chamber ensures that the flexible major walls of the vessel are forced to conform to the inner surfaces of the plates, thus guaranteeing optimal thermal contact between the major walls and the plates. In the preferred embodiment, the device for increasing pressure in the chamber comprises a plunger which is inserted into the channel to compress gas in the vessel and thereby increase pressure in the chamber. The plunger preferably has a pressure stroke in the channel sufficient to increase pressure in the chamber to at least 2 psi of above the ambient pressure external to the vessel, and more preferably to a pressure in the range of 8 to 15 psi above the ambient pressure. In a preferred embodiment, the length of the pressure stroke is controlled by one or more pressure control grooves formed in the inner surface of the frame that defines the channel. The pressure control grooves extend from the port to a predetermined depth in the channel to allow gas to escape from the channel and thereby prevent pressurization of the chamber until the plunger reaches the predetermined depth. When the plunger reaches the predetermined depth, it establishes a seal with the walls of the channel and begins the pressure stroke. The pressure control grooves provide for highly controllable pressurization of the chamber and help prevent misalignment of the plunger in the channel.

The reaction vessel may be filled and pressurized manually by a human operator, or alternatively, the apparatus may include an automated machine for filling and pressurizing the vessel. In the automated embodiment, the apparatus preferably includes a pick-and-place machine having a pipette for filling the vessel and having a machine tip for inserting the plunger into the channel after filling. The plunger preferably includes a cap having a tapered engagement aperture for receiving and establishing a fit with the machine tip, thereby enabling the machine tip to pick and place the plunger into the channel.

In another embodiment of the invention, the pressurization of vessel is performed by a pick-and-place machine having a machine head for addressing the vessel. The machine head has an axial bore for communicating with the channel. The pick-and-place machine also includes a pressure source in fluid communication with the bore for pressurizing the chamber of the vessel through the bore. In this embodiment, the apparatus also preferably includes a disposable adapter for placing the bore in fluid communication with the channel. The adapter is sized to be inserted into the channel such that the adapter establishes a seal with the walls of the channel. The disposable adapter preferably includes a valve (e.g., a check valve) for preventing fluid from escaping from the vessel.

In another embodiment of the invention, the device for increasing pressure in the chamber comprises an elastomeric plug which is inserted into the channel, and a needle inserted through the plug for injecting fluid into the vessel. The needle may be used to inject the reaction mixture into the chamber, followed by air or another suitable gas to increase pressure in the chamber. The reaction vessel may be filled and pressurized in this manner by a human operator, or alternatively, the apparatus may include an automated machine for filling and pressurizing the chamber. In the automated embodiment, the apparatus includes a machine for inserting the needle through the plug, and the machine includes a pressure source for injecting fluid into the vessel through the needle.

In another embodiment of the invention, the device for pressurizing the chamber comprises a platen for heat sealing a film or foil to the vessel. The foil is preferably sealed to the portion of the frame defining the port. Heat sealing the film or foil to the vessel seals the port and collapses an end of the channel to reduce the volume of the vessel and thereby increase pressure in the chamber. The reaction vessel may be heat sealed in this manner by a human operator, or alternatively, the apparatus may include an automated machine, e.g. a press, for sealing the vessel.

The apparatus of the present invention permits real-time monitoring and detection of reaction products in the vessel with improved optical sensitivity. In the preferred embodiment, at least two of the side walls of the chamber are optically transmissive and angularly offset from each other, preferably by an angle of about 90°. The apparatus further comprises an optics system for optically interrogating the mixture contained in the chamber through the optically transmissive side walls. The optics system includes at least one light source for exciting the mixture through a first one of the side walls, and at least one detector for detecting light emitted from the chamber through a second one of the side walls.

Optimum optical sensitivity may be attained by maximizing the optical sampling path length of both the light beams exciting the labeled analytes in the reaction mixture and the emitted light that is detected. The thin, wide reaction vessel of the present invention optimizes detection sensitivity by providing maximum optical path length per unit analyte volume. In particular, the vessel is preferably constructed such that the ratio of the width of the chamber to the thickness of the chamber is at least 4:1, and such that the chamber has a thickness in the range of 0.5 to 2 mm. These parameters are presently preferred to provide a vessel having a relatively large average optical path length through the chamber, while still keeping the chamber sufficiently thin to allow for extremely rapid heating and cooling of the reaction mixture.

The apparatus of the present invention may be configured as a small hand-held instrument, or alternatively, as a large instrument with multiple reaction sites for simultaneously processing hundreds of samples. In high throughput embodiments, the plates, heating and cooling elements, and optics are preferably disposed in a single housing to form an independently controllable, heat-exchanging module with detection capability. The apparatus includes a base instrument for receiving a plurality of such modules, and the base instrument includes processing electronics for independently controlling the operation of each module. Each module provides a reaction site for thermally processing a sample contained in a reaction vessel and for detecting one or more target analytes in the sample. The apparatus may also include a computer for controlling the base instrument.

DETAILED DESCRIPTION

The present invention provides an apparatus for thermally controlling and optically interrogating a reaction mixture, e.g., a sample mixed with one or more chemicals or reagents. The sample may also be mixed with diluents or buffers. The sample may be an aqueous solution containing particles, cells, microorganisms, ions, or small and large molecules, such as proteins and nucleic acids, etc. In a particular use, the sample may be a bodily fluid (e.g., blood, urine, saliva, sputum, seminal fluid, spinal fluid, mucus, or other bodily fluids). Alternatively, the sample may be a solid made soluble in a liquid or the sample may be an environmental sample such as ground or waste water, soil extracts, pesticide residues, or airborne spores placed in a liquid.

In a preferred embodiment, the apparatus includes a reaction vessel for holding the mixture and a heat-exchanging module into which the vessel is inserted for thermal processing and optical detection. The heat-exchanging module includes a pair of opposing plates between which the vessel is inserted for thermal processing, one or more heating or cooling elements for heating or cooling the plates, and optics for optically interrogating the reaction mixture contained in the vessel. The apparatus also includes a base unit with processing electronics for receiving a plurality of such heat-exchanging modules and for independently controlling each module. The apparatus may also include a controller, such as a personal computer or network computer, that provides a user interface to the apparatus and controls the operation of the base unit. The apparatus is useful for performing heat-exchanging chemical reactions, such as nucleic acid amplification, and for optically detecting target analytes.

Figure 1:
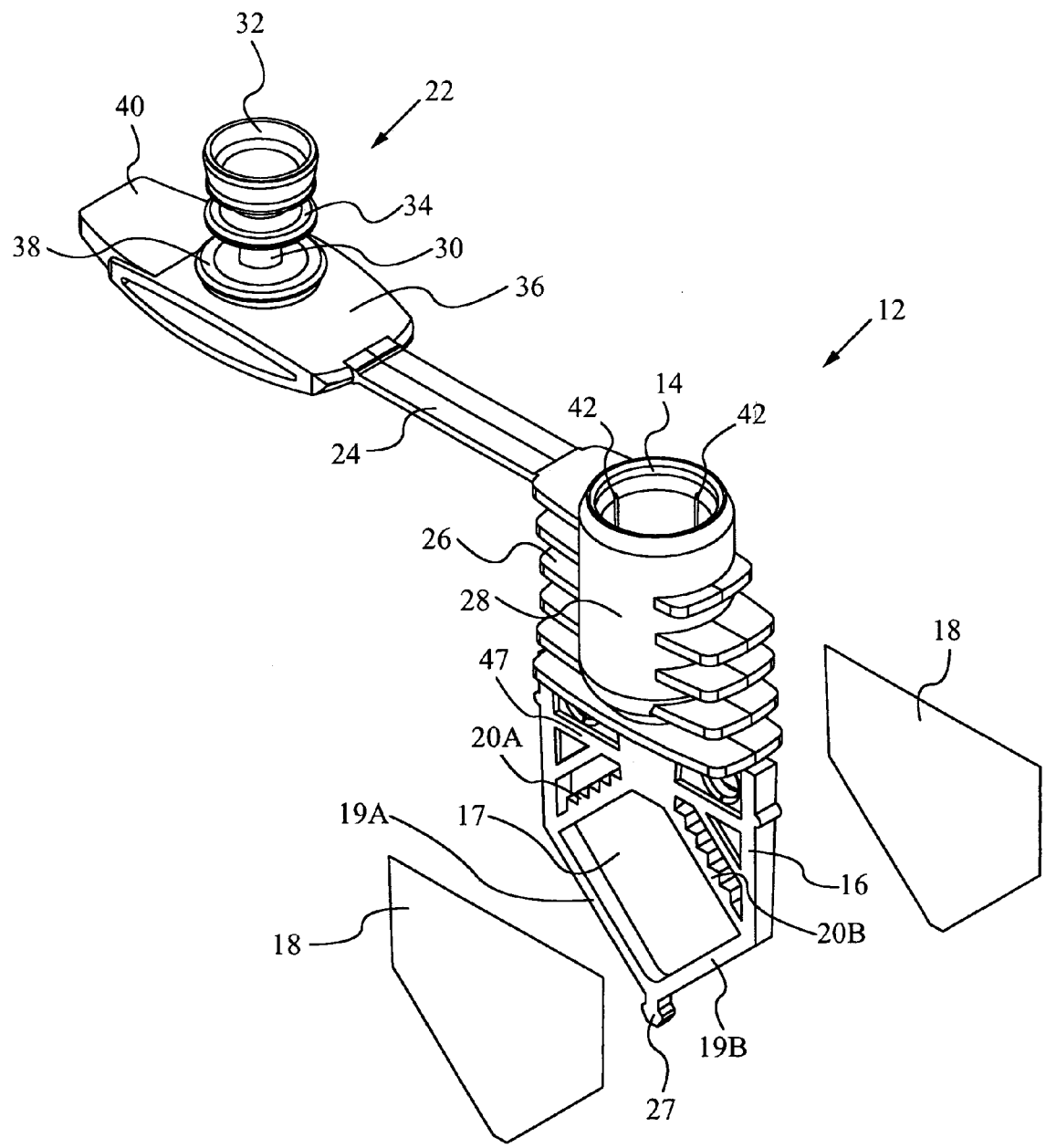
FIG. 1 is a partially exploded, isometric view of a reaction vessel according to a first embodiment of the present invention in which the major walls of the reaction chamber are removed to show the interior of the chamber.
Figure 2:
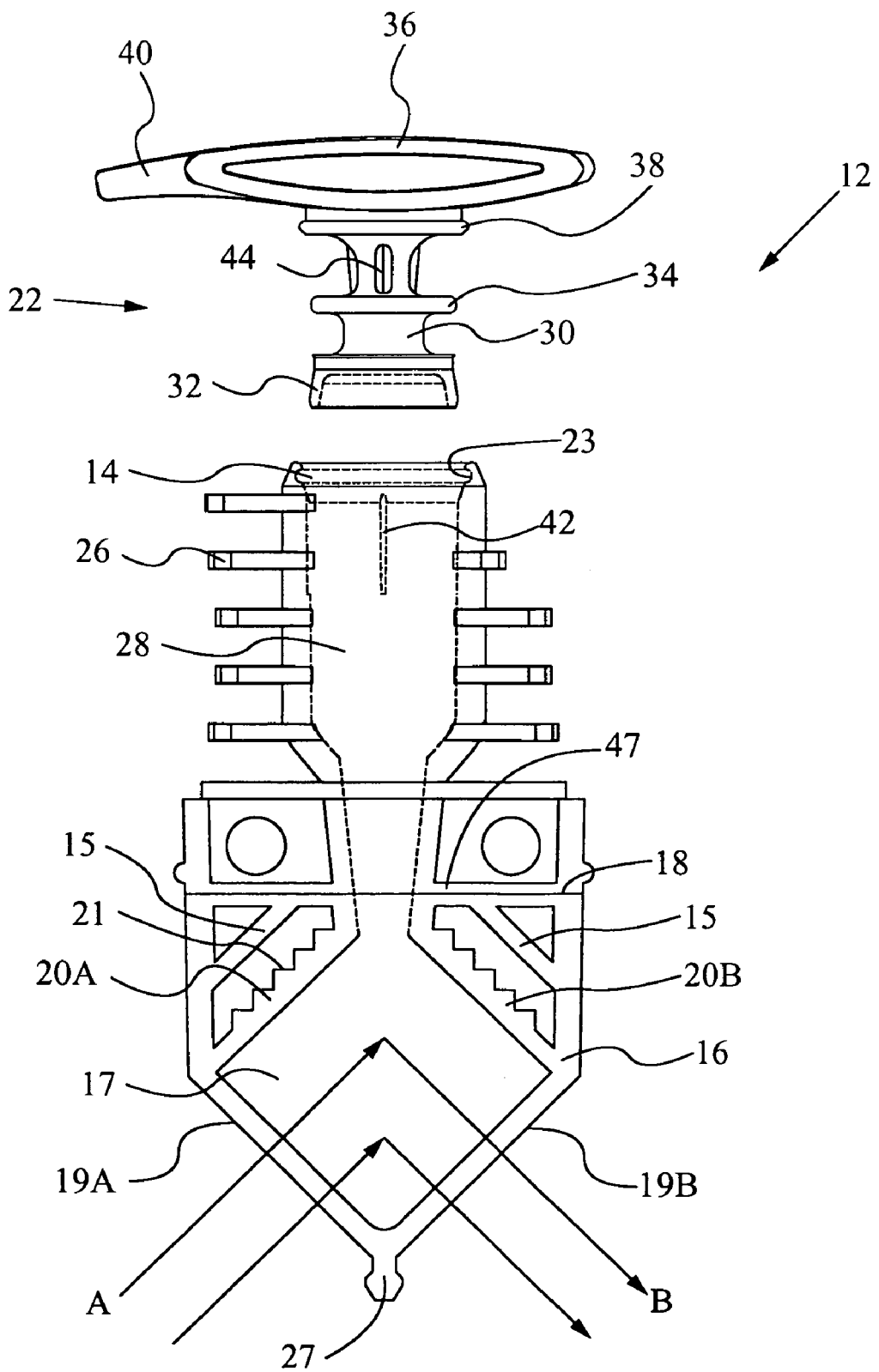
FIG. 2 is a front view of the vessel of FIG. 1.

FIGS. 1-25 illustrate a preferred embodiment of the invention. FIG. 1 shows a partially exploded view of a reaction vessel 12 according to the preferred embodiment, and FIG. 2 shows a front view of the vessel 12. The vessel 12 includes a reaction chamber 17 for holding a reaction mixture for thermal processing and optical interrogation. The vessel 12 is designed for optimal heat transfer to and from the mixture and for efficient optical viewing of the mixture. The thin shape of the vessel contributes to optimal thermal kinetics by providing large surfaces for thermal conduction. In addition, the side walls of the vessel 12 provide optical windows into the chamber 17 so that the entire reaction mixture can be optically interrogated in real-time as the chemical reaction occurs.

In more detail to FIGS. 1-2, the reaction vessel 12 includes a rigid frame 16 that defines the side walls 19A, 19B, 20A, 20B of the reaction chamber 17. The rigid frame 16 also includes a port 14 and a channel 28 that connects the port 14 to the chamber 17. The vessel also includes thin, flexible sheets attached to opposite sides of the rigid frame 16 to form opposing major walls 18 of the chamber. (The major walls 18 are shown in FIG. 1 exploded from the rigid frame 16 for illustrative clarity). The reaction chamber 17 is thus defined by the rigid side walls 19A, 19B, 20A, 20B of the frame 16 and by the flexible major walls 18 which are sealed to opposite sides of the frame.

The major walls 18 facilitate optimal thermal conductance to the reaction mixture contained in the chamber 17. Each of the walls 18 is sufficiently flexible to contact and conform to a respective thermal surface, thus providing for optimal thermal contact and heat transfer between the thermal surface and the reaction mixture contained in the chamber 17. Furthermore, the flexible walls 18 continue to conform to the thermal surfaces if the shape of the surfaces changes due to thermal expansion or contraction during the course of the heat-exchanging operation.

Figure 5:
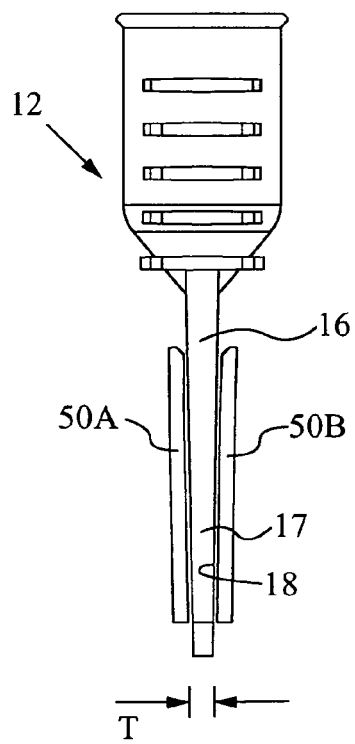
FIG. 5 is a side view of the vessel of FIG. 1 inserted into a thermal sleeve formed by opposing plates.

As shown in FIG. 5, the thermal surfaces for contacting the flexible walls 18 are preferably formed by a pair of opposing plates 50A, 50B positioned to receive the chamber 17 between them. When the chamber 17 of the vessel is inserted between the plates 50A, 50B, the inner surfaces of the plates contact the walls 18 and the flexible walls conform to the surfaces of the plates. The plates are preferably spaced a distance from each other equal to the thickness T of the chamber 17 as defined by the thickness of the frame 16. In this position, minimal or no gaps are found between the plate surfaces and the walls 18. The plates may be heated and cooled by various thermal elements to induce temperature changes within the chamber 17, as is described in greater detail below.

The walls 18 are preferably flexible films of polymeric material such as polypropylene, polyethylene, polyester, or other polymers. The films may either be layered, e.g., laminates, or the films may be homogeneous. Layered films are preferred because they generally have better strength and structural integrity than homogeneous films. In particular, layered polypropylene films are presently preferred because polypropylene is not inhibitory to PCR. Alternatively, the walls 18 may comprise any other material that may be formed into a thin, flexible sheet and that permits rapid heat transfer. For good thermal conductance, the thickness of each wall 18 is preferably between about 0.003 to 0.5 mm, more preferably between 0.01 to 0.15 mm, and most preferably between 0.025 to 0.08 mm.

Referring again to FIGS. 1-2, the reaction vessel 12 also includes a plunger 22 that is inserted into the channel 28 after filling the chamber 17 with the reaction mixture. The plunger 22 compresses gas in the vessel 12 thereby increasing pressure in the chamber 17 and outwardly expanding the flexible walls 18. The gas compressed by the plunger 22 is typically air filling the channel 28. The pressurization of the chamber 17 is important because it forces the walls 18 against the surfaces of the plates 50A, 50B (see FIG. 5) and ensures that the walls 18 fully contact and conform to the inner surfaces of the plates, thus guaranteeing optimal thermal conductance between the plates 50A, 50B and the chamber 17.

Referring again to FIGS. 1-2, the plunger may comprise any device capable of establishing a seal with the walls of the channel 28 and of compressing gas in the vessel. Such devices include, but are not limited to, pistons, plugs, or stoppers. The plunger 22 of the preferred embodiment includes a stem 30 and a piston 32 on the stem. When the plunger 22 is inserted into the channel 28, the piston 32 establishes a seal with the inner walls of the channel and compresses air in the channel.

The piston 32 is preferably a cup integrally formed (e.g., molded) with the stem 30. Alternatively, the piston 32 may be a separate elastomeric piece attached to the stem.

The plunger 22 also preferably includes an alignment ring 34 encircling the stem for maintaining the plunger 22 in coaxial alignment with the channel 28 as the plunger is inserted into the channel. The alignment ring 34 is preferably integrally formed (e.g., molded) with the stem 30. The stem 30 may optionally includes support ribs 44 for stiffening and strengthening the stem. The plunger 22 also includes a plunger cap 36 attached to the stem 30. As shown in FIG. 2, the cap 36 includes a snap ring 38 and the vessel includes an annular recess 23 encircling the port 14 for receiving the snap ring 38.

The cap 36 may optionally include a lever portion 40 which is lifted to remove the plunger 22 from the channel 28.

Figure 7A:
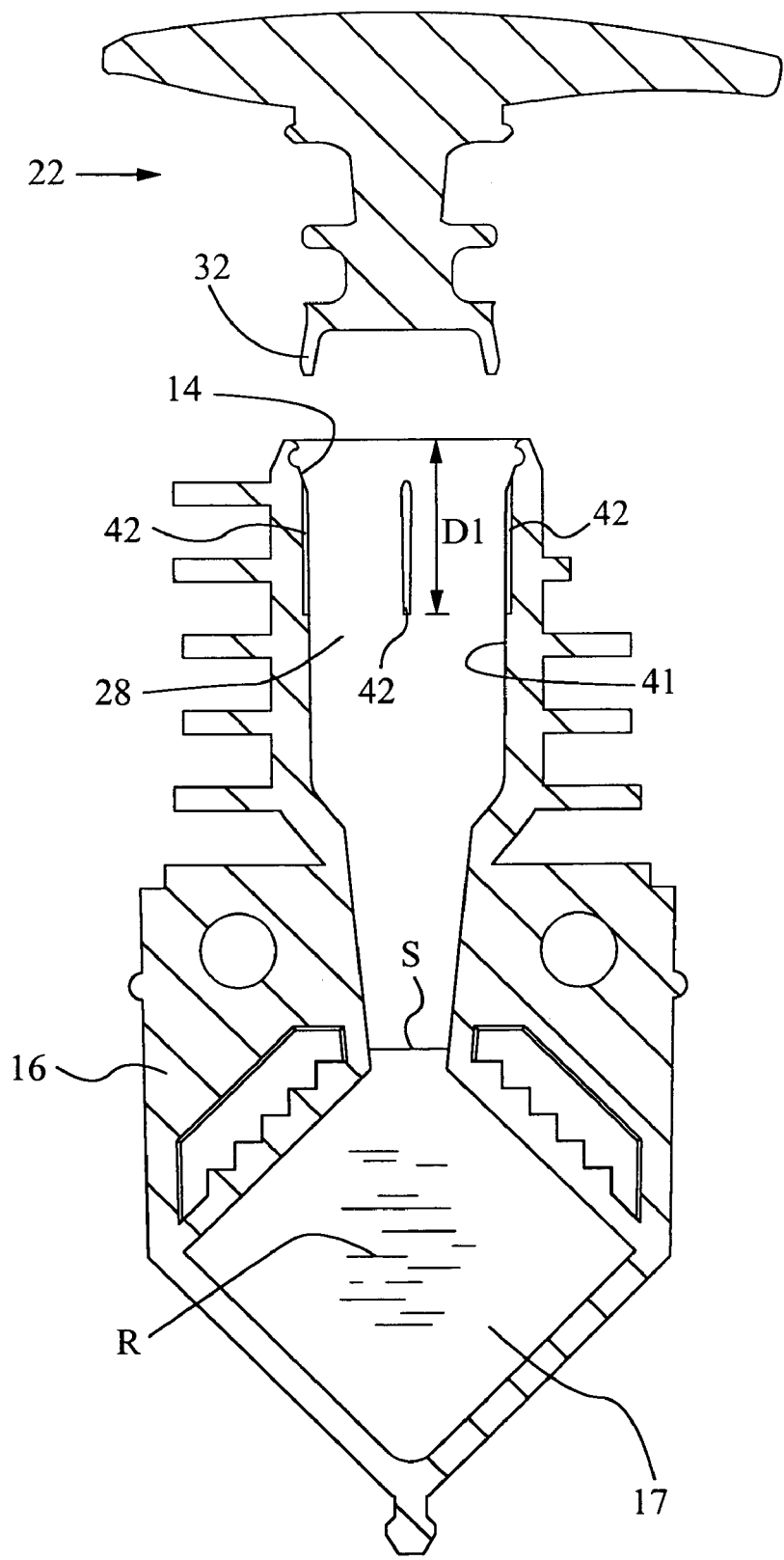
FIGS. 7A-7D are schematic, cross-sectional views of a plunger being inserted into a channel of the reaction vessel of FIG. 1.

Referring to FIG. 7A, the rigid frame 16 has an inner surface 41 defining the channel 28. The inner surface 41 preferably has one or more pressure control grooves 42 formed therein. In the preferred embodiment, the inner surface has four pressure control grooves (only three shown in the view of FIG. 7A) spaced equidistantly about the circumference of the channel 28. The pressure control grooves 42 extend from the port 14 to a predetermined depth D1 in the channel 28. The pressure control grooves 42 allow gas to escape from the channel 28 and thus prevent pressurization of the chamber 17 until the piston 32 reaches the depth D1 in the channel. When the piston 32 reaches the depth D1, the piston establishes an annular seal with the walls of the channel 28 and begins to compress air trapped in the channel. The compression of the trapped air causes the desired pressurization of the chamber 17.

Figure 7B:
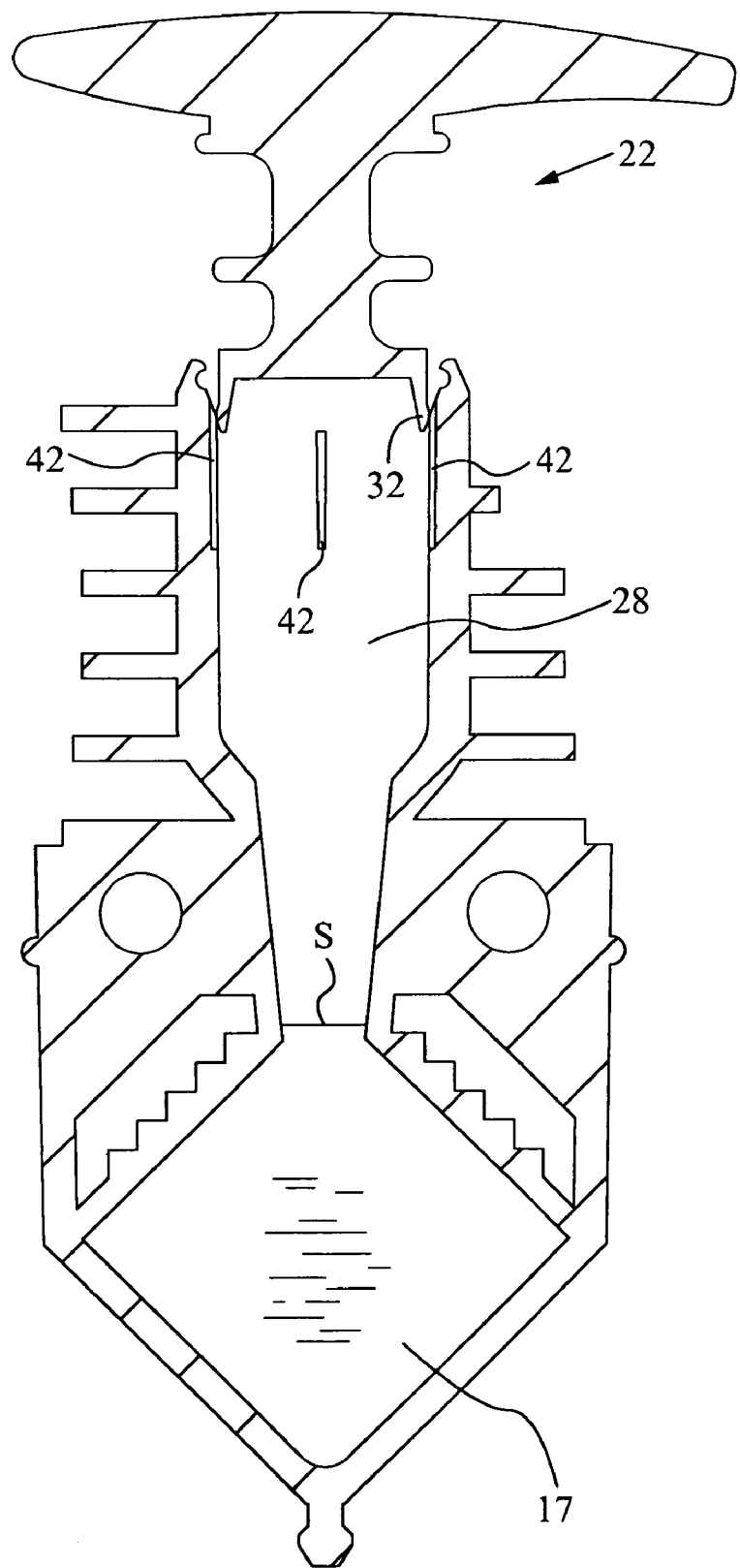

The stroke of the plunger 22 into the channel 28 is fully illustrated in FIGS. 7A-7D. As shown in FIG. 7A, prior to inserting the plunger 22 into the channel 28, the chamber 17 is filled with the desired reaction mixture R. Specific methods for filling the chamber (e.g., pipetting) are discussed in detail below. The reaction mixture R fills the vessel 12 to a liquid surface level S. Also prior to inserting the plunger 22 into the channel 28, the channel 28 contains air having pressure equal to the pressure of the atmosphere external to the vessel, hereinafter called ambient pressure. The ambient pressure is usually standard atmospheric pressure, e.g., about 14.7 pounds per square inch (psi). As shown in FIG. 7B, when the plunger 22 is first inserted into the channel 28, the piston 32 begins to displace the air in the channel. The displaced air escapes from the channel 28 through the pressure control grooves 42.

Figure 7C:
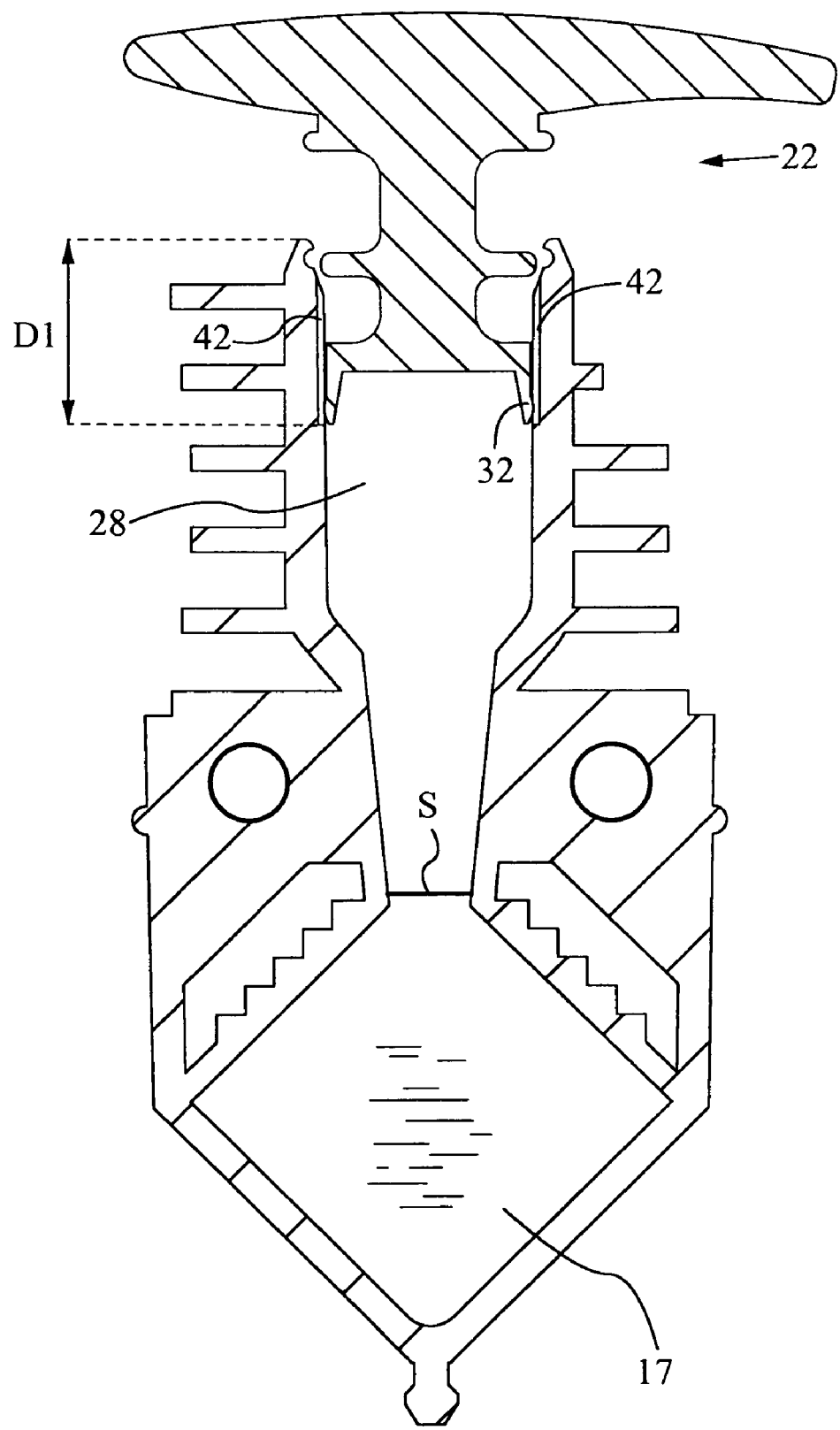
Figure 7D:
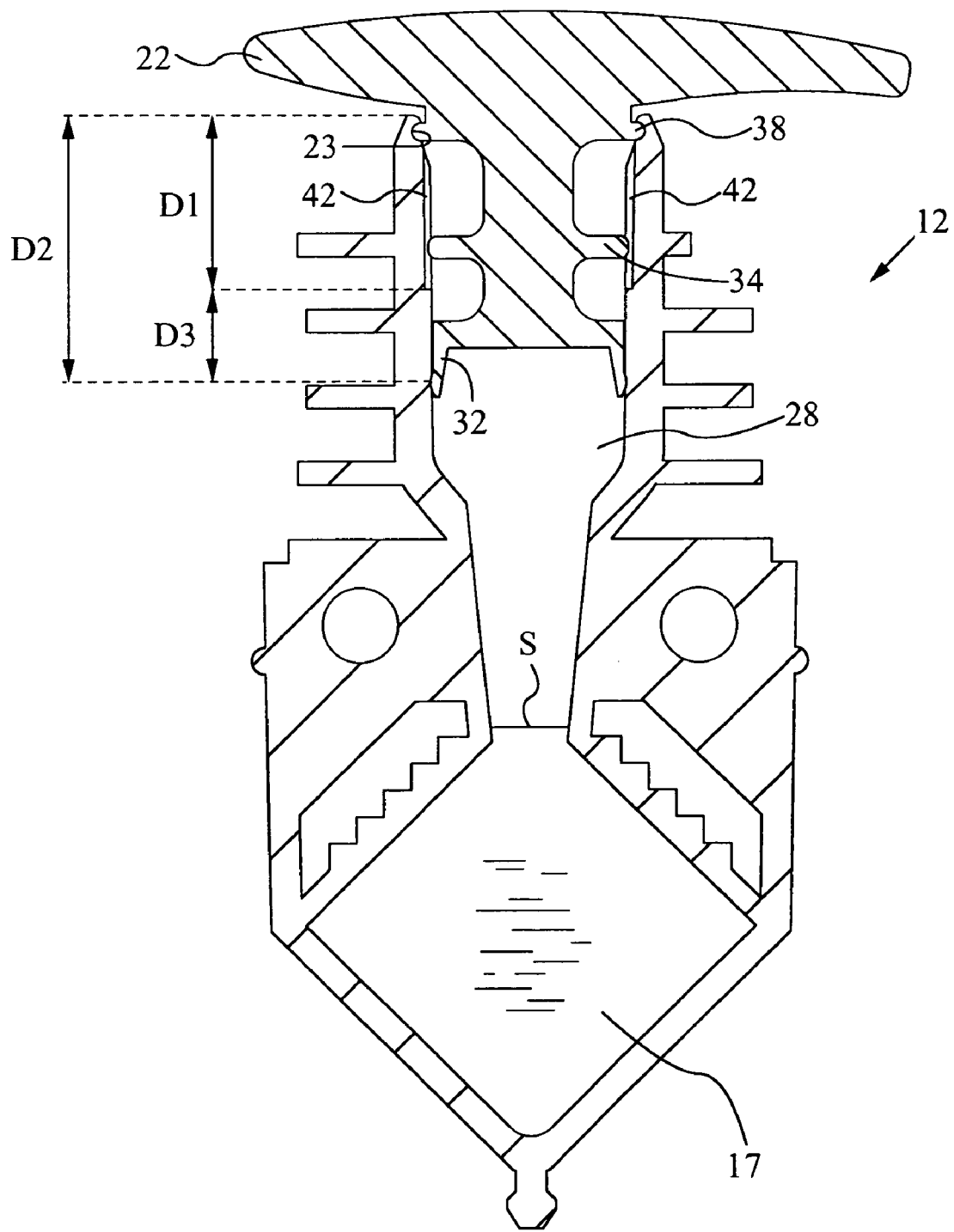

Referring now to FIG. 7C, when the piston 32 reaches the depth D1 at which the pressure control grooves end, the piston 32 establishes an annular seal with the walls of the channel 28 and begins to compress air trapped in the channel between the piston 32 and the surface level S of the reaction mixture. The reaction mixture is usually a liquid and therefore substantially incompressible by the piston. The air trapped in the channel 28, however, may be compressed to increase pressure in the chamber. As shown in FIG. 7D, as the plunger 22 is inserted further into the channel 28, the alignment ring 34 keeps the plunger 22 coaxially aligned with the channel 28 as the piston 32 continues to compress air trapped in the channel. When the plunger 22 is fully inserted in the channel 28, the snap ring 38 snaps into the annular recess 23, ending the plunger stroke.

When the plunger 22 is fully inserted, the piston 32 seals the channel 28 at a depth D2 which is lower than the depth D1 at which the pressure control grooves 42 terminate. The distance D3 traveled by the piston 32 between depths D1 and D2, i.e. the distance of the pressure stroke, determines the amount of pressurization of the chamber 17. Referring again to FIG. 5, the pressure in the chamber 17 should be sufficiently high to ensure that the flexible major walls 18 of the chamber outwardly expand to contact and conform to the surfaces of the plates 50A, 50B. The pressure should not be so great, however, that the flexible walls 18 burst, become unattached from the rigid frame 16, or deform the frame or plates.

It is presently preferred to pressurize the chamber to a pressure in the range of 2 to 50 psi above ambient pressure. This range is presently preferred because 2 psi is generally enough pressure to ensure conformity between the flexible walls 18 and the surfaces of the plates 50A, 50B, while pressures above 50 psi may cause bursting of the walls 18 or deformation of the frame 16 or plates 50A, 50B. More preferably, the chamber 17 is pressurized to a pressure in the range of 8 to 15 psi above ambient pressure. This range is more preferred because it is safely within the practical limits described above, i.e. pressures of 8 to 15 psi are usually more than enough to ensure that the flexible walls 18 contact and conform to the surfaces of the plates 50A, SOB, but are significantly lower than the pressures that might burst the walls 18 or deform the frame 16.

Referring again to FIG. 7D, the desired pressurization of the chamber 17 may be achieved by proper design of the plunger 22, channel 28, and pressure control grooves 42 and by use of the equation:

$$P_1 * V_1 = P_2 * V_2;$$

where:

$P_1$ is equal to the pressure in the vessel 12 prior to insertion of the plunger 22;

$V_1$ is equal to the volume of the channel 28 between the liquid surface level S and the depth $D_1$ to which the pressure control grooves 42 extend;

$P_2$ is equal to the desired final pressure in the chamber 17 after insertion of the plunger 22 into the channel 28; and $V_2$ is equal to the volume of the channel 28 between the liquid surface level S and the depth $D_2$ at which the piston 32 establishes a seal with the walls of the channel 28 when the plunger 22 is fully inserted into the channel.

To ensure the desired pressurization $P_2$ of the chamber 17, one should size the channel 28 and pressure stroke distance $D_3$ such that the ratio of the volumes $V_1:V_2$ is equal to the ratio of the pressures $P_2:P_1$. An engineer having ordinary skill in the art will be able to select suitable values for the volumes $V_1$ and $V_2$ using the description and equation given above. For example, in the presently preferred embodiment, the initial pressure $P_1$ in the vessel is equal to standard atmospheric pressure of about 14.7 psi, the volume $V_1$ is equal to 110 µl, the depth $D_1$ is equal to 0.2 inches, the depth $D_2$ is equal to 0.28 inches to give a pressure stroke distance $D_3$ of 0.08 inches, and the volume $V_2$ is equal to 60 µl to give a final pressure $P_2$ of about 26.7 psi (the desired 12 psi above ambient pressure). This is just one example of suitable dimensions for the vessel 12 and is not intended to limit the scope of the invention. Many other suitable values may be selected.

In selecting suitable dimensions for the channel 28 and pressure stroke distance $D_3$ (and thus the volumes $V_1$, $V_2$), there is no theoretical limit to how large or small the dimensions may be. It is only important that the ratio of the volumes V1:V2 yield the desired final desired pressure $P_2$ in the chamber. As a practical matter, however, it is presently preferred to design the vessel such that the distance $D_3$ of the pressure stroke is at least 0.05 inches, i.e., so that the plunger 22 when fully inserted into the channel 28 extends to a depth $D_2$ that is at least 0.05 inches below the depth $D_1$ at which the pressure control grooves end. This minimum length of the pressure stroke is preferred to reduce or make negligible the effect that any manufacturing or operating errors may have on the pressurization of the chamber. For example, the length of the pressure stroke may differ slightly from vessel to vessel due to manufacturing deviations, or the volume of air compressed may vary due to operator error in filling the vessel (e.g., different fill levels). If the vessel is designed to have a sufficiently long pressure stroke, however, such variances will have a lesser or negligible effect on the ratio of volumes $V_1:V_2$ and suitable pressurization of the chamber will still occur. In addition, to provide a safety margin for manufacturing or operator errors, one should select a pressure stroke sufficient to achieve a final pressure $P_2$ that is safely higher (e.g., at least 3 psi higher) than the minimum pressure needed to force the flexible walls of the chamber against the inner surfaces of the plates. With such a safety margin, any deviations in the final pressure due to manufacturing deviations or errors in filling the chamber will have a negligible effect and suitable pressurization of the chamber 17 will still occur. As stated above, the plunger stroke is preferably designed to increase pressure in the chamber 17 to a pressure in the range of 8 to 15 psi above ambient pressure to provide the safety margin.

The pressure control grooves 42 provide several important advantages. First, the pressure control grooves 42 provide a simple mechanism for precisely and accurately controlling the pressure stroke of the plunger 22, and hence the pressurization of the chamber 17. Second, the pressure control grooves 42 allow the plunger 22 to become fully aligned with the channel 28 before the pressure stroke begins and thus prevent the plunger from becoming misaligned or cocked in the channel. This ensures a highly consistent pressure stroke. Although it is possible for the vessel to have only one pressure control groove, it is preferable for the vessel to have multiple pressure control grooves (e.g., 2 to 6 grooves) spaced equidistantly about the circumference of the channel 28. Referring again to FIG. 7A, the pressure control grooves 42 preferably cut about 0.01 to 0.03 inches into the surface 41 defining the channel 28. This range is preferred so that the pressure control grooves 42 are large enough to allow air to escape from the channel 28, but do not cut so deeply into the surface 41 that they degrade the structural integrity of the frame 16.

Although the pressure control grooves 42 are highly preferred, it is also possible to construct the vessel 12 without the pressure control grooves and still achieve the desired pressurization of the chamber 17. One disadvantage of this embodiment is that the plunger 22 may become misaligned or cocked in the channel 28 during the pressure stroke so that less consistent results are achieved. In embodiments in which the vessel lacks pressure control grooves, the pressure stroke of the plunger 22 begins when the piston 32 enters the channel 28 and establishes a seal with the walls of the channel. In these embodiments, the volume $V_1$ (for use in the equation above) is equal to the volume of the channel 28 between the liquid surface level S and the port 14 where the piston 32 first establishes a seal with the walls of the channel. To ensure the desired pressurization $P_2$ of the chamber 17, one should size the channel 28 and length of the pressure stroke such that the ratio of the volumes $V_1:V_2$ is equal to the ratio of the pressures $P_2:P_1$. As described previously, the minimum length of the pressure stroke is preferably 0.05 inches to minimize the effect of any manufacturing or operational deviations.

Referring again to FIG. 2, the vessel 12 also preferably includes optical windows for in situ optical interrogation of the reaction mixture in the chamber 17. In the preferred embodiment, the optical windows are the side walls 19A, 19B of the rigid frame 16. The side walls 19A, 19B are optically transmissive to permit excitation of the reaction mixture in the chamber 17 through the side wall 19A and detection of light emitted from the chamber 17 through the side wall 19B. Arrows A represent illumination beams entering the chamber 17 through the side wall 19A and arrows B represent emitted light (e.g., fluorescent emission from labeled analytes in the reaction mixture) exiting the chamber 17 through the side wall 19B.

The side walls 19A, 19B are preferably angularly offset from each other. It is usually preferred that the walls 19A, 19B are offset from each other by an angle of about 90°. A 90° angle between excitation and detection paths assures that a minimum amount of excitation radiation entering through the wall 19A will exit through wall 19B. In addition, the 90° angle permits a maximum amount of emitted light, e.g. fluorescence, to be collected through wall 19B. The walls 19A, 19B are preferably joined to each other to form a "V" shaped intersection at the bottom of the chamber 17. Alternatively, the angled walls 19A, 19B need not be directly joined to each other, but may be separated by an intermediary portion, such as another wall or various mechanical or fluidic features which do not interfere with the thermal and optical performance of the vessel. For example, the walls 19A, 19B may meet at a port which leads to another processing area in communication with the chamber 17, such as an integrated capillary electrophoresis area. In the presently preferred embodiment, a locating tab 27 extends from the frame 16 below the intersection of walls 19A, 19B. The locating tab 27 is used to properly position the vessel 12 in a heat-exchanging module described below with reference to FIG. 8.

Optimum optical sensitivity may be attained by maximizing the optical path length of the light beams exciting the labeled analytes in the reaction mixture and the emitted light that is detected, as represented by the equation:

$$I_o/I_i = C*L*A,$$

where $I_o$ is the illumination output of the emitted light in volts, photons or the like, C is the concentration of analyte to be detected, $I_i$ is the input illumination, L is the path length, and A is the intrinsic absorptivity of the dye used to label the analyte.

Figure 4:
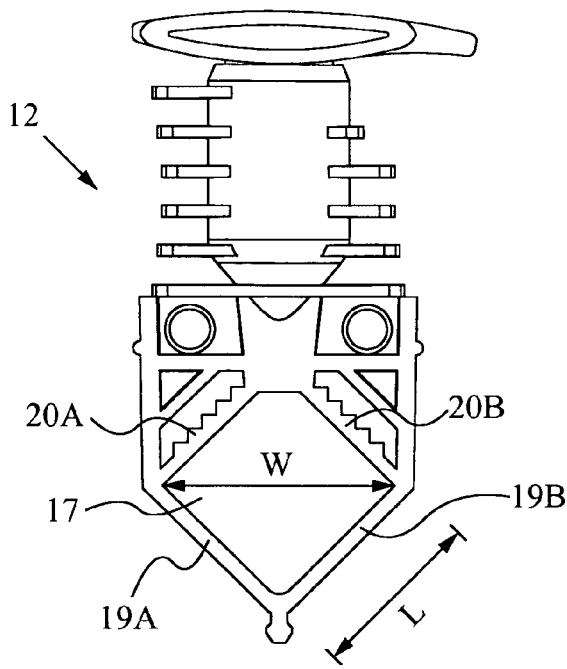
FIG. 4 is another front view of the vessel of FIG. 1.

The thin, flat reaction vessel 12 of the present invention optimizes detection sensitivity by providing maximum optical path length per unit analyte volume. Referring to FIGS. 4-5, the vessel 12 is preferably constructed such that each of the sides walls 19A, 19B, 20A, 20B of the chamber 17 has a length L in the range of 1 to 15 mm, the chamber has a width W in the range of 1.4 to 20 mm, the chamber has a thickness T in the range of 0.5 to 5 mm, and the ratio of the width W of the chamber to the thickness T of the chamber is at least 2:1. These parameters are presently preferred to provide a vessel having a relatively large average optical path length through the chamber, i.e. 1 to 15 mm on average, while still keeping the chamber sufficiently thin to allow for extremely rapid heating and cooling of the reaction mixture contained therein. The average optical path length of the chamber 17 is the distance from the center of the side wall 19A to the center of the chamber 17 plus the distance from the center of the chamber 17 to the center of the side wall 19B. As used herein, the thickness T of the chamber 17 is defined as the thickness of the chamber prior to the outward expansion of the major walls, i.e. the thickness T of the chamber is defined by the thickness of the frame 16.

More preferably, the vessel 12 is constructed such that each of the sides walls 19A, 19B, 20A, 20B of the chamber 17 has a length L in the range of 5 to 12 mm, the chamber has a width W in the range of 7 to 17 mm, the chamber has a thickness T in the range of 0.5 to 2 mm, and the ratio of the width W of the chamber to the thickness T of the chamber is at least 4:1. These ranges are more preferable because they provide a vessel having both a larger average optical path length (i.e., 5 to 12 mm) and a volume capacity in the range of 12 to 100 µl while still maintaining a chamber sufficiently thin to permit extremely rapid heating and cooling of a reaction mixture. The relatively large volume capacity provides for increased sensitivity in the detection of low concentration analytes, such as nucleic acids.

In the preferred embodiment, the reaction vessel 12 has a diamond-shaped chamber 17 defined by the side walls 19A, 19B, 20A, 20B, each of the side walls has a length of about 10 mm, the chamber has a width of about 14 mm, the chamber has a thickness T of 1 mm as defined by the thickness of the frame 16, and the chamber has a volume capacity of about 100 µl. This reaction vessel provides a relatively large average optical path length of 10 mm through the chamber 17. Additionally, the thin chamber allows for extremely rapid heating and/or cooling of the reaction mixture contained therein. The diamond-shape of the chamber 17 helps prevent air bubbles from forming in the chamber as it is filled with the reaction mixture and also aids in optical interrogation of the mixture.

The frame 16 is preferably made of an optically transmissive material, e.g., a polycarbonate or clarified polypropylene, so that the side walls 19A, 19B are optically transmissive. As used herein, the term optically transmissive means that one or more wavelengths of light may be transmitted through the walls. In the preferred embodiment, the optically transmissive walls 19A, 19B are substantially transparent. In addition, one or more optical elements may be present on the optically transmissive side walls 19A, 19B. The optical elements may be designed, for example, to maximize the total volume of solution which is illuminated by a light source, to focus excitation light on a specific region of the chamber 17, or to collect as much fluorescence signal from as large a fraction of the chamber volume as possible. In alternative embodiments, the optical elements may comprise gratings for selecting specific wavelengths, filters for allowing only certain wavelengths to pass, or colored lenses to provide filtering functions. The wall surfaces may be coated or comprise materials such as liquid crystal for augmenting the absorption of certain wavelengths. In the presently preferred embodiment, the optically transmissive walls 19A, 19B are substantially clear, flat windows having a thickness of about 1 mm.

As shown in FIG. 2, the side walls 20A, 20B preferably includes reflective faces 21 which internally reflect light trying to exit the chamber 17 through the side walls 20A, 20B. The reflective faces 21 are arranged such that adjacent faces are angularly offset from each other by about 90°. In addition, the frame 16 defines open spaces between the side walls 20A, 20B and support ribs 15. The open spaces are occupied by ambient air that has a different refractive index than the material composing the frame (e.g., plastic). Due to the difference in the refractive indexes, the reflective faces 21 are effective for internally reflecting light trying to exit the chamber through the walls 20A, 20B and provide for increased detection of optical signal through the walls 19A, 19B. In the preferred embodiment, the optically transmissive side walls 19A, 19B define the bottom portion of the diamond-shaped chamber 17, and the retro-reflective side walls 20A, 20B define the top portion of the chamber.

Figure 3:
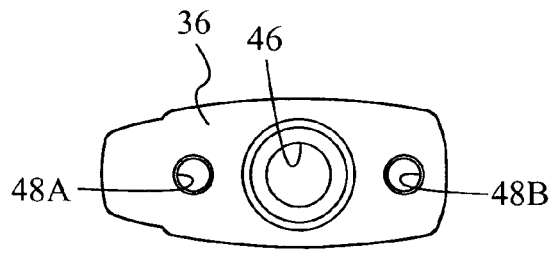
FIG. 3 is a top view of a plunger cap of the vessel of FIG. 1.

The reaction vessel 12 may be used in manual operations performed by human technicians or in automated operations performed by machines, e.g. pick-and-place machines. As shown in FIG. 1, for the manual embodiments, the vessel 12 preferably includes finger grips 26 and a leash 24 that conveniently attaches the plunger 22 to the body of the vessel 12. As shown in FIG. 3, for automated embodiments, the plunger cap 36 preferably includes a tapered engagement aperture 46 for receiving and establishing a fit with a robotic arm or machine tip (not shown in FIG. 3), thus enabling the machine tip to pick and place the plunger in the channel. The engagement aperture 46 preferably has tapered side walls for establishing a friction fit with the machine tip. Alternatively, the engagement aperture may be designed to establish a vacuum fit with the machine tip. The plunger cap 36 may optionally include alignment apertures 48A, 48B used by the machine tip to properly align the plunger cap 36 as the plunger is inserted into the channel, as is described in greater detail below with reference to FIG. 25.

A preferred method for fabricating the reaction vessel 12 will now be described with reference to FIGS. 1-2. The reaction vessel 12 may be fabricated by first molding the rigid frame 16 using known injection molding techniques. The frame 16 is preferably molded as a single piece of polymeric material, e.g., clarified polypropylene. After the frame 16 is produced, thin, flexible sheets are cut to size and sealed to opposite sides of the frame 16 to form the major walls 18 of the chamber 17.

The major walls 18 are preferably cast or extruded films of polymeric material, e.g., polypropylene films, that are cut to size and attached to the frame 16 using the following procedure. A first piece of film is placed over one side of the bottom portion of the frame 16. The frame 16 preferably includes a tack bar 47 for aligning the top edge of the film. The film is placed over the bottom portion of the frame 16 such that the top edge of the film is aligned with the tack bar 47 and such that the film completely covers the bottom portion of the frame 16 below the tack bar 47. The film should be larger than the bottom portion of the frame 16 so that it may be easily held and stretched flat across the frame. The film is then cut to size to match the outline of the frame by clamping to the frame the portion of the film that covers the frame and cutting away the portions of the film that extend past the perimeter of the frame using, e.g., a laser or die. The film is then tack welded to the frame, preferably using a laser.

The film is then sealed to the frame 16, preferably by heat sealing. Heat sealing is presently preferred because it produces a strong seal without introducing potential contaminants to the vessel as the use of adhesive or solvent bonding techniques might do. Heat sealing is also simple and inexpensive. At a minimum, the film should be completely sealed to the surfaces of the side walls 19A, 19B, 20A, 20B. More preferably, the film is additionally sealed to the surfaces of the support ribs 15 and tack bar 47. The heat sealing may be performed using, e.g., a heated platen. An identical procedure may be used to cut and seal a second sheet to the opposite side of the frame 16 to complete the chamber 17.

Many variations to this fabrication procedure are possible. For example, in an alternative embodiment, the film is stretched across the bottom portion of the frame 16 and then sealed to the frame prior to cutting the film to size. After sealing the film to the frame, the portions of the film that extend past the perimeter of the frame are cut away using, e.g., a laser or die.

The plunger 22 is also preferably molded from polymeric material, preferably polypropylene, using known injection molding techniques. As shown in FIG. 1, the frame 16, plunger 22, and leash 24 connecting the plunger to the frame may all be formed in the same mold to form a one-piece part. This embodiment of the vessel is especially suitable for manual use in which a human operator fills the vessel and inserts the plunger 22 into the channel 28. The leash 24 ensures that the plunger 22 is not lost or dropped on the floor. Alternatively, as shown in FIG. 2, the plunger 22 may be molded separately from the frame 16 so that the plunger and frame are separate pieces. This embodiment is especially suitable for automated use of the vessel in which the plunger 22 is picked and placed into the channel 28 by an automated machine.

Although it is presently preferred to mold the frame 16 as a single piece, it is also possible to fabricate the frame from multiple pieces. For example, the side walls 19A, 19B forming the angled optical windows may be molded from polycarbonate, which has good optical transparency, while the rest of the frame is molded from polypropylene, which is inexpensive and compatible with PCR. The separate pieces can be attached together in a secondary step. For example, the side walls 19A, 19B may be press-fitted and/or bonded to the remaining portion of the frame 16. The flexible walls 18 may then be attached to opposite sides of the frame 16 as previously described.

Referring again to FIG. 5, the plates 50A, 50B may be made of various thermally conductive materials including ceramics or metals. Suitable ceramic materials include aluminum nitride, aluminum oxide, beryllium oxide, and silicon nitride. Other materials from which the plates may be made include, e.g., gallium arsenide, silicon, silicon nitride, silicon dioxide, quartz, glass, diamond, polyacrylics, polyamides, polycarbonates, polyesters, polyimides, vinyl polymers, and halogenated vinyl polymers, such as polytetrafluoroethylenes. Other possible plate materials include chrome/aluminum, superalloys, zircaloy, aluminum, steel, gold, silver, copper, tungsten, molybdenum, tantalum, brass, sapphire, or any of the other numerous ceramic, metal, or polymeric materials available in the art.

Ceramic plates are presently preferred because their inside surfaces may be conveniently machined to very high smoothness for high wear resistance, high chemical resistance, and good thermal contact to the flexible walls of the reaction vessel. Ceramic plates can also be made very thin, preferably between about 0.6 and 1.3 mm, for low thermal mass to provide for extremely rapid temperature changes. A plate made from ceramic is also both a good thermal conductor and an electrical insulator, so that the temperature of the plate may be well controlled using a resistive heating element coupled to the plate.

Various thermal elements may be employed to heat and/or cool the plates 50A, 50B and thus control the temperature of the reaction mixture in the chamber 17. In general, suitable heating elements for heating the plate include conductive heaters, convection heaters, or radiation heaters. Examples of conductive heaters include resistive or inductive heating elements coupled to the plates, e.g., resistors or thermoelectric devices.

Suitable convection heaters include forced air heaters or fluid heat-exchangers for flowing fluids past the plates. Suitable radiation heaters include infrared or microwave heaters. Similarly, various cooling elements may be used to cool the plates. For example, various convection cooling elements may be employed such as a fan, peltier device, refrigeration device, or jet nozzle for flowing cooling fluids past the surfaces of the plates. Alternatively, various conductive cooling elements may be used, such as a heat sink, e.g. a cooled metal block, in direct contact with the plates.

Figure 6:
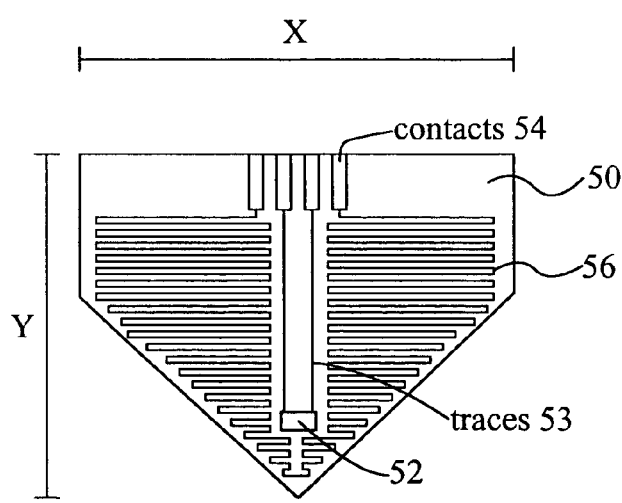
FIG. 6 is a front view of one of the plates of FIG. 5.

Referring to FIG. 6, in the preferred embodiment, each plate 50 has a resistive heating element 56 disposed on its outer surface. The resistive heating element 56 is preferably a thick or thin film and may be directly screen printed onto each plate 50, particularly plates comprising a ceramic material, such as aluminum nitride or aluminum oxide. Screen-printing provides high reliability and low cross-section for efficient transfer of heat into the reaction chamber. Thick or thin film resistors of varying geometric patterns may be deposited on the outer surfaces of the plates to provide more uniform heating, for example by having denser resistors at the extremities and thinner resistors in the middle. Although it is presently preferred to deposit a heating element on the outer surface of each plate, a heating element may alternatively be baked inside of each plate, particularly if the plates are ceramic. The heating element 56 may comprise metals, tungsten, polysilicon, or other materials that heat when a voltage difference is applied across the material.

The heating element 56 has two ends which are connected to respective contacts 54 which are in turn connected to a voltage source (not shown in FIG. 6) to cause a current to flow through the heating element. Each plate 50 also preferably includes a temperature sensor 52, such as a thermocouple, thermistor, or RTD, which is connected by two traces 53 to respective contacts 54. The temperature sensor 52 may be used to monitor the temperature of the plate 50 in a controlled feedback loop.

It is important that the plates have a low thermal mass to enable rapid heating and cooling of the plates. In particular, it is presently preferred that each of the plates has a thermal mass less than about 5 J/° C., more preferably less than 3 J/° C., and most preferably less than 1 J/° C. As used herein, the term thermal mass of a plate is defined as the specific heat of the plate multiplied by the mass of the plate. In addition, each plate should be large enough to cover a respective major wall of the reaction chamber. In the presently preferred embodiment, for example, each of the plates has a width X in the range of 2 to 22 mm, a length Y in the range of 2 to 22 mm, and a thickness in the range of 0.5 to 5 mm. The width X and length Y of each plate is selected to be slightly larger than the width and length of the reaction chamber. Moreover, each plate preferably has an angled bottom portion matching the geometry of the bottom portion of the reaction chamber, as is described below with reference to FIG. 12. Also in the preferred embodiment, each of the plates is made of aluminum nitride having a specific heat of about 0.75 J/g° C. The mass of each plate is preferably in the range of 0.005 to 5.0 g so that each plate has a thermal mass in the range of 0.00375 to 3.75 J/° C.

Figure 8:
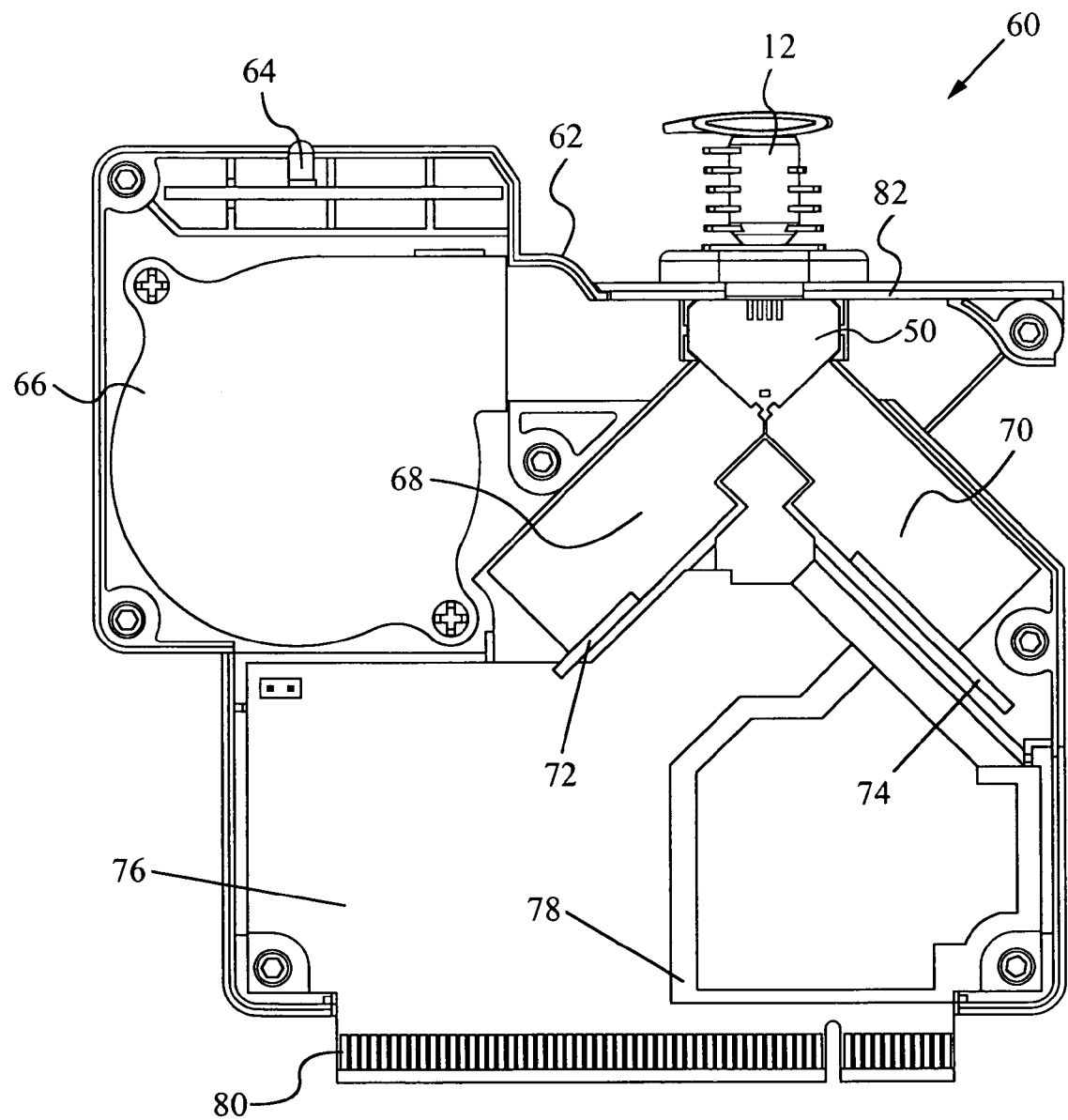
FIG. 8 is a schematic, front view of a heat-exchanging module according to the present invention having a thermal sleeve, a pair of optics assemblies, and a cooling system. The reaction vessel of FIG. 1 is inserted into the thermal sleeve.

FIG. 8 is a schematic side view of a heat-exchanging module 60 into which the reaction vessel 12 is inserted for thermal processing and optical interrogation. The module 60 preferably includes a housing 62 for holding the various components of the module. The module 60 also includes the thermally conductive plates 50 described above. The housing 62 includes a slot (not shown in FIG. 8) above the plates 50 so that the reaction chamber of the vessel 12 may be inserted through the slot and between the plates. The heat-exchanging module 60 also preferably includes a cooling system, such as a fan 66. The fan 66 is positioned to blow cooling air past the surfaces of the plates 50 to cool the plates and hence cool the reaction mixture in the vessel 12. The housing 62 preferably defines channels for directing the cooling air past the plates 50 and out of the module 60.

The heat-exchanging module 60 further includes an optical excitation assembly 68 and an optical detection assembly 70 for optically interrogating the reaction mixture contained in the vessel 12. The excitation assembly 68 includes a first circuit board 72 for holding its electronic components, and the detection assembly 68 includes a second circuit board 74 for holding its electronic components. The excitation assembly 68 includes one or more light sources, such as LEDs, for exciting fluorescently-labeled analytes in the vessel 12. The excitation assembly 68 also includes one or more lenses for collimating the light from the light sources, as well as filters for selecting the excitation wavelength ranges of interest. The detection assembly 70 includes one or more detectors, such as photodiodes, for detecting the light emitted from the vessel 12. The detection assembly 70 also includes one or more lenses for focusing and collimating the emitted light, as well as filters for selecting the emission wavelength ranges of interest. The specific components of the optics assemblies 68, 70 are described in greater detail below with reference to FIGS. 16-19.

The optics assemblies 68, 70 are positioned in the housing 62 such that when the chamber of the vessel 12 is inserted between the plates 50, the first optics assembly 68 is in optical communication with the chamber 17 through the optically transmissive side wall 19A (see FIG. 2) and the second optics assembly 70 is in optical communication with the chamber through the optically transmissive side wall 19B (FIG. 2). In the preferred embodiment, the optics assemblies 68, 70 are placed into optical communication with the optically transmissive side walls by simply locating the optics assemblies 68, 70 next to the bottom edges of the plates 50 so that when the chamber of the vessel is placed between the plates, the optics assemblies 68, 70 directly contact, or are in close proximity to, the side walls.

Figure 12:
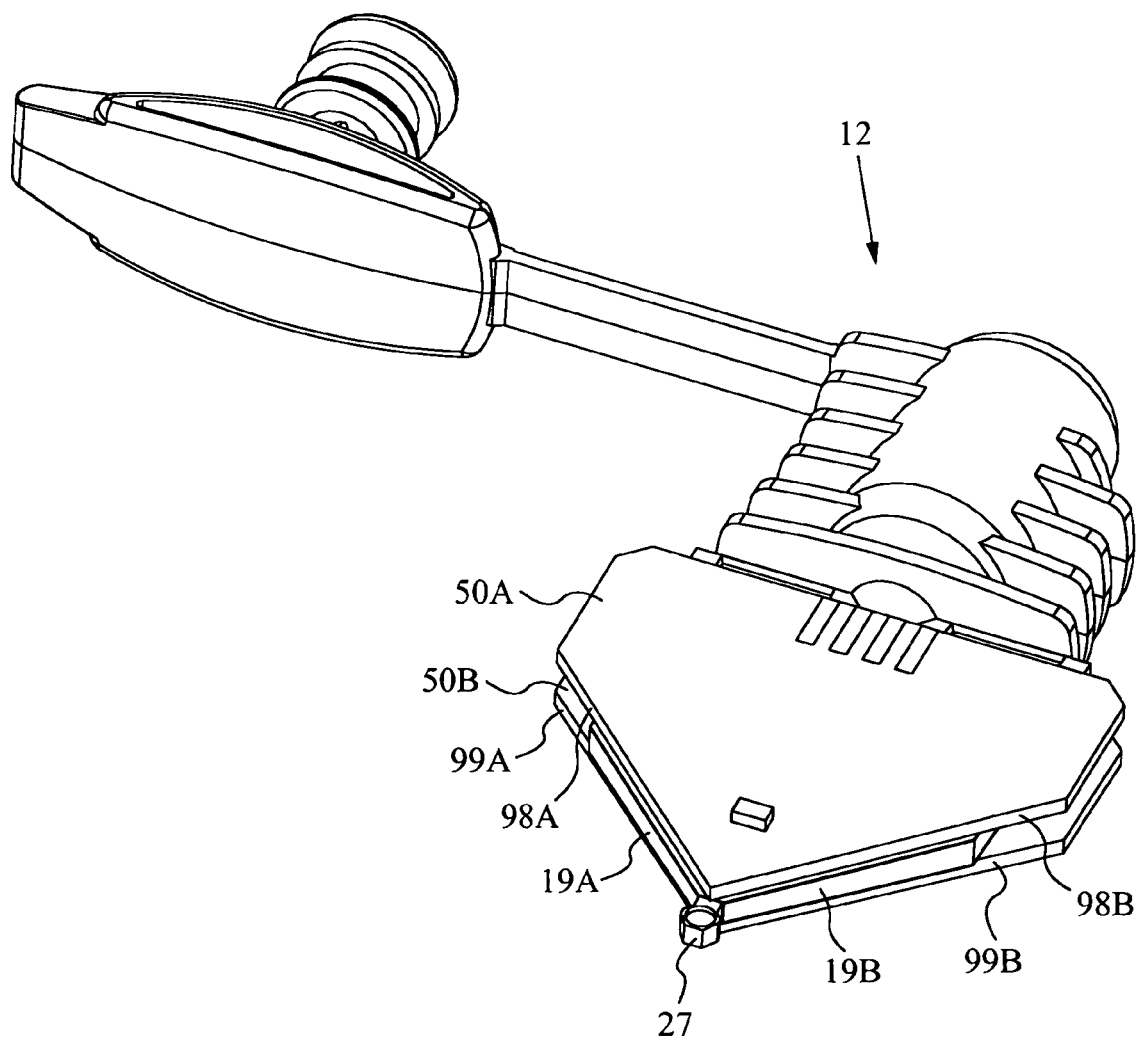
FIG. 12 is an isometric view of the reaction vessel of FIG. 1 inserted between the plates of FIG. 5.

As shown in FIG. 12, the vessel 12 preferably has an angled bottom portion (e.g., triangular) formed by the optically transmissive side walls 19A, 19B. Each of the plates 50A, 50B has a correspondingly shaped bottom portion. The bottom portion of the first plate 50A has a first bottom edge 98A and a second bottom edge 98B. Similarly, the bottom portion of the second plate 50B has a first bottom edge 99A and a second bottom edge 99B. The first and second bottom edges of each plate are preferably angularly offset from each other by the same angle that the side walls 19A, 19B are offset from each other (e.g., 90°). Additionally, the plates 50A, 50B are preferably positioned to receive the chamber of the vessel 12 between them such that the first side wall 19A is positioned substantially adjacent and parallel to each of the first bottom edges 98A, 99A and such that the second side wall 19B is positioned substantially adjacent and parallel to each of the second bottom edges 98B, 99B. This arrangement provides for easy optical access to the optically transmissive side walls 19A, 19B and hence to the chamber of the vessel 12.

The side walls 19A, 19B may be positioned flush with the edges of the plates 50A, 50B, or more preferably, the side walls 19A, 19B may be positioned such that they protrude slightly past the edges of the plates. As is explained below with reference to FIGS. 16-19, each optics assembly preferably includes a lens that physically contacts a respective one of the side walls 19A, 19B. It is preferred that the side walls 19A, 19B protrude slightly (e.g., 0.02 to 0.3 mm) past the edges of the plates 50A, 50B so that the plates do not physically contact and damage the lenses. A gel or fluid may optionally be used to establish or improve optical communication between each optics assembly and the side walls 19A, 19B. The gel or fluid should have a refractive index close to the refractive indexes of the elements that it is coupling.

Referring again to FIG. 8, the optics assemblies 68, 70 are preferably arranged to provide a 90° angle between excitation and detection paths. The 90° angle between excitation and detection paths assures that a minimum amount of excitation radiation entering through the first side wall of the chamber exits through the second side wall. Also, the 90° angle permits a maximum amount of emitted radiation to be collected through the second side wall. In the preferred embodiment, the vessel 12 includes a locating tab 27 (see FIG. 2) that fits into a slot formed between the optics assemblies 68, 70 to ensure proper positioning of the vessel 12 for optical detection. For improved detection, the module 60 also preferably includes a light-tight lid (not shown) that is placed over the top of the vessel 12 and made light-tight to the housing 62 after the vessel is inserted between the plates 50.

Although it is presently preferred to locate the optics assemblies 68, 70 next to the bottom edges of the plates 50, many other arrangements are possible. For example, optical communication may be established between the optics assemblies 68, 70 and the walls of the vessel 12 via optical fibers, light pipes, wave guides, or similar devices. One advantage of these devices is that they eliminate the need to locate the optics assemblies 68, 70 physically adjacent to the plates 50. This leaves more room around the plates in which to circulate cooling air or refrigerant, so that cooling may be improved.

The heat-exchanging module 60 also includes a PC board 76 for holding the electronic components of the module and an edge connector 80 for connecting the module 60 to a base instrument, as will be described below with reference to FIG. 22. The heating elements and temperature sensors on the plates 50, as well as the optical boards 72, 74, are connected to the PC board 76 by flex cables (not shown in FIG. 8 for clarity of illustration). The module 60 may also include a grounding trace 78 for shielding the optical detection circuit. The module 60 also preferably includes an indicator, such as an LED 64, for indicating to a user the current status of the module such as "ready to load sample", "ready to load reagent," "heating," "cooling," "finished," or "fault".

The housing 62 may be molded from a rigid, high-performance plastic, or other conventional material. The primary functions of the housing 62 are to provide a frame for holding the plates 50, optics assemblies 68, 70, fan 66, and PC board 76. The housing 62 also preferably provides flow channels and ports for directing cooling air from the fan 66 across the surfaces of the plates 50 and out of the housing. In the preferred embodiment, the housing 62 comprises complementary pieces (only one piece shown in the schematic side view of FIG. 8) that fit together to enclose the components of the module 60 between them.

The opposing plates 50 are positioned to receive the chamber of the vessel 12 between them such that the flexible major walls of the chamber contact and conform to the inner surfaces of the plates. It is presently preferred that the plates 50 be held in an opposing relationship to each other using, e.g., brackets, supports, or retainers. Alternatively, the plates 50 may be spring-biased towards each other as described in International Publication Number WO 98/38487, the disclosure of which is incorporated by reference herein. In another embodiment of the invention, one of the plates is held in a fixed position, and the second plate is spring-biased towards the first plate. If one or more springs are used to bias the plates towards each other, the springs should be sufficiently stiff to ensure that the plates are pressed against the flexible walls of the vessel with sufficient force to cause the walls to conform to the inner surfaces of the plates.

Figure 9:
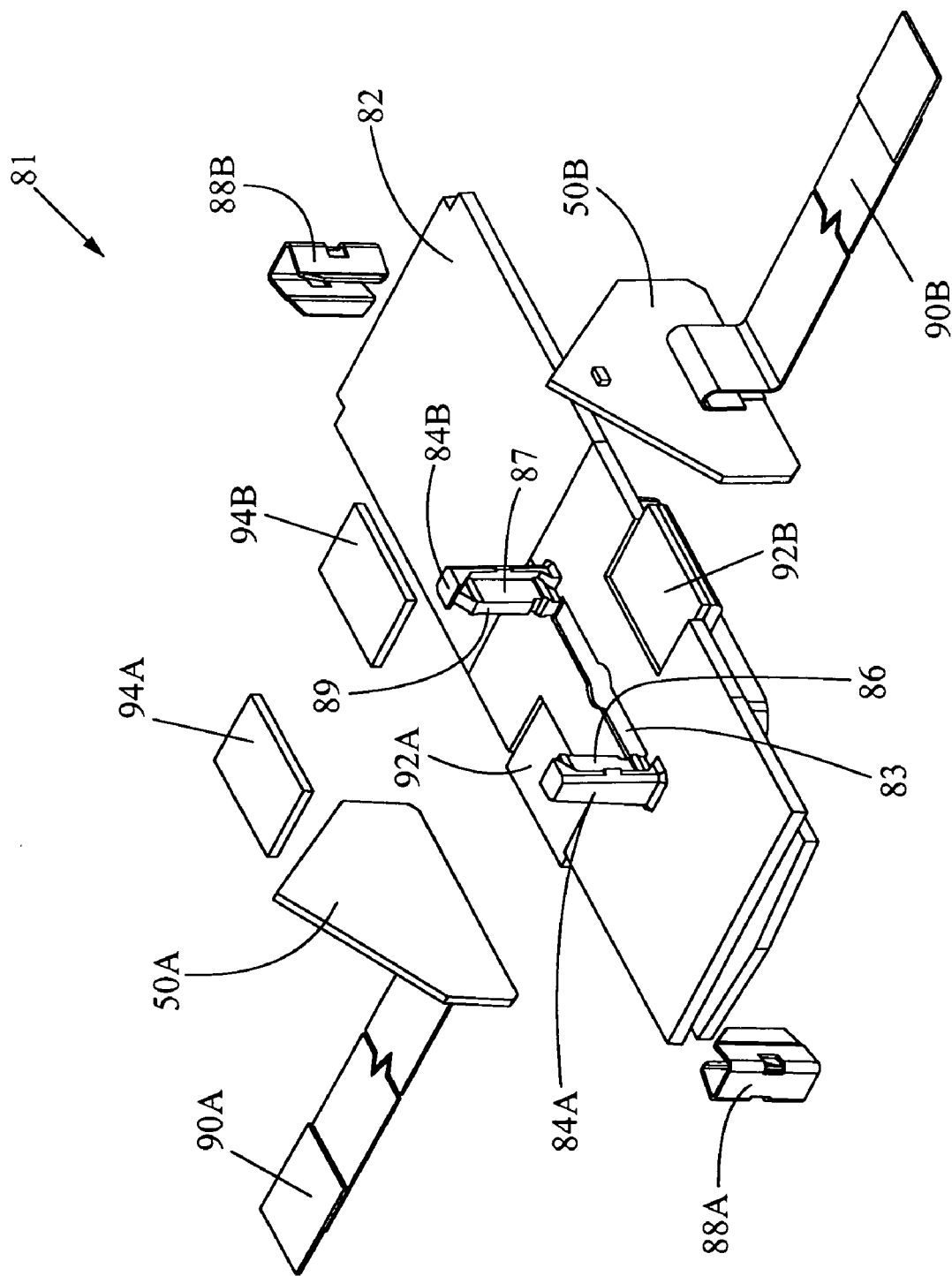
FIG. 9 is an exploded view of a support structure for holding the plates of FIG. 5.
Figure 10:
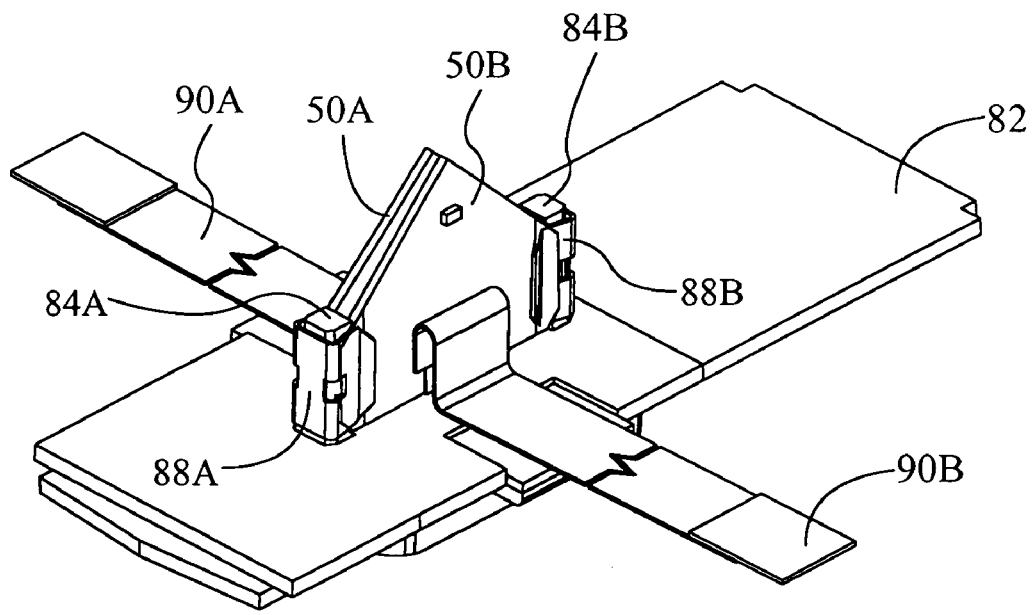
FIGS. 10-11 are assembled views of the support structure of FIG. 9.

FIGS. 9-10 illustrate a preferred support structure 81 for holding the plates 50A, 50B in an opposing relationship to each other. FIG. 9 shows an exploded view of the structure, and FIG. 10 shows an assembled view of the structure. For clarity of illustration, the support structure 81 and plates 50A, 50B are shown upside down relative to their normal orientation in the heat-exchanging module of FIG. 8. Referring to FIG. 9, the support structure 81 includes a mounting plate 82 having a slot 83 formed therein. The slot 83 is sufficiently large to enable the chamber of the vessel to be inserted through it. Spacing posts 84A, 84B extend from the mounting plate 82 on opposite sides of the slot 83. Spacing post 84A has indentations 86 formed on opposite sides thereof (only one side visible in the isometric view of FIG. 9), and spacing post 84B has indentations 87 formed on opposite sides thereof (only one side visible in the isometric view of FIG. 9). The indentations 86, 87 in the spacing posts are for receiving the edges of the plates 50A, 50B. To assemble the structure, the plates 50A, 50B are placed against opposite sides of the spacing posts 84A, 84B such that the edges of the plates are positioned in the indentations 86, 87. The edges of the plates are then held in the indentations using a suitable retention means. In the preferred embodiment, the plates are retained by retention clips 88A, 88B. Alternatively, the plates 50A, 50B may be retained by adhesive bonds, screws, bolts, clamps, or any other suitable means.

The mounting plate 82 and spacing posts 84A, 84B are preferably integrally formed as a single molded piece of plastic. The plastic should be a high temperature plastic, such as polyetherimide, which will not deform of melt when the plates 50A, 50B are heated. The retention clips 84A, 84B are preferably stainless steel. The mounting plate 82 may optionally include indentations 92A, 92B for receiving flex cables 90A, 90B, respectively, that connect the heating elements and temperature sensors disposed on the plates 50A, 50B to the PC board 76 of the heat-exchanging module 60 (FIG. 8). The portion of the flex cables 90A adjacent the plate 50A is held in the indentation 92A by a piece of tape 94A, and the portion of the flex cables 90B adjacent the plate 50B is held in the indentation 92B by a piece of tape 94B.

Figure 11:
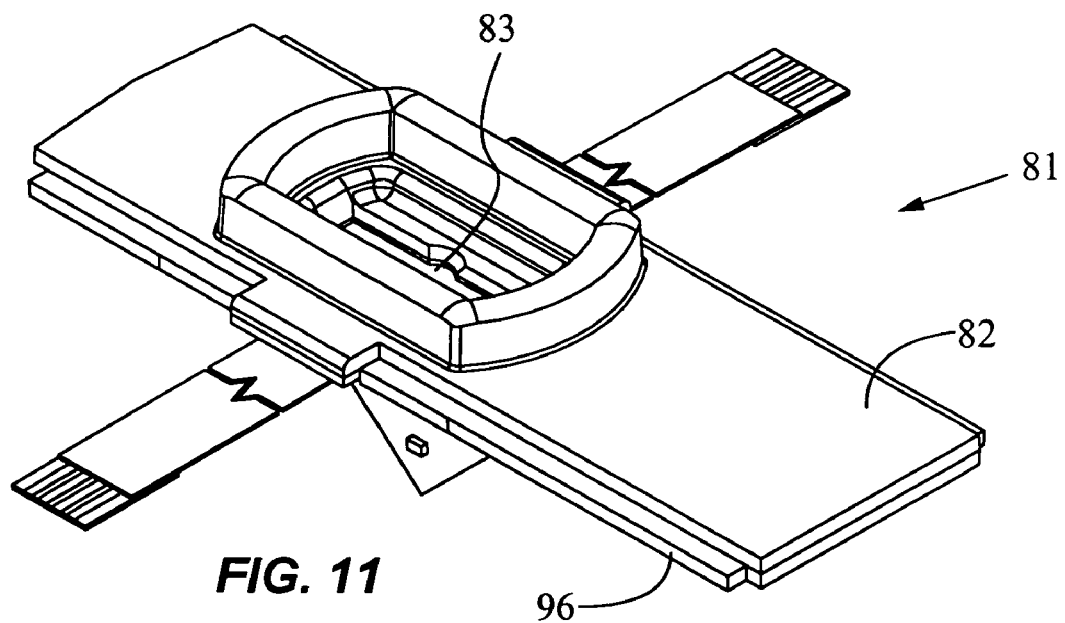

FIG. 11 is an isometric view of the assembled support structure 81. The mounting plate 82 preferably includes tabs 96 extending from opposite sides thereof for securing the structure 81 to the housing of the heat-exchanging module. Referring again to FIG. 8, the housing 62 preferably includes slots for receiving the tabs to hold the mounting plate 82 securely in place. Alternatively, the mounting plate 82 may be attached to the housing 62 using, e.g., adhesive bonding, screws, bolts, clamps, or any other conventional means of attachment.

Referring again to FIG. 9, the support structure 81 preferably holds the plates 50A, 50B so that their inner surfaces are angled very slightly towards each other. In the preferred embodiment, each of the spacing posts 84A, 84B has a wall 89 that is slightly tapered so that when the plates 50A, 50B are pressed against opposite sides of the wall, the inner surfaces of the plates are angled slightly towards each other. As best shown in FIG. 5, the inner surfaces of the plates 50A, 50B angle towards each other to form a slightly V-shaped slot into which the chamber 17 is inserted. The amount by which the inner surfaces are angled towards each other is very slight, preferably about 1° from parallel. The surfaces are angled towards each other so that, prior to the insertion of the chamber 17 between the plates 50A, 50B, the bottoms of the plates are slightly closer to each other than the tops. This slight angling of the inner surfaces enables the chamber 17 of the vessel to be inserted between the plates and withdrawn from the plates more easily. Alternatively, the inner surfaces of the plates 50A, 50B could be held parallel to each other, but insertion and removal of the vessel 12 would be more difficult.

In addition, the inner surfaces of the plates 50A, 50B are preferably spaced from each other a distance equal to the thickness of the frame 16. In embodiments in which the inner surfaces are angled towards each other, the centers of the inner surfaces are preferably spaced a distance equal to the thickness of the frame 16 and the bottoms of the plates are initially spaced a distance that is slightly less than the thickness of the frame 16. When the chamber 17 is inserted between the plates 50A, 50B, the rigid frame 16 forces the bottom portions of the plates apart so that the chamber 17 is firmly sandwiched between the plates. The distance that the plates 50A, 50B are wedged apart by the frame 16 is usually very small, e.g., about 0.035 mm if the thickness of the frame is 1 mm and the inner surfaces are angled towards each other by 1°.

Referring again to FIG. 10, the retention clips 88A, 88B should be sufficiently flexible to accommodate this slight outward movement of the plates 50A, 50B, yet sufficiently stiff to hold the plates within the recesses in the spacing posts 84A, 84B during insertion and removal of the vessel. The wedging of the vessel between the plates 50A, 50B provides an initial preload against the chamber and ensures that the flexible major walls of the chamber, when pressurized, establish good thermal contact with the inner surfaces of the plates.

Figure 13:
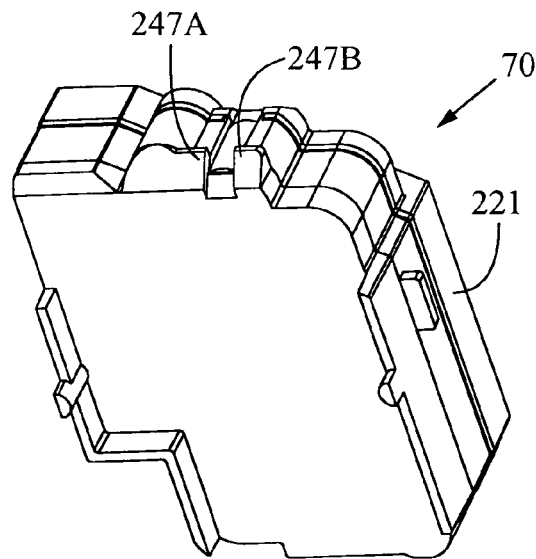
FIG. 13 is an isometric view showing the exterior of one the optics assemblies of FIG. 8.
Figure 14:
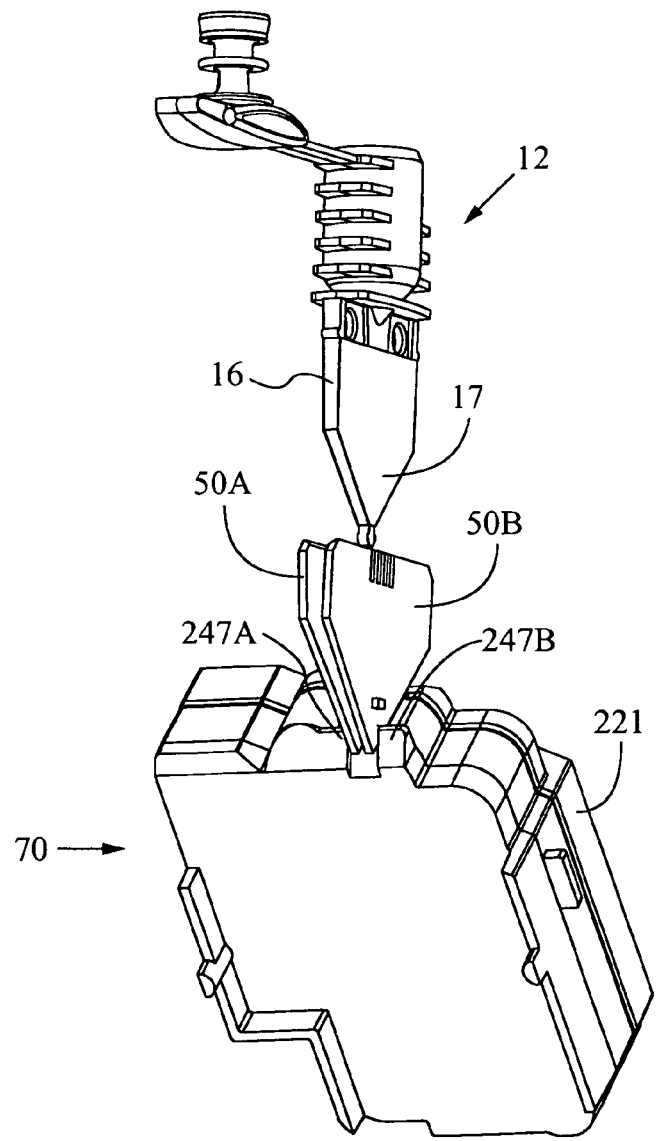
FIG. 14 is an isometric view of the optics assembly of FIG. 13, the plates of FIG. 5 in contact with the optics assembly, and the vessel of FIG. 1 positioned above the plates.

Referring again to FIG. 8, to limit the amount that the plates 50 can spread apart due to the pressurization of the vessel 12, stops may be molded into the housings of optics assemblies 68, 70. As shown in FIG. 13, the housing 221 of the optics assembly 70 includes claw-like stops 247A, 247B that extend outwardly from the housing. As shown in FIG. 14, the housing 221 is positioned such that the bottom edges of the plates 50A, 50B are inserted between the stops 247A, 247B. The stops 247A, 247B thus prevent the plates 50A, 50B from spreading farther than a predetermined maximum distance from each other. Although not shown in FIG. 14 for illustrative clarity, the optics assembly 68 (see FIG. 8) has a housing with corresponding stops for preventing the other halves of the plates from spreading farther than the predetermined maximum distance from each other. Referring again to FIG. 14, the maximum distance that stops 247A, 247B permit the inner surfaces of the plates 50A, 50B to be spaced from each other should closely match the thickness of the frame 16. Preferably, the maximum spacing of the inner surfaces of the plates 50A, 50B is slightly larger than the thickness of the frame 16 to accommodate tolerance variations in the vessel 12 and plates 50A, 50B. For example, the maximum spacing is preferably about 0.1 to 0.3 mm greater than the thickness of the frame 16.

Figure 15A:
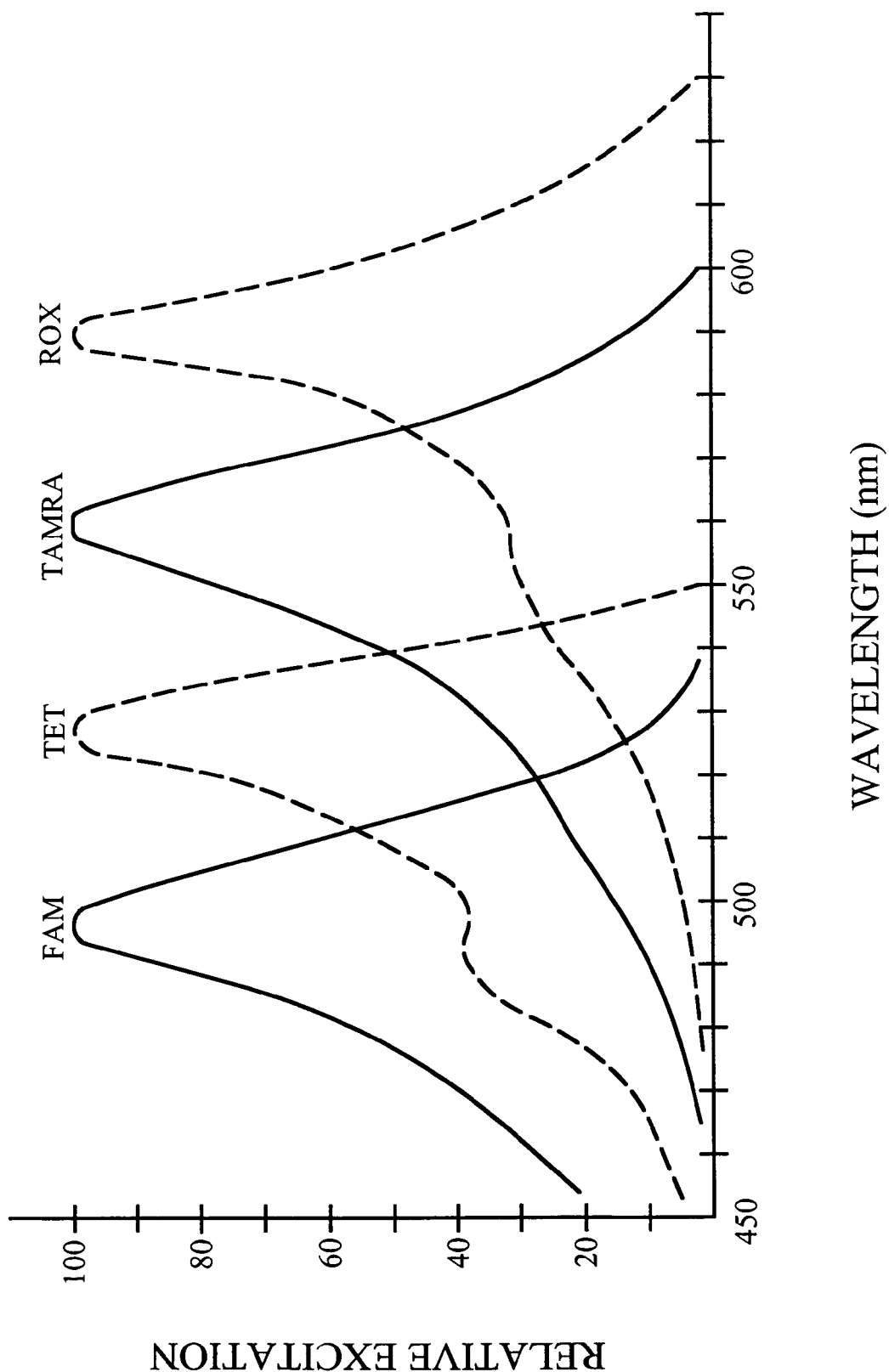
FIGS. 15A and 15B are graphs showing the excitation and emission spectra, respectively, of four dyes often used in thermal reactions.
Figure 15B:
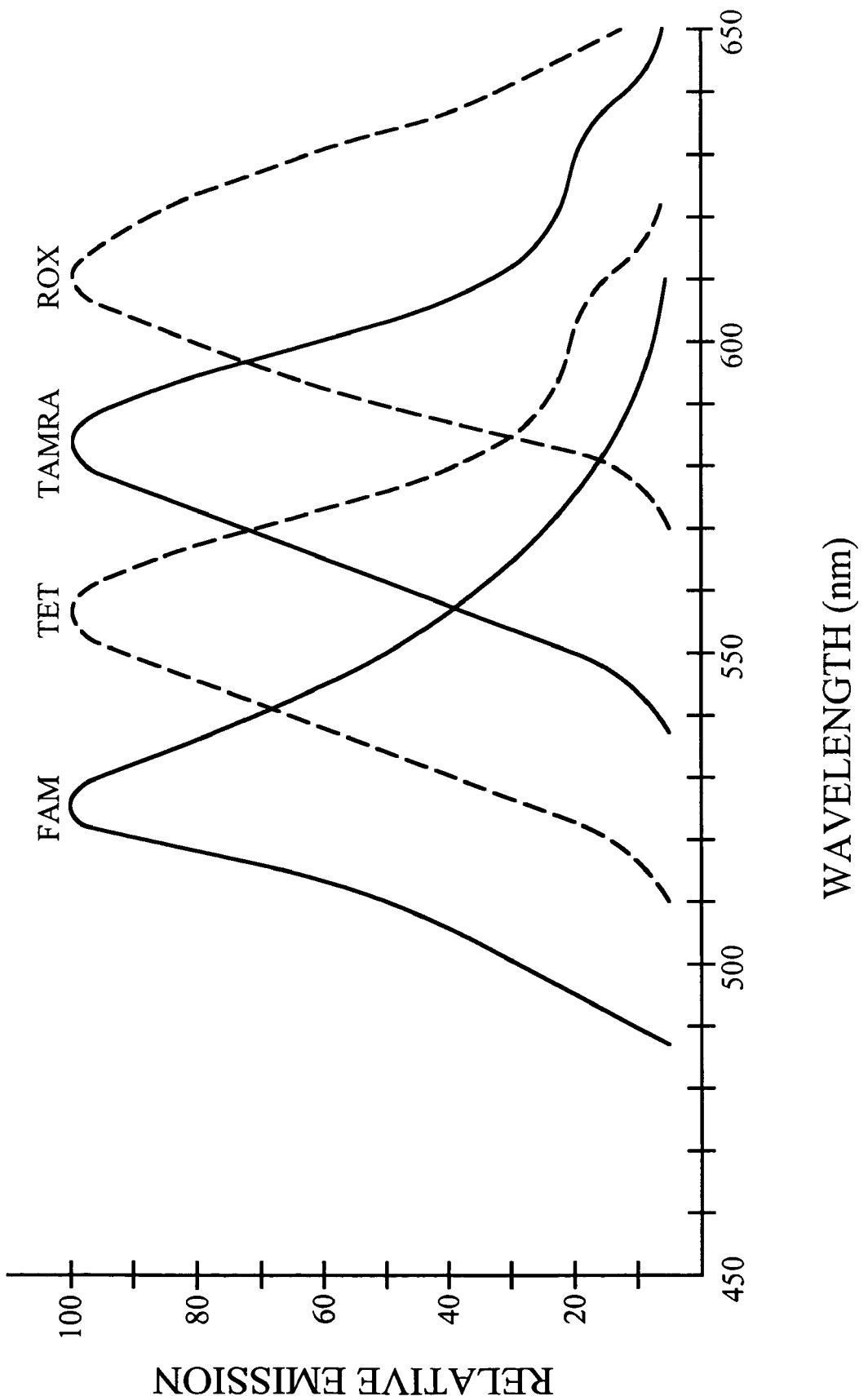

FIGS. 15A and 15B show the fluorescent excitation and emission spectra, respectively, of four fluorescent dyes of interest. These dyes are standard fluorescent dyes used with the TaqMan® chemistry (available from the Perkin-Elmer Corporation, Foster City, Calif.) and are well known by their acronyms FAM, TET, TAMRA, and ROX. Although the preferred embodiment is described with reference to these four dyes, it is to be understood that the apparatus of the present invention is not limited to these particular dyes or to the TaqMang® chemistry. The apparatus may be used with any fluorescent dyes or with interculating dyes such as SYBRGreen™ or ethidium bromide. Such dyes are commercially available from various well known suppliers. Fluorescent dyes and labeling chemistries for labeling analytes in a reaction mixture are well known in the art and need not be discussed further herein. Further, although fluorescence detection is presently preferred, the apparatus of the present invention is not limited to detection based upon fluorescent labels. The apparatus may be applicable to detection based upon phosphorescent labels, chemiluminescent labels, or electrochemiluminescent labels.

As shown in FIG. 15A, the excitation spectra curves for FAM, TET, TAMRA, and ROX are typically very broad at the base, but sharper at the peaks. As shown in FIG. 15B, the relative emission spectra curves for the same dyes are also very broad at the base and sharper at the peaks. Thus, these dyes have strongly overlapping characteristics in both their excitation and emission spectra. The overlapping characteristics have traditionally made it difficult to distinguish the fluorescent signal of one dye from another when multiple dyes are used to label different analytes in a reaction mixture.

Figure 15C:
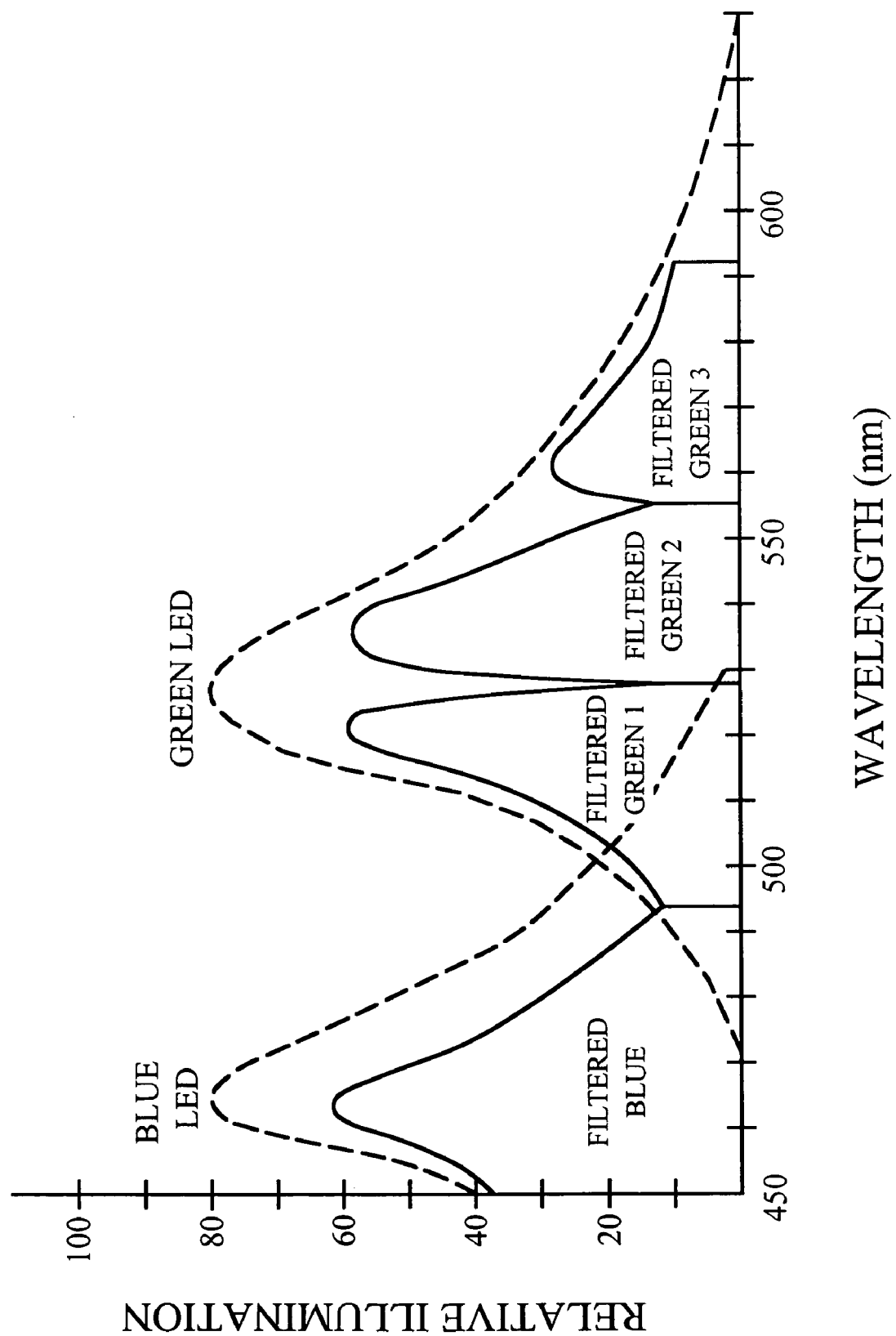
FIG. 15C shows the effects of filtering the outputs of green and blue LEDs to provide distinct excitation wavelength ranges.

According to the present invention, multiple light sources are used to provide excitation beams to the dyes in multiple excitation wavelength ranges. Each light source provides excitation light in a wavelength range matched to the peak excitation range of a respective one of the dyes. In the preferred embodiment, the light sources are blue and green LEDs. FIG. 15C shows the effects of filtering the outputs of blue and green LEDs to provide substantially distinct excitation wavelength ranges. Typical blue and green LEDs have substantial overlap in the range of around 480 nm through 530 nm. By the filtering regime of the present invention, the blue LED light is filtered to a range of about 450 nm to 495 nm to match the relative excitation peak for FAM. The green LED light is filtered to a first range of 495 to 527 nm corresponding to the excitation peak for TET, a second range of 527 to 555 nm corresponding to the excitation peak for TAMRA, and a third range of 555 to 593 nm corresponding to the excitation peak for ROX.

Figure 15D:
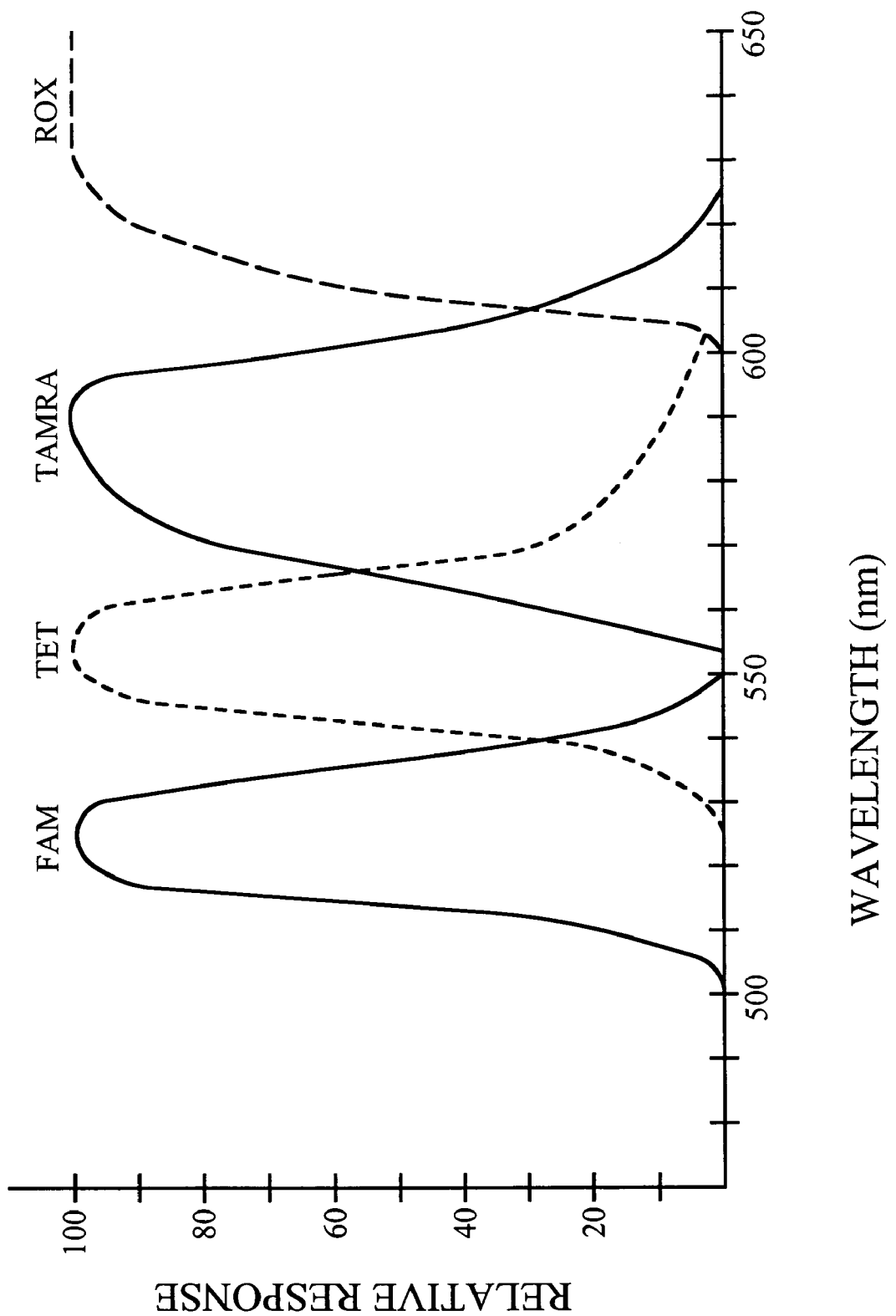
FIG. 15D shows the effects of filtering light emitted from each of the four dyes of FIGS. 15A-B to form distinct emission wavelength ranges.

FIG. 15D shows the effects of filtering light emitted (fluorescent emission) from each of the four dyes to form distinct emission wavelength ranges. As shown previously in FIG. 15B, the fluorescent emissions of the dyes before filtering are spherically diffuse with overlapping spectral bandwidths, making it difficult to distinguish the fluorescent output of one dye from another. As shown in FIG. 15D, by filtering the fluorescent emissions of the dyes into substantially distinct wavelength ranges, a series of relatively narrow peaks (detection windows) are obtained, making it possible to distinguish the fluorescent outputs of different dyes, thus enabling the detection of a number of different fluorescently-labeled analytes in a reaction mixture.

Figure 16:
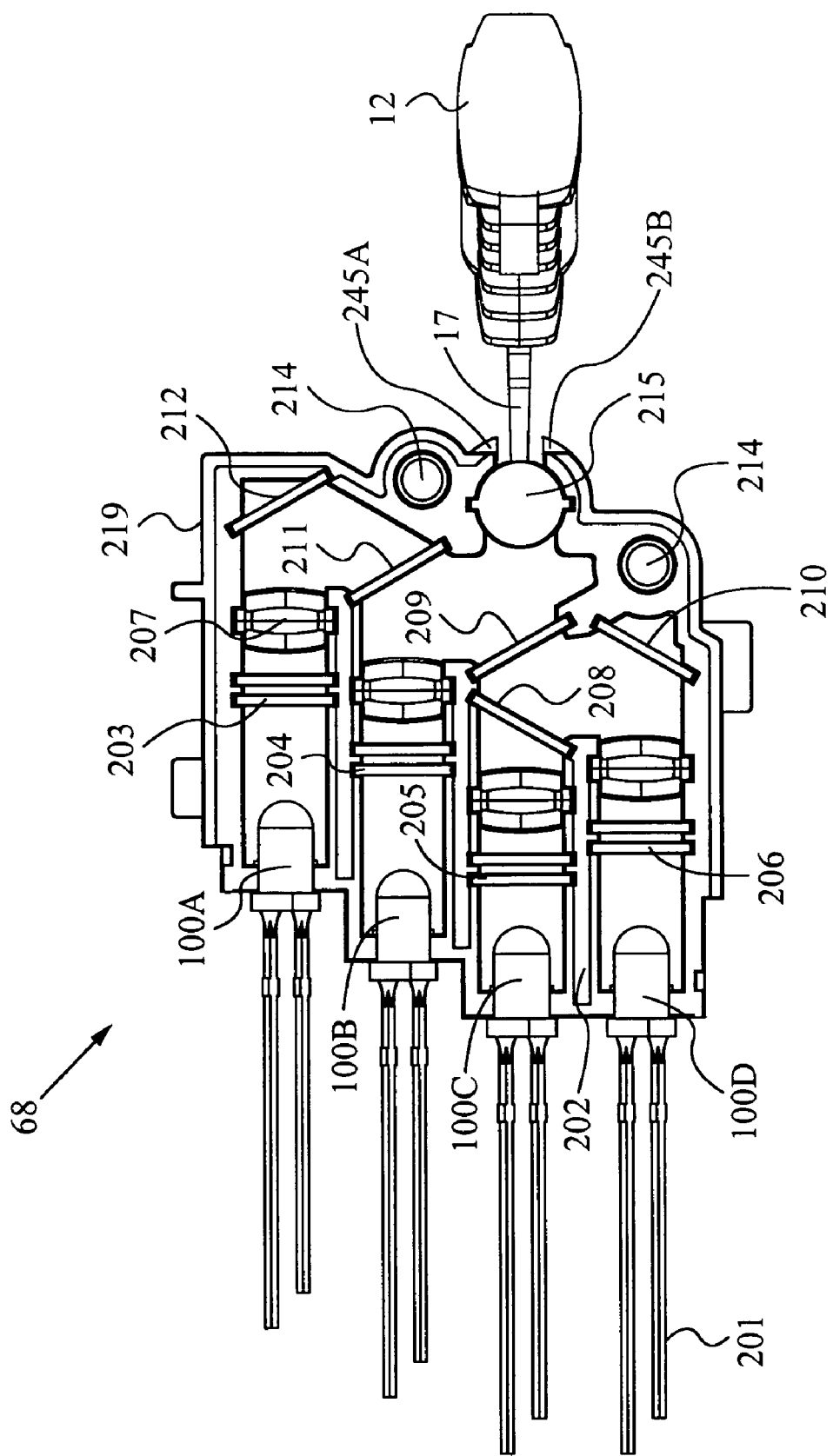
FIG. 16 is a plan view of an optical excitation assembly of the module of FIG. 8.
Figure 17:
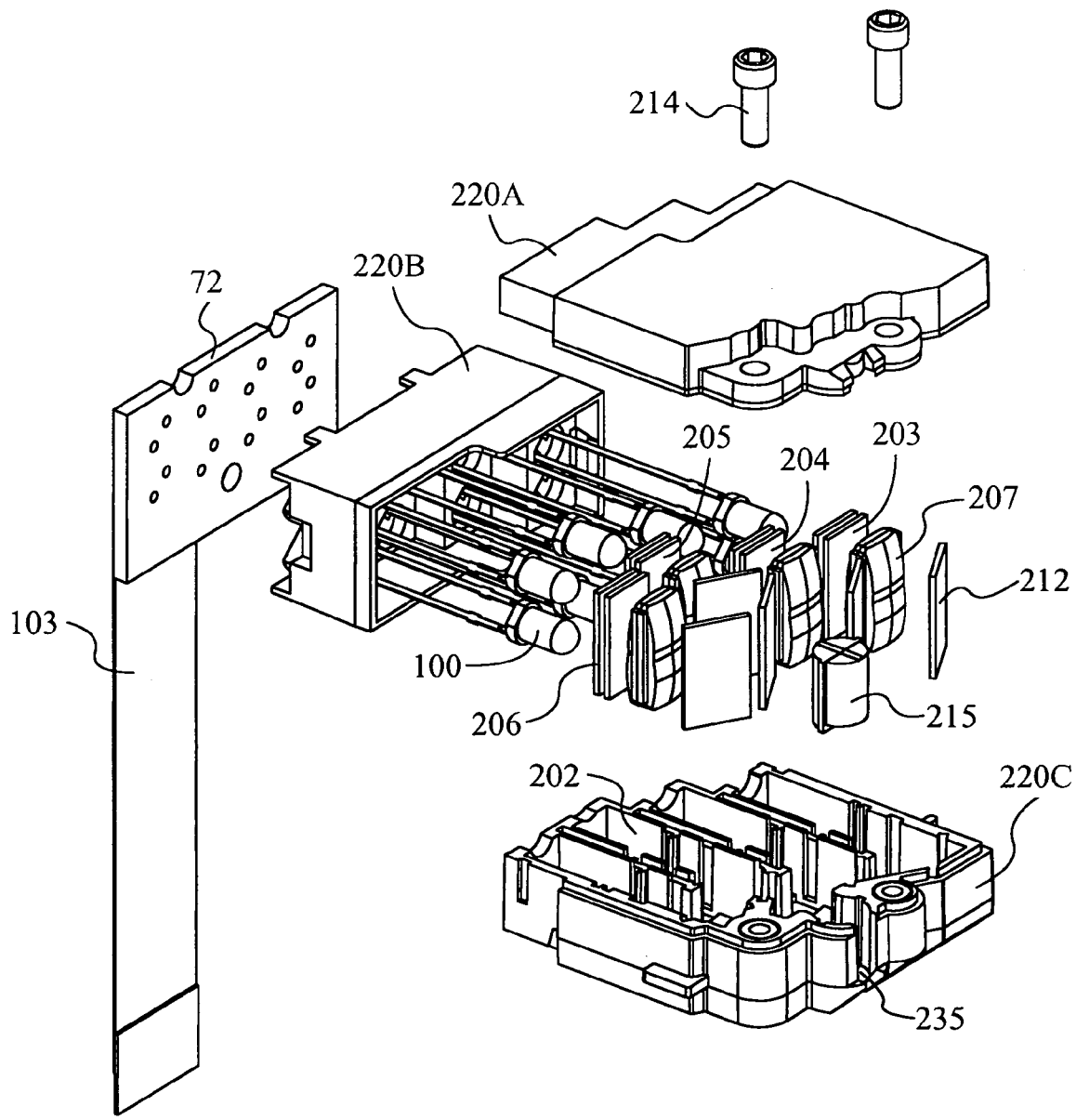
FIG. 17 is an exploded view of the excitation assembly of FIG. 16.

FIG. 16 is a schematic, plan view of the optical excitation assembly 68. The assembly 68 is positioned adjacent the reaction vessel 12 to transmit excitation beams to the reaction mixture contained in the chamber 17. FIG. 17 is an exploded view of the excitation assembly. As shown in FIGS. 16-17, the excitation assembly 68 includes a housing 219 for holding various components of the assembly. The housing 219 includes stops 245A, 245B for limiting the maximum spacing of the thermal plates, as previously discussed with reference to FIGS. 8 and 14. The housing 219 preferably comprises one or more molded pieces of plastic. In the preferred embodiment, the housing 219 is a multi-part housing comprised of three housing elements 220A, 220B, and 220C. The upper and lower housing elements 220A and 220C are preferably complementary pieces that couple together and snap-fit into housing element 220B. In this embodiment, the housing elements 220A and 220C are held together by screws 214. In alternative embodiments, the entire housing 219 may be a one-piece housing that holds a slide-in optics package.

The lower housing element 220C includes an optical window 235 into which is placed a cylindrical rod lens 215 for focusing excitation beams into the chamber 17. In general, the optical window 235 may simply comprise an opening in the housing through which excitation beams may be transmitted to the chamber 17. The optical window may optionally include an optically transmissive or transparent piece of glass or plastic serving as a window pane, or as in the preferred embodiment, a lens for focusing excitation beams. The lens 215 preferably directly contacts one of the optically transmissive side walls of the chamber 17.

The optics assembly 68 also includes four light sources, preferably LEDs 100A, 100B, 100C, and 100D, for transmitting excitation beams through the lens 215 to the reaction mixture contained in the chamber 17. In general, each light source may comprise a laser, a light bulb, or an LED. In the preferred embodiment, each light source comprises a pair of directional LEDs. In particular, the four light sources shown in FIGS. 16-17 are preferably a first pair of green LEDs 100A, a second pair of green LEDs 100B, a pair of blue LEDs 100C, and a third pair of green LEDs 100D. The LEDs receive power through leads 201 which are connected to a power source (not shown in FIGS. 16-17). The LEDs are mounted to the optical circuit board 72 which is attached to the back of the housing element 220B so that the LEDs are rigidly fixed in the housing. The optical circuit board 72 is connected to the main PC board of the heat-exchanging module (shown in FIG. 8) via the flex cable 103.

The optics assembly 68 further includes a set of filters and lenses arranged in the housing 219 for filtering the excitation beams generated by the LEDs so that each of the beams transmitted to the chamber 17 has a distinct excitation wavelength range. As shown in FIG. 17, the lower housing element 220C preferably includes walls 202 that create separate excitation channels in the housing to reduce potential cross-talk between the different pairs of LEDs. The walls 202 preferably include slots for receiving and rigidly holding the filters and lenses. The filters and lenses may also be fixed in the housing by means of an adhesive used alone, or more preferably, with an adhesive used in combination with slots in the housing.

Referring to FIG. 16, the filters in the optics assembly 68 may be selected to provide excitation beams to the reaction mixture in the chamber 17 in any desired excitation wavelength ranges. The optics assembly 68 may therefore be used with any fluorescent, phosphorescent, chemiluminescent, or electrochemiluminescent labels of interest. For purposes of illustration, one specific embodiment of the assembly 68 will now be described in which the assembly is designed to provide excitation beams corresponding to the peak excitation wavelength ranges FAM, TAMRA, TET, and ROX.

In this embodiment, a pair of 593 nm low pass filters 203 are positioned in front of green LEDs 100A, a pair of 555 nm low pass filters 204 are positioned in front of green LEDs 100B, a pair of 495 nm low pass filters 205 are positioned in front of blue LEDs 100C, and a pair of 527 nm low pass filters 206 are positioned in front of green LEDs 100D. Although it is presently preferred to position a pair of low pass filters in front of each pair of LEDs for double filtering of excitation beams, a single filter may be used in alternative embodiments. In addition, a lens 207 is preferably positioned in front of each pair of filters for collimating the filtered excitation beams. The optics assembly 68 also includes a 495 nm high pass reflector 208, a 527 nm high pass reflector 209, a mirror 210, a 555 nm low pass reflector 211, and a 593 nm low pass reflector 212. The reflecting filters and mirrors 208-212 are angularly offset by 30° from the low pass filters 203-206.

The excitation assembly 68 transmits excitation beams to the chamber 17 in four distinct excitation wavelength ranges as follows. When the green LEDs 100A are activated, they generate an excitation beam that passes through the pair of 593 nm low pass filters 203 and through the lens 207. The excitation beam then reflects off of the 593 nm low pass reflector 212, passes through the 555 nm low pass reflector 211, reflects off of the 527 nm high pass reflector 209, and passes through the lens 215 into the reaction chamber 17.

The excitation beam from the LEDs 100A is thus filtered to a wavelength range of 555 to 593 nm corresponding to the peak excitation range for ROX. When the green LEDs 100B are activated, they generate an excitation beam that passes through the pair of 555 nm low pass filters 204, reflects off of the 555 nm low pass reflector 211, reflects off of the 527 nm high pass reflector 209, and passes through the lens 215 into the reaction chamber 17. The excitation beam from LEDs 100B is thus filtered to a wavelength range of 527 to 555 nm corresponding to the peak excitation range for TAMRA.

When the blue LEDs 100C are activated, they generate an excitation beam that passes through the pair of 495 nm low pass filters 205, through the 495 µm high pass reflector 208, through the 527 nm high pass reflector 209, and through the lens 215 into the reaction chamber 17. The excitation beam from LEDs 100C is thus filtered to a wavelength below 495 nm corresponding to the peak excitation range for FAM. When the green LEDs 100D are activated, they generate an excitation beam that passes through the pair of 527 nm low pass filters 206, reflects off of the mirror 210, reflects off of the 495 nm high pass reflector 208, passes through the 527 nm high pass reflector 209, and passes through the lens 215 into the reaction chamber 17. The excitation beam from LEDs 100D is thus filtered to a wavelength range of 495 to 527 nm corresponding to the peak excitation range for TET. In operation, the LEDs 100A, 100B, 100C, 100D are sequentially activated to excite the different fluorescent labels contained in the chamber 17 with excitation beams in substantially distinct wavelength ranges.

Figure 18:
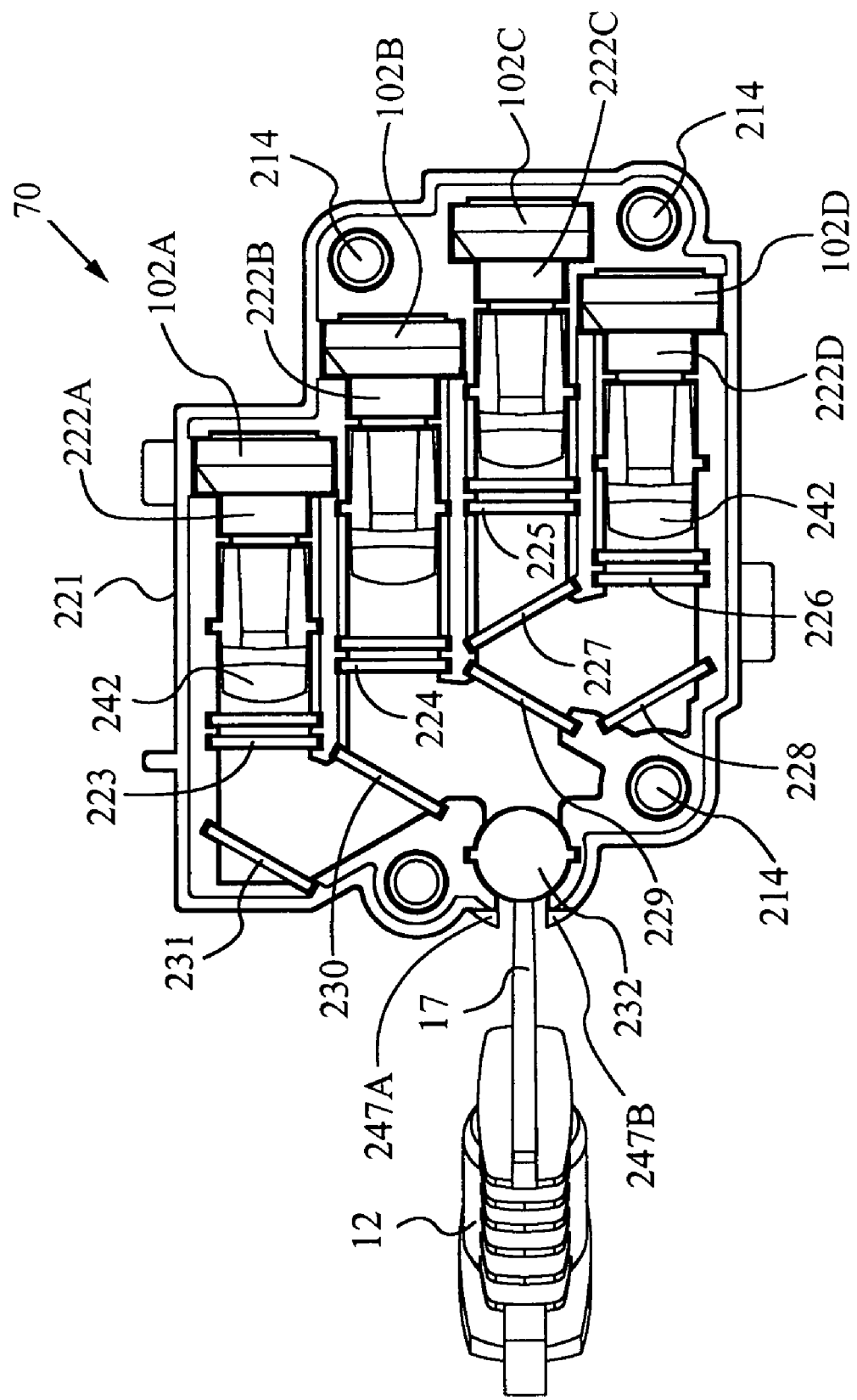
FIG. 18 is a plan view of an optical detection assembly of the module of FIG. 8.
Figure 19:
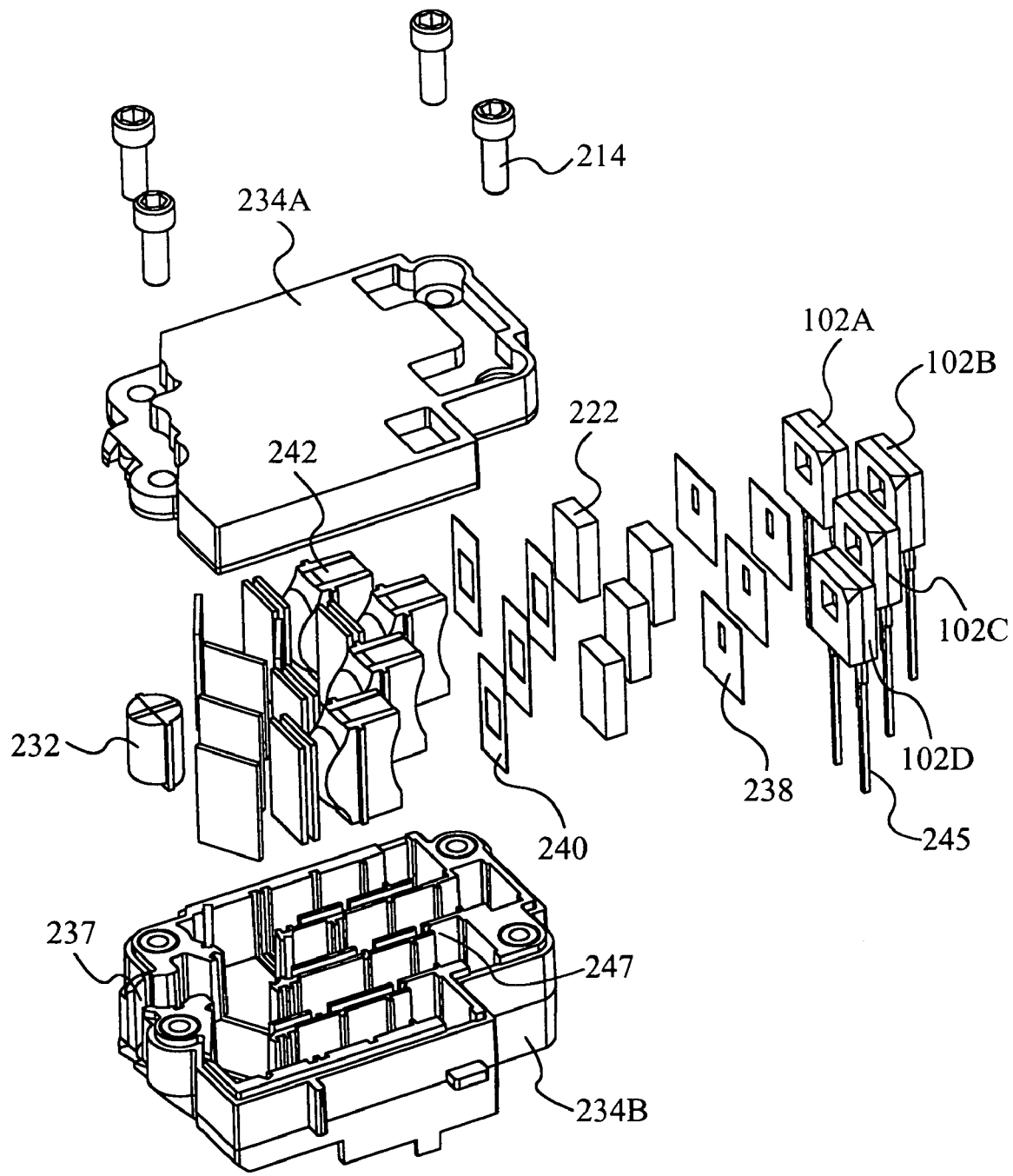
FIG. 19 is an exploded view of the detection assembly of FIG. 18.

FIG. 18 is a schematic, plan view of the optical detection assembly 70. The assembly 70 is positioned adjacent the reaction vessel 12 to receive light emitted from the chamber 17. FIG. 19 is an exploded view of the detection assembly 70. As shown in FIGS. 18-19, the assembly 70 includes a housing 221 for holding various components of the assembly.

The housing 221 includes the stops 247A, 247B previously described with reference to FIGS. 13-14. The housing 221 preferably comprises one or more molded plastic pieces. In the preferred embodiment, the housing 221 is a multi-part housing comprised of upper and lower housing elements 234A and 234B. The housing elements 234A, 234B are complementary, mating pieces that are held together by screws 214. In alternative embodiments, the entire housing 221 may be a one-piece housing that holds a slide-in optics package.

The lower housing element 234B includes an optical window 237 into which is placed a cylindrical rod lens 232 for collimating light emitted from the chamber 17. In general, the optical window may simply comprise an opening in the housing through which the emitted light may be received. The optical window may optionally include an optically transmissive or transparent piece of glass or plastic serving as a window pane, or as in the preferred embodiment, the lens 232 for collimating light emitted from the chamber 17. The lens 232 preferably directly contacts one of the optically transmissive side walls of the chamber 17.

The optics assembly 70 also includes four detectors 102A, 102B. 102C, and 102D for detecting light emitted from the chamber 17 that is received through the lens 232. In general, each detector may be a photomultiplier tube, CCD, photodiode, or other known detector. In the preferred embodiment, each detector is a PIN photodiode. The detectors 102A, 102B. 102C, and 102D are preferably rigidly fixed in recesses formed in the lower housing element 234B. The detectors are electrically connected by leads 245 to the optical circuit board 74 (see FIG. 8) which is preferably mounted to the underside of the lower housing element 234B.

The optics assembly 70 further includes a set of filters and lenses arranged in the housing 221 for separating light emitted from the chamber 17 into different emission wavelength ranges and for directing the light in each of the emission wavelength ranges to a respective one of the detectors. As shown in FIG. 19, the lower housing element 234B preferably includes walls 247 that create separate detection channels in the housing, with one of the detectors positioned at the end of each channel. The walls 247 preferably include slots for receiving and rigidly holding the filters and lenses. The filters and lenses may also be rigidly fixed in the housing 221 by an adhesive used alone, or more preferably, with an adhesive used in combination with slots in the housing.

Referring to FIG. 18, the filters in the optics assembly 70 may be selected to block light emitted from the chamber 17 outside of any desired emission wavelength ranges. The optics assembly 70 may therefore be used with any fluorescent, phosphorescent, chemiluminescent, or electrochemiluminescent labels of interest. For purposes of illustration, one specific embodiment of the assembly 70 will now be described in which the assembly is designed to detect light emitted from the chamber 17 in the peak emission wavelength ranges of FAM, TAMRA, TET, and ROX.

In this embodiment, the set of filters preferably includes a 515 nm Schott Glass® filter 222A positioned in front of the first detector 102A, a 550 nm Schott Glass® filter 222B positioned in front of the second detector 102B, a 570 nm Schott Glass® filter 222C positioned in front of the third detector 102C, and a 620 nm Schott Glass® filter 222D positioned in front of the fourth detector 102D. These Schott Glass® filters are commercially available from Schott Glass Technologies, Inc. of Duryea, Pa. The optics assembly 70 also includes a pair of 505 nm high pass filters 223 positioned in front of the first detector 102A, a pair of 537 nm high pass filters 224 positioned in front of the second detector 102B, a pair of 565 nm high pass filters 225 positioned in front of the third detector 102C, and a pair of 605 nm high pass filters 226 positioned in front of the fourth detector 102D.

Although it is presently preferred to position a pair of high pass filters in front of each detector for double filtering of light, a single filter may be used in alternative embodiments. In addition, a lens 242 is preferably positioned in each detection channel between the pair of high pass filters and the Schott Glass® filter for collimating the filtered light. The optics assembly 70 further includes a 605 nm high pass reflector 227, a mirror 228, a 565 nm low pass reflector 229, a 537 nm high pass reflector 230, and a 505 nm high pass reflector 231. The reflecting filters and mirrors 227-231 are preferably angularly offset by 30° from the high pass filters 223-226. As shown in FIG. 19, the detection assembly 70 also preferably includes a first aperture 238 positioned between each detector and Schott Glass® filter 222 and an aperture 240 positioned between each lens 242 and Schott Glass® filter 222. The apertures 238, 240 reduce the amount of stray or off-axis light that reaches the detectors 102A, 102B, 102C, and 102D.

Referring again to FIG. 18, the detection assembly 70 detects light emitted from the chamber 17 in four emission wavelength ranges as follows. The emitted light passes through the lens 232 and strikes the 565 nm low pass reflector 229. The portion of the light having a wavelength in the range of about 505 to 537 nm (corresponding to the peak emission wavelength range of FAM) reflects from the 565 nm low pass reflector 229, passes through the 537 nm high pass reflector 230, reflects from the 505 nm high pass reflector 231, passes through the pair of 505 nm high pass filters 223, through the lens 242, through the 515 nm Schott Glass® filter 222A, and is detected by the first detector 102A. Meanwhile, the portion of the light having a wavelength in the range of about 537 to 565 nm (corresponding to the peak emission wavelength range of TET) reflects from the 565 nm low pass reflector 229, reflects from the 537 nm high pass reflector 230, passes through the pair of 537 nm high pass filters 224, through the lens 242, through the 550 nm Schott Glass® filter 222B, and is detected by the second detector 102B.

Further, the portion of the light having a wavelength in the range of about 565 to 605 nm (corresponding to the peak emission wavelength range of TAMRA) passes through the 565 nm low pass reflector 229, through the 605 nm high pass reflector 227, through the pair of 565 nm high pass filters 225, through the lens 242, through the 570 nm Schott Glass® filter 222C, and is detected by the third detector 102C. The portion of the light having a wavelength over 605 nm (corresponding to the peak emission wavelength range of ROX) passes through the 565 nm low pass reflector 229, reflects from the 605 nm high pass reflector 227, reflects from the mirror 228, passes through the pair of 605 nm high pass filters 226, through the lens 242, through the 620 nm Schott Glass® filter 222D, and is detected by the fourth detector 102D. In operation, the outputs of detectors 102A, 102B, 102C, and 102D are analyzed to determine the concentrations of each of the different fluorescently-labeled analytes contained in the chamber 17, as will be described in greater detail below.

Figure 20:
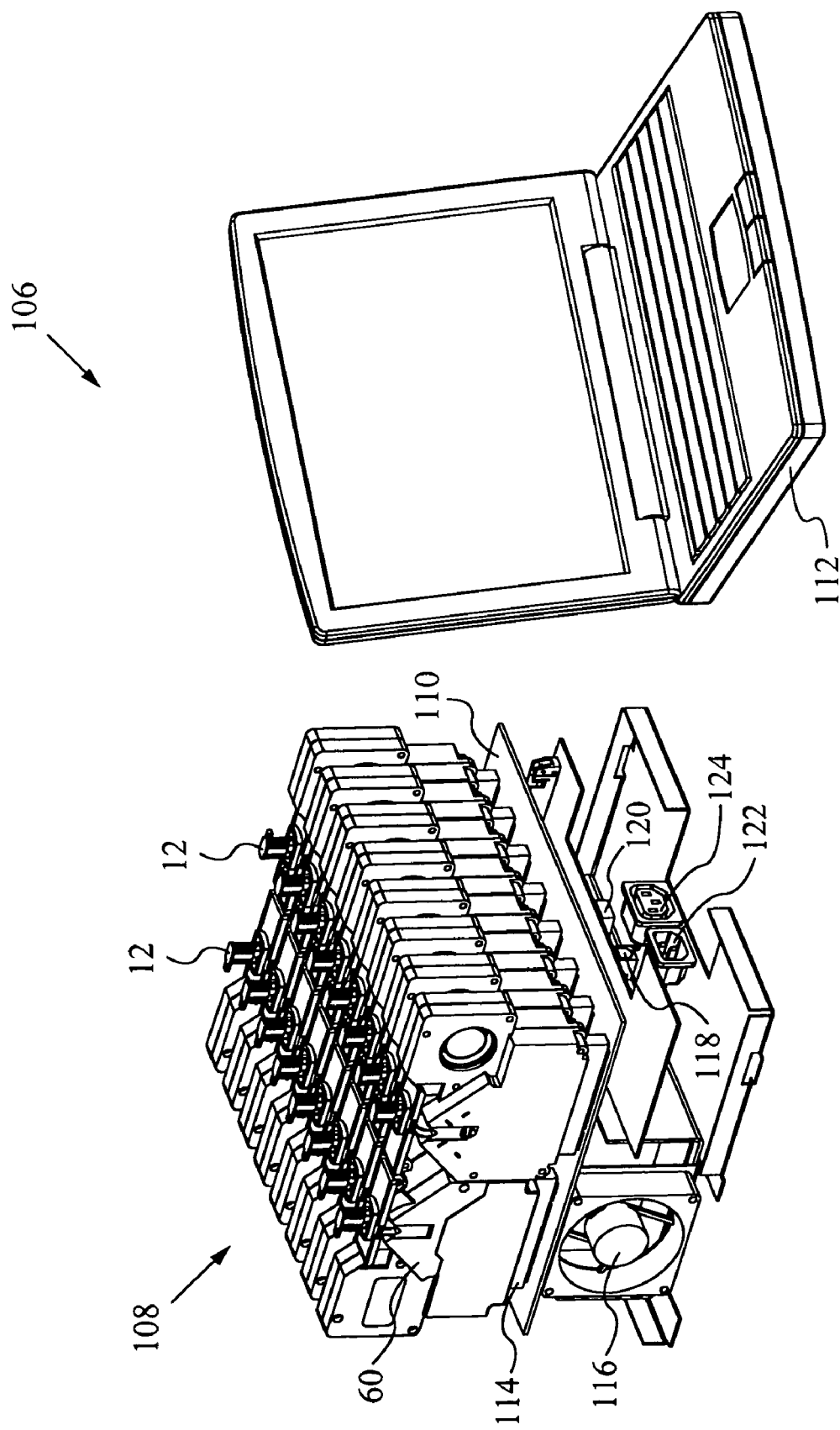
FIG. 20 is an isometric view of a multi-site reactor system according to the present invention.
Figure 21:
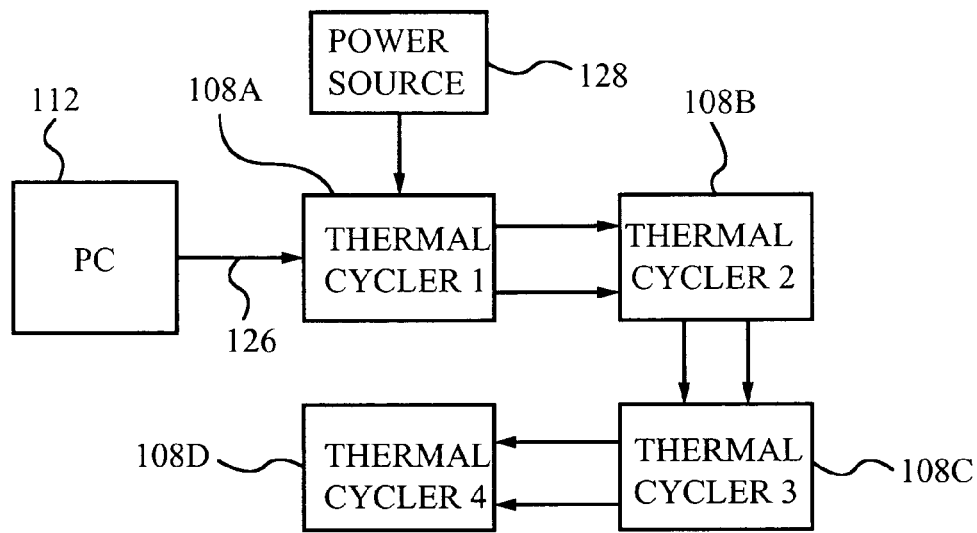
FIG. 21 is a schematic, block diagram of another multi-site reactor system having multiple thermal cycling instruments daisy-chained to a computer and a power source.

FIG. 20 shows a multi-site reactor system 106 according to the present invention. The reactor system 106 comprises a thermal cycler 108 and a controller 112, such as a personal or network computer. The thermal cycler 108 includes a base instrument 110 for receiving multiple heat-exchanging modules 60 (previously described with reference to FIG. 8). The base instrument 110 has a main logic board with edge connectors 114 for establishing electrical connections to the modules 60. The base instrument 110 also preferably includes a fan 116 for cooling its electronic components. The base instrument 110 may be connected to the controller 112 using any suitable data connection, such as a universal serial bus (USB), ethernet connection, or serial line. It is presently preferred to use a USB that connects to the serial port of controller 112. Alternatively, the controller may be built into the base instrument 110.

The term "thermal cycling" is herein intended to mean at least one change of temperature, i.e. increase or decrease of temperature, in a reaction mixture. Therefore, samples undergoing thermal cycling may shift from one temperature to another and then stabilize at that temperature, transition to a second temperature or return to the starting temperature. The temperature cycle may be performed only once or may be repeated as many times as required to study or complete the particular chemical reaction of interest. Due to space limitations in patent drawings, the thermal cycler 108 shown in FIG. 20 includes only sixteen reaction sites provided by the sixteen heat-exchanging modules 60 arranged in two rows of eight modules each. It is to be understood, however, that the thermal cycler can include any number of desired reaction sites, i.e., it can be configured as a multi-hundred site instrument for simultaneously processing hundreds of samples. Alternatively, it may be configured as a small, hand held, battery-operated instrument having, e.g., 1 to 4 reaction sites.

Each of the reaction sites in the thermal cycler 108 is provided by a respective one of the heat-exchanging modules 60. The modules 60 are preferably independently controllable so that different chemical reactions can be run simultaneously in the thermal cycler 108. The thermal cycler 108 is prefer- ably modular so that each heat-exchanging module 60 can be individually removed from the base instrument 110 for servicing, repair, or replacement. This modularity reduces downtime since all the modules 60 are not off line to repair one, and the instrument 110 can be upgraded and enlarged to add more modules as needed. The modularity of the thermal cycler 108 also means that individual modules 60 can be precisely calibrated, and module-specific schedules or corrections can be included in the control programs, e.g., as a series of module-specific calibration or adjustment charts.

In embodiments in which the base instrument 110 operates on external power, e.g. 110 V AC, the instrument preferably includes two power connections 122, 124. Power is received though the first connection 122 and output through the second connection 124. Similarly, the instrument 110 preferably includes network interface inlet and outlet ports 118, 120 for receiving a data connection through inlet port 118 and outputting data to another base instrument through outlet port 120. As shown in the block diagram of FIG. 21, this arrangement permits multiple thermal cyclers 108A, 108B, 108C, 108D to be daisy-chained from one controller 112 and one external power source 128.

Figure 22:
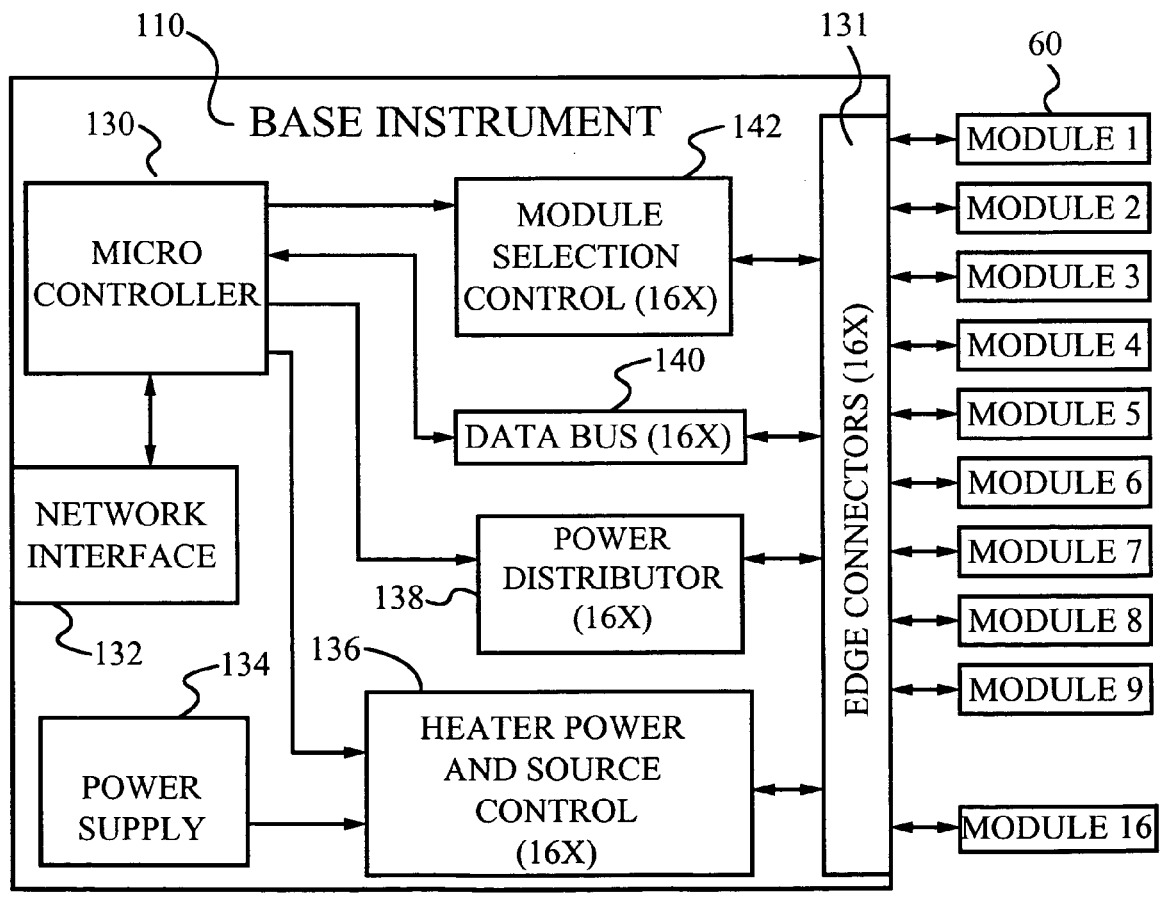
FIG. 22 is a schematic, block diagram of a base instrument of the system of FIG. 20.

FIG. 22 is a schematic, block diagram of the base instrument 110. The base instrument includes a power supply 134 for supplying power to the instrument and to each module 60. The power supply 134 may comprise an AC/DC converter for receiving power from an external source and converting it to direct current, e.g., for receiving 110V AC and converting it to 12V DC. Alternatively, the power supply 134 may comprise a battery, e.g., a 12V battery. The base instrument 110 also includes a microprocessor or microcontroller 130 containing firmware for controlling the operation of the base instrument 110 and modules 60. The microcontroller 130 communicates through a network interface 132 to the controller computer via a USB. Due to current limitations of processing power, it is currently preferred to include at least one microcontroller in the base instrument per sixteen modules 60. Thus if the base instrument has a thirty-two module capacity, at least two microcontrollers should be installed in the instrument 110 to control the modules.

The base instrument 110 further includes a heater power source and control circuit 136, a power distributor 138, a data bus 140, and a module selection control circuit 142. Due to space limitations in patent drawings, control circuit 136, power distributor 138, data bus 140, and control circuit 142 are shown only once in the block diagram of FIG. 22. However, the base instrument 110 actually contains one set of these four functional components 136, 138, 140, 142 for each heat-exchanging module 60. Thus, in the embodiment of FIG. 22, the base instrument 110 includes sixteen control circuits 136, power distributors 138, data buses 140, and control circuits 142. Similarly, the base instrument 110 also includes a different edge connector 131 for connecting to each of the modules 60, so that the instrument includes sixteen edge connectors for the embodiment shown in FIG. 22. The edge connectors are preferably 120 pin card edge connectors that provide cableless connection from the base instrument 110 to each of the modules 60. Each control circuit 136, power distributor 138, data bus 140, and control circuit 142 is connected to a respective one of the edge connectors and to the microcontroller 130.

Each heater power and source control circuit 136 is a power regulator for regulating the amount of power supplied to the heating element(s) of a respective one of the modules 60. The source control circuit 136 is preferably a DC/DC converter that receives a +12V input from the power supply 134 and outputs a variable voltage between 0 and −24V. The voltage is varied in accordance with signals received from the microcontroller 130. Each power distributor 138 provides −5 v, +5V, +12V, and GND to a respective module 60. The power distributor thus supplies power for the electronic components of the module. Each data bus 140 provides parallel and serial connections between the microcontroller 130 and the digital devices of a respective one of the modules 60. Each module selection controller 94 allows the microcontroller 130 to address an individual module 60 in order to read or write control or status information.

Figure 23:
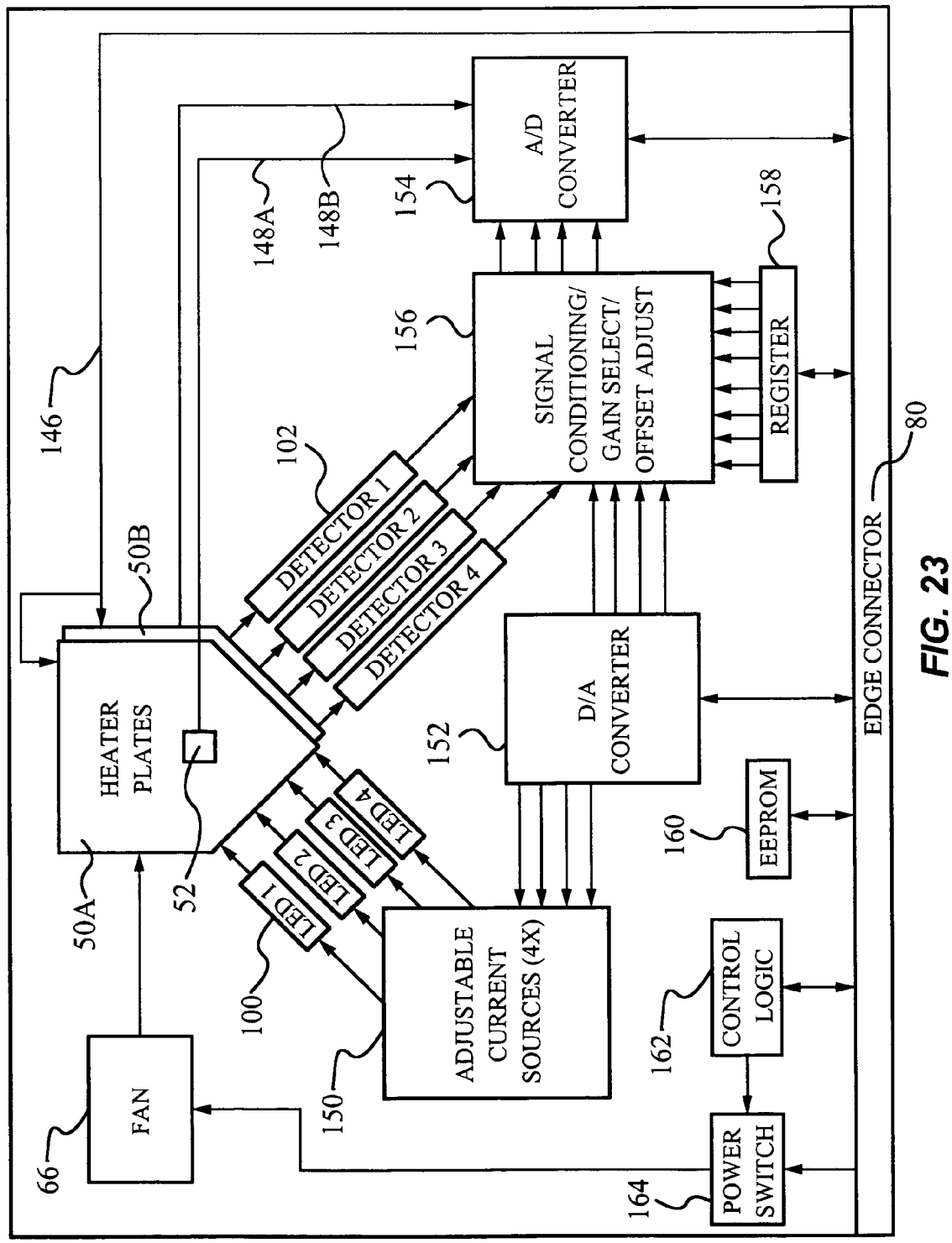
FIG. 23 is a schematic, block diagram of the electronic components of the module of FIG. 8.

FIG. 23 is a schematic, block diagram of the electronic components of a heat-exchanging module 60. Each module includes an edge connector 80 for cableless connection to a corresponding edge connector of the base instrument. The module also includes heater plates 50A, 50B each having a resistive heating element as described above. The plates 50A, 50B are wired in parallel to receive power input 146 from the base instrument. The plates 50A, 50B also include temperature sensors 52, e.g. thermistors, that output analog temperature signals to an analog-to-digital converter 154. The converter 154 converts the analog signals to digital signals and routes them to the microcontroller in the base instrument through the edge connector 80. The heat-exchanging module also includes a cooling system, such as a fan 66, for cooling the plates 50A, 50B. The fan 66 receives power from the base instrument and is activated by switching a power switch 164. The power switch 164 is in turn controlled by a control logic block 162 that receives control signals from the microcontroller in the base instrument.

The module further includes four light sources, such as LEDs 100, for excitation of labeled analytes in the reaction mixture and four detectors 102, preferably photodiodes, for detecting fluorescent emissions from the reaction mixture. The module also includes an adjustable current source 150 for supplying a variable amount of current (e.g., in the range of 0 to 30 mA) to each LED to vary the brightness of the LED. A digital-to-analog converter 152 is connected between the adjustable current source 150 and the microcontroller of the base instrument to permit the microcontroller to adjust the current source digitally. The adjustable current source 150 may be used to ensure that each LED has about the same brightness when activated. Due to manufacturing variances, many LEDs have different brightnesses when provided with the same amount of current. The brightness of each LED may be tested during manufacture of the heat-exchanging module and calibration data stored in a memory 160 of the module. The calibration data indicates the correct amount of current to provide to each LED. The microcontroller reads the calibration data from the memory 160 and controls the current source 150 accordingly. The microcontroller may also control the current source 150 to adjust the brightness of the LEDs 100 in response to optical feedback received from the detectors 102.

The module additionally includes a signal conditioning/gain select/offset adjust block 156 comprised of amplifiers, switches, electronic filters, and a digital-to-analog converter. The block 156 adjusts the signals from the detectors 102 to increase gain, offset, and reduce noise. The microcontroller in the base instrument controls block 156 through a digital output register 158. The output register 158 receives data from the microcontroller and outputs control voltages to the block 156. The block 156 outputs the adjusted detector signals to the microcontroller through the analog-to-digital converter 154 and the edge connector 80. The module also includes the memory 160, preferably a serial EEPROM, for storing data specific to the module, such as calibration data for the LEDs 100, thermal plates 50A, 50B, and temperature sensors 52, as well as calibration data for a deconvolution algorithm described in detail below.

Referring again to FIG. 20, the reactor system 106 may be configured for manual filling and pressurization of each reaction vessel 12 by a human operator. Manual use of the system is suitable for lower throughput embodiments. For higher throughput embodiments, however, the system 106 preferably includes automated machinery, e.g., a pick-and-place machine, for filling and pressurizing each of the vessels 12.

Figure 24:
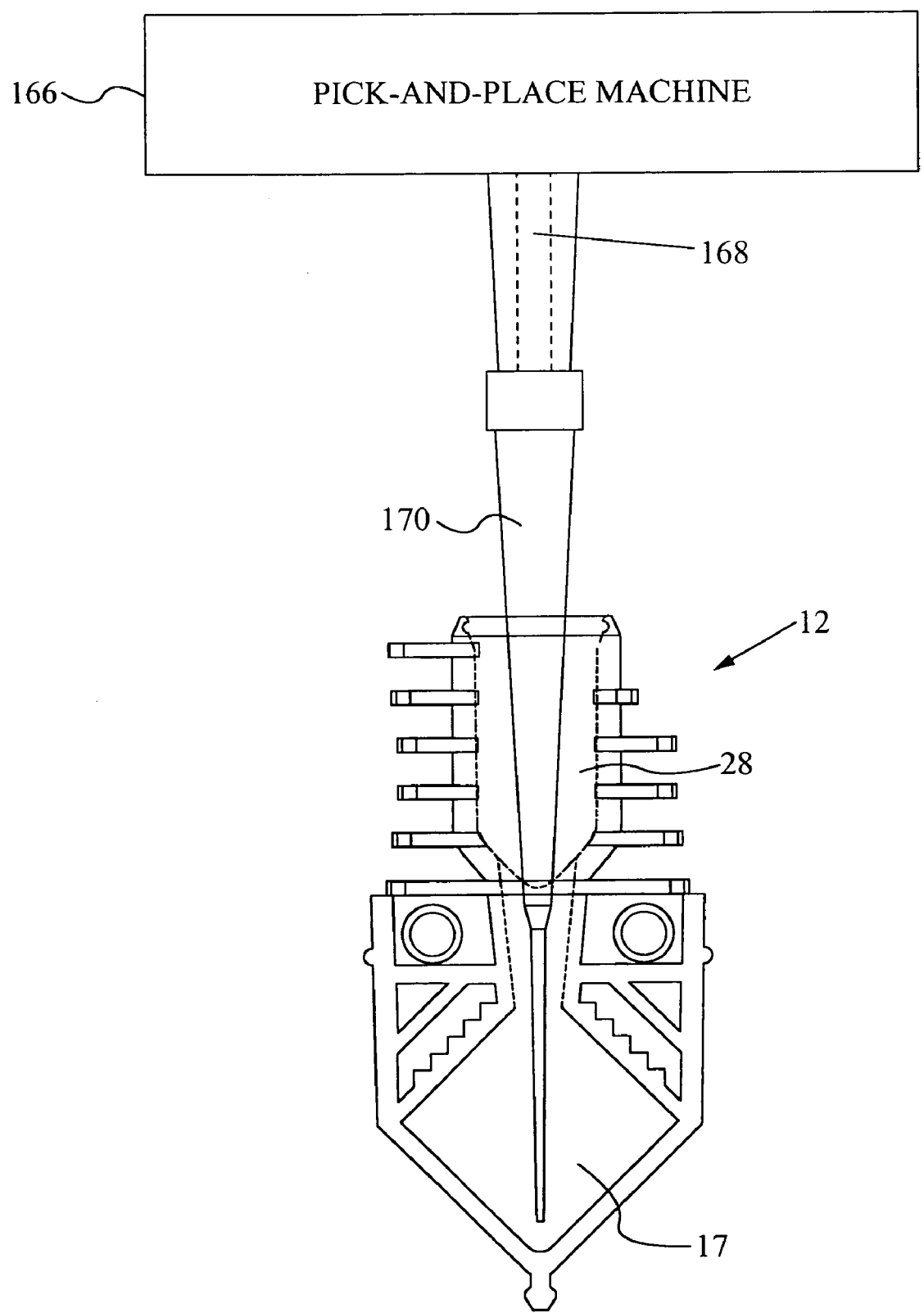
FIG. 24 is a schematic diagram of a pick-and-place machine having a pipette for filling the reaction vessel of FIG. 1.

FIG. 24 shows a schematic diagram of a pick-and-place machine 166 for automatically filling and pressurizing a reaction vessel 12. The machine 166 has a pipette head 168 for engaging a disposable pipette tip 170. The machine 166 also has controllable vacuum and pressure sources in communication with the pipette head 168 for aspirating and dispensing fluids using the pipette tip 170. The vacuum and pressure sources may comprise, e.g., one or more syringe pumps, compressed air sources, pneumatic pumps, vacuum pumps, or connections to external sources of pressure.

Figure 25:
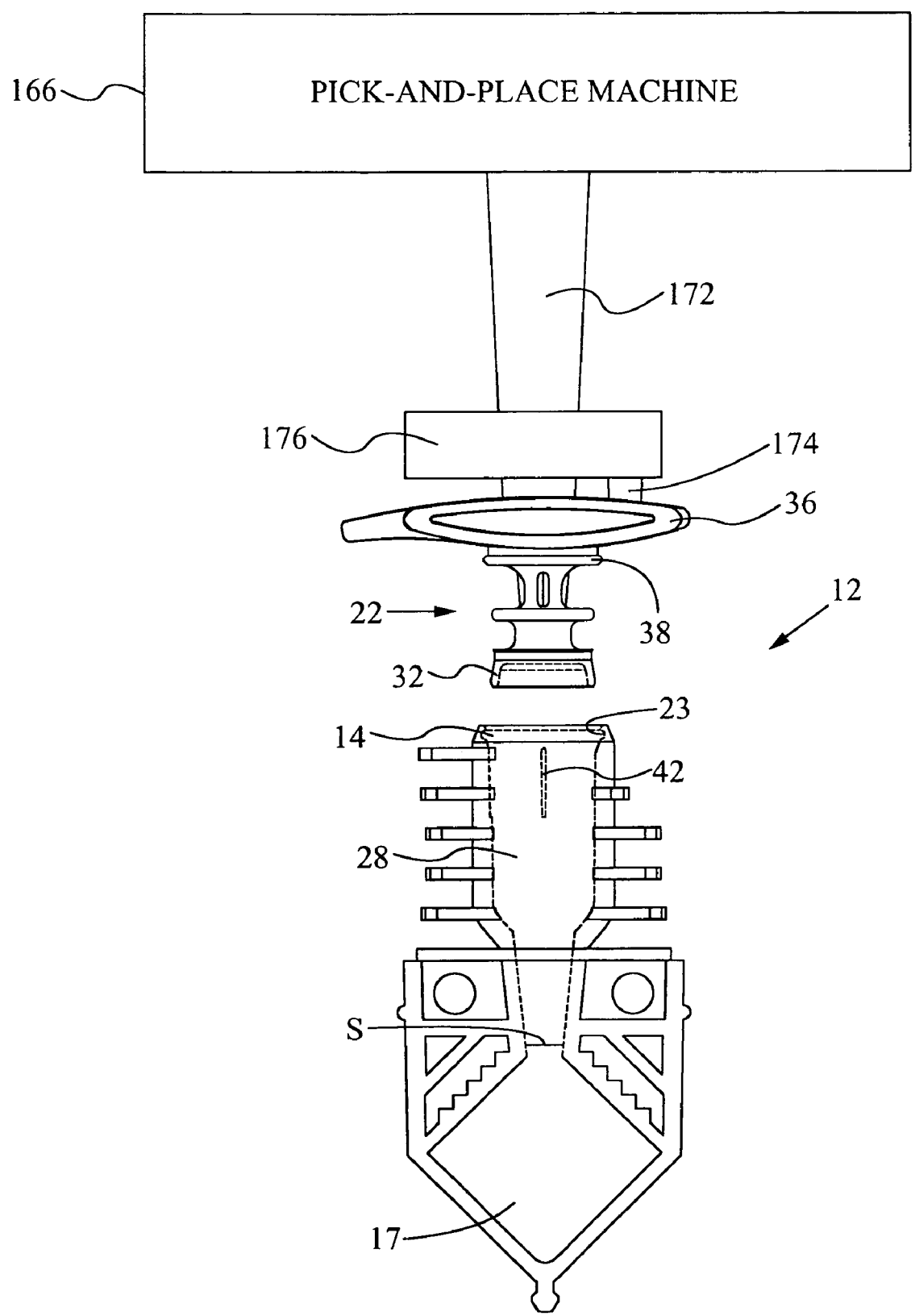
FIG. 25 is a schematic diagram of the pick-and-place machine of FIG. 24 inserting a plunger into the vessel of FIG. 1.
Figure 26:
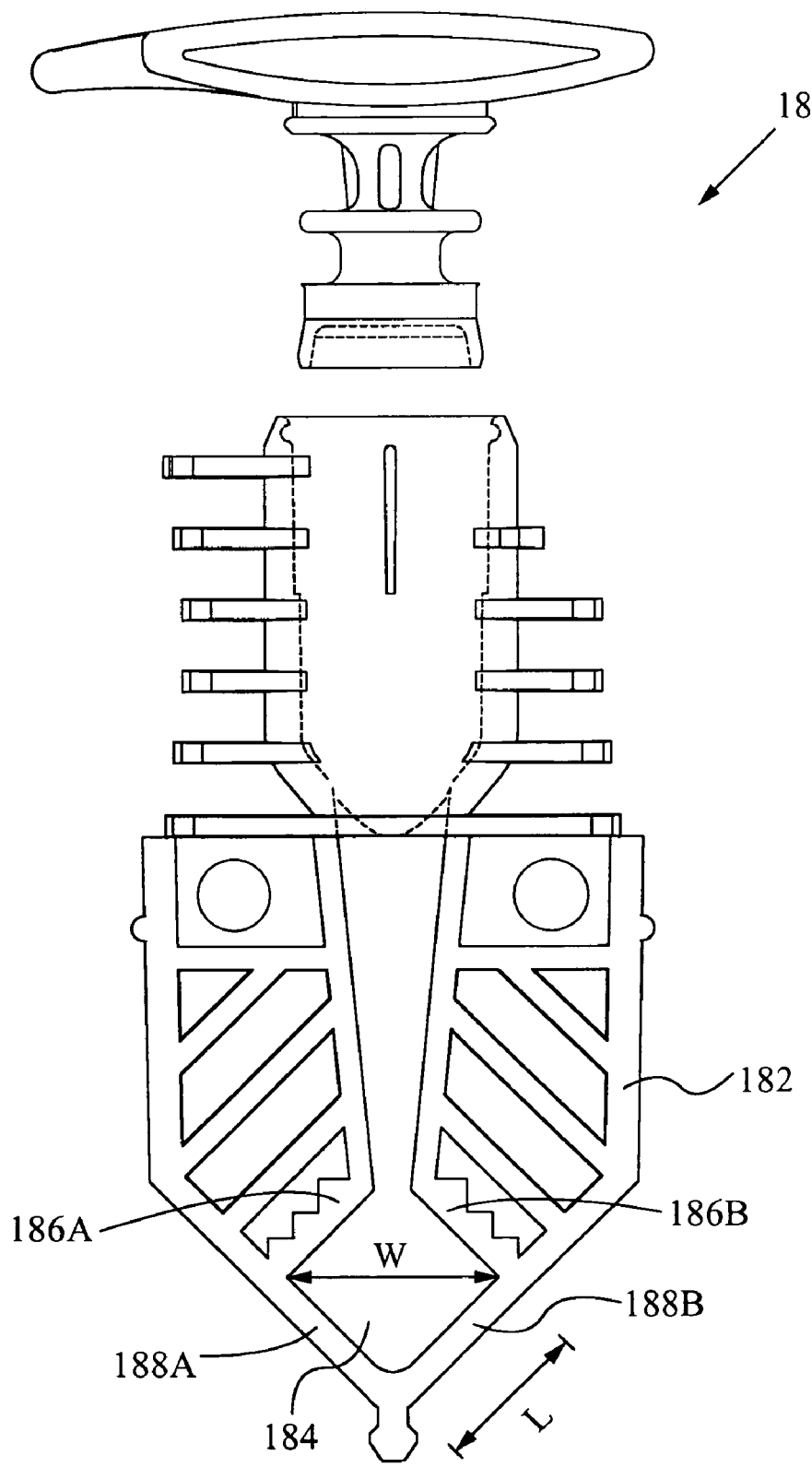
FIG. 26 is a schematic, front view of a reaction vessel according to another embodiment of the invention.
Figure 27:
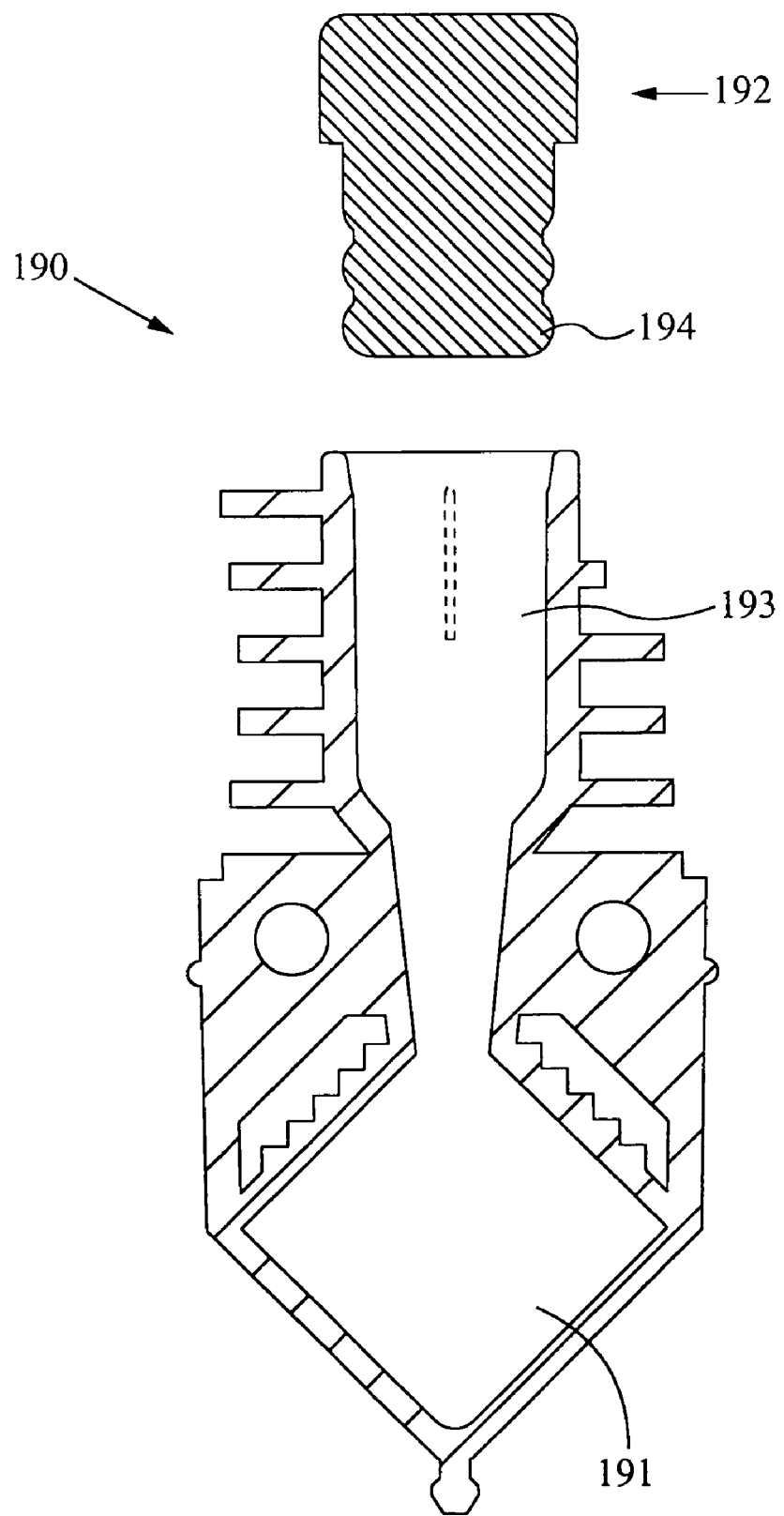
FIG. 27 is a schematic, cross sectional view of a reaction vessel according to an alternative embodiment of the invention.
Figure 28:
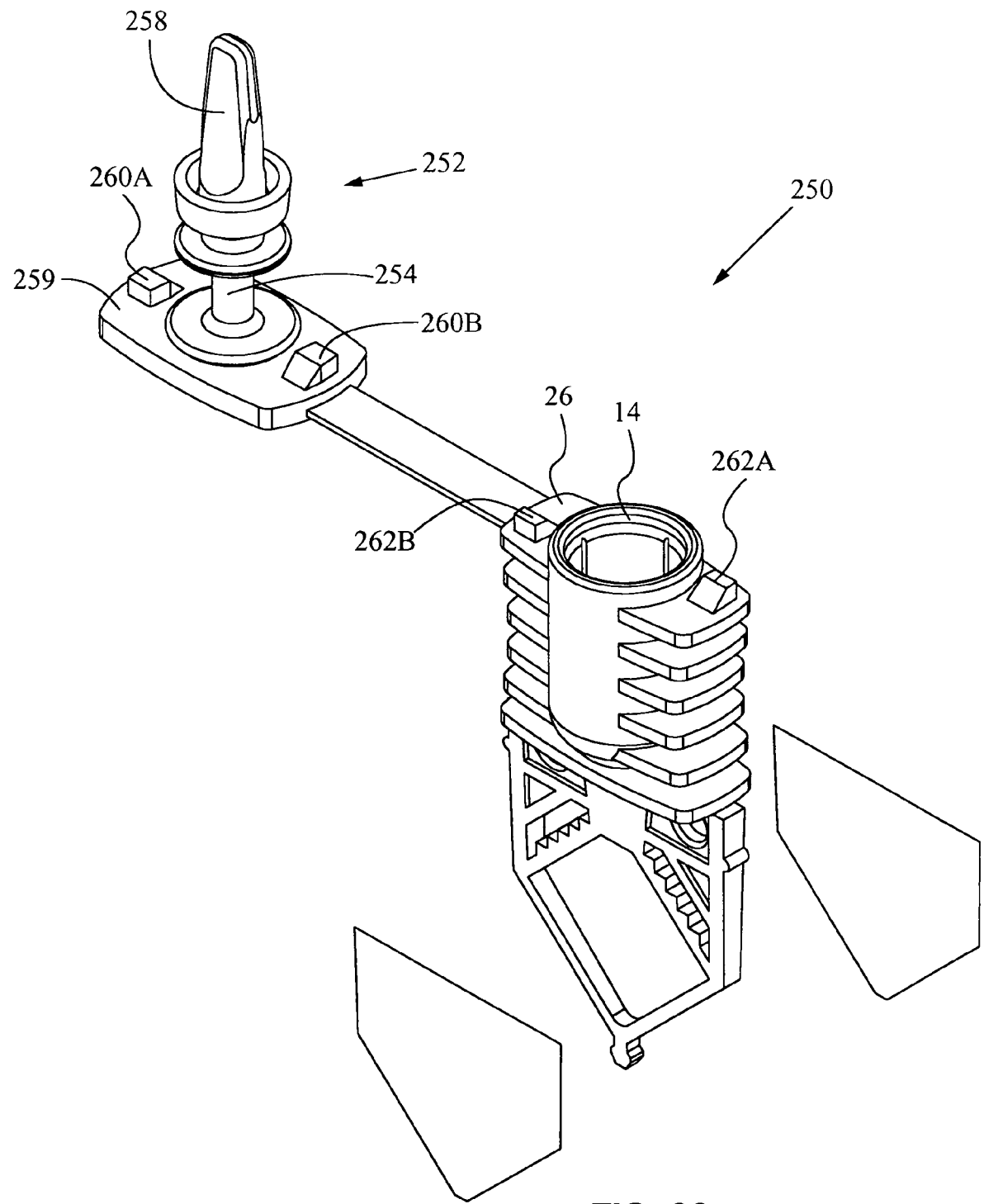
FIG. 28 is a partially exploded, isometric view of a reaction vessel according to another embodiment of the invention in which the major walls of the reaction chamber are removed to show the interior of the chamber.
Figure 29:
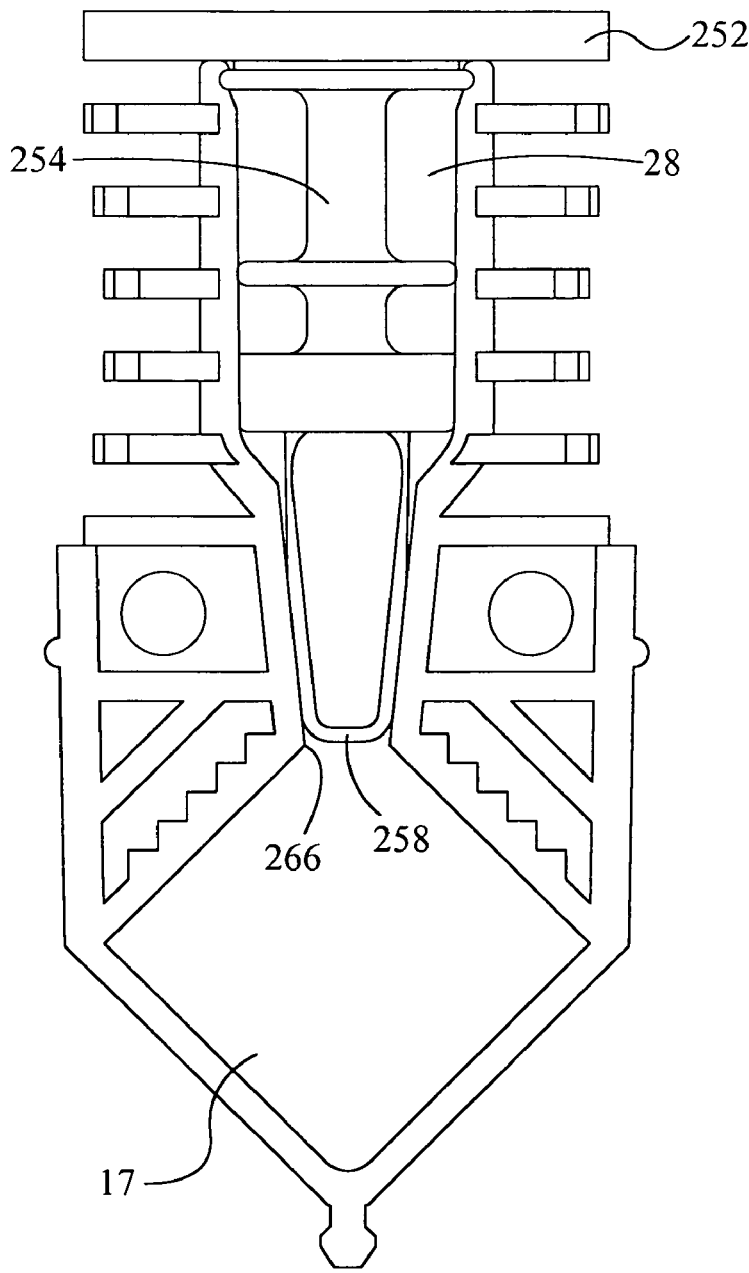
FIG. 29 is a schematic front view of the vessel of FIG. 28.
Figure 30:
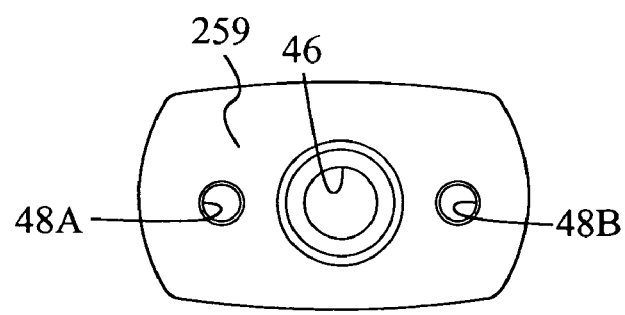
FIG. 30 is a top view of a plunger cap of the vessel of FIG. 28.
Figure 31:
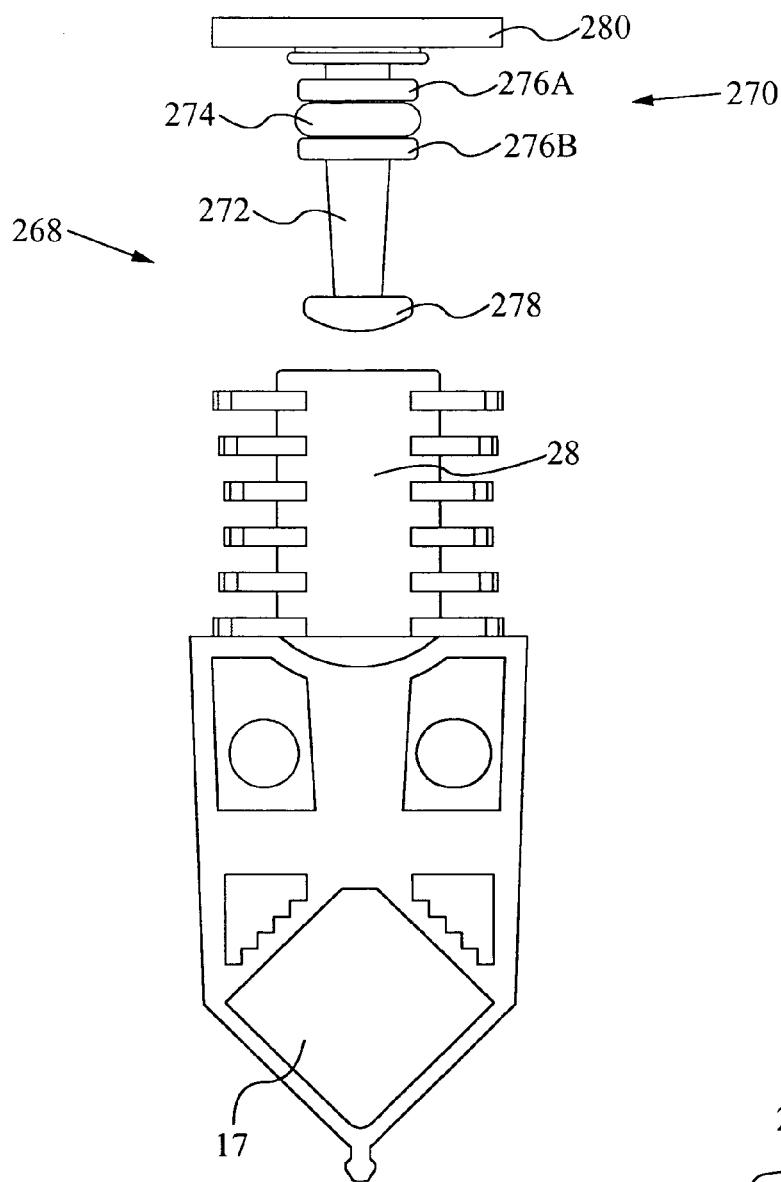
FIG. 31 is a schematic front view of a reaction vessel according to another embodiment of the invention.
Figure 32:
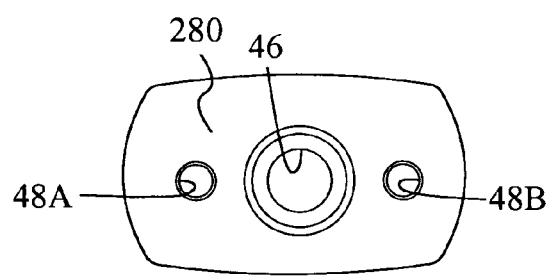
FIG. 32 is a top view of a plunger cap of the vessel of FIG. 31.

As shown in FIG. 25, the pick-and-place machine 166 also has a robotic arm or machine tip 172 for picking and placing the plunger 22 into the channel 28 of the reaction vessel 12. The machine tip 172 may optionally include an alignment pin 174 for aligning the cap 36 of the plunger in a desired angular orientation with respect to the body of the vessel 12. The alignment pin 174 provides a convenient mechanism for rotating the cap to the desired orientation before inserting the plunger 22 into the channel 28. As previously shown in FIG. 3, the cap 36 includes a tapered engagement aperture 46 for receiving and establishing a friction fit with the machine tip. The cap 36 also includes alignment apertures 48A, 48B, either one of which may receive the alignment pin. Referring again to FIG. 25, the pick-and-place machine 166 also preferably includes an ejector plate 176 that slides down the machine tip 172 to eject the plunger 22 from the machine tip after the plunger is inserted into the channel 28. Although this embodiment of the pick-and-place machine is presently preferred, many other embodiments are possible. For example, the machine tip 172 may be designed to establish a vacuum fit with the cap 36 of the plunger. Alternatively, the pick-and-place machine may have a robotic gripper arm for gripping the plunger 22 and inserting it into the channel 28. Suitable pick-and-place machines for use in the apparatus of the present invention are commercially available as machines built to specification from several suppliers, such as Tecan U.S. Inc. located at 4022 Stirrup Creek Drive, Durham, N.C. 27703.

Referring again to FIG. 20, the controller 112 preferably includes software for controlling the thermal cycler 108 and the pick-and-place machine (described above with reference to FIGS. 24-25) to perform the functions described in the operation section below. These functions include providing a user interface to enable a user to select desired thermal processing parameters (e.g., set point temperatures and hold times at each temperature) and optical detection parameters, automatic filling and pressurization of the vessels 12, thermal processing of the vessels according to the selected parameters, optical interrogation of the reaction mixtures in the vessels, and recording of the optical data generated. The creation of software and/or firmware for performing these functions can be performed by a computer programmer having ordinary skill in the art. Moreover, the software and/or firmware may reside solely in the controller 112 or may be distributed between the controller and one or more microprocessors in the thermal cycler or pick-and-place machine.

Alternatively, the controller 112 may simply be built into the thermal cycler or pick-and-place machine.

In operation, the reactor system 106 is used to thermally process and optically interrogate one or more samples. An exemplary use of the system 106 is for the amplification of nucleic acid in a sample (e.g., using PCR) and for the optical detection of one or more target analytes in the sample. A user selects a desired thermal profile for the sample using, e.g., the keyboard or mouse of the controller 112. For example, for a PCR amplification, the user may select the thermal profile to begin with a 30 second induction hold at 95° C., followed by 45 thermal cycles in which the reaction mixture is cycled between higher and lower temperatures for denaturization, annealing, and polymerization. For example, each thermal cycle may include a first set point temperature of 95° C. which is held for 1 second to denature double-stranded DNA, followed by a second set point temperature of 60° C. which is held for 6 seconds for annealing of primers and polymerization.

Referring again to FIG. 24, the sample is preferably dispensed into the vessel 12 by aspirating the sample into the pipette tip 170, inserting the pipette tip 170 through the channel 28 into the chamber 17, and dispensing the sample into the chamber. It is presently preferred that the chamber 17 be filled from the bottom up by initially inserting the pipette tip 170 close to the bottom of the chamber 17 and by slowly retracting the pipette tip 170 as the chamber 17 is filled. Filling the chamber 17 in this manner reduces the likelihood that air bubbles will form in the chamber. Such air bubbles could have a negative effect on subsequent optical detection.

The fluid sample may be mixed with chemicals necessary for the intended reaction (e.g., PCR reagents and/or fluorescent probes) prior to being added to the chamber 17. Alternatively, the sample may be introduced to the chemicals in the chamber 17, e.g., by adding the chemicals to the chamber before or after the sample to form the desired reaction mixture in the chamber. In a particularly advantageous embodiment, the necessary reagents and/or fluorescent probes for the intended reaction are placed in the chamber 17 when the vessel is manufactured. The reagents are preferably placed in the chamber 17 in dried or lyophilized form so that they are adequately preserved until the vessel is used.

Referring again to FIG. 25, the chamber 17 is then pressurized after it is filled with the reaction mixture. To increase pressure in the vessel, the machine tip 172 of the pick-and-place machine 166 engages the cap 36 of the plunger 22 and inserts the plunger into the channel 28 until the snap ring 38 snaps into the annular recess 23. As the plunger 22 is inserted, the piston 32 compresses gas in the channel 28 to increase pressure in the chamber 17, preferably to about 8 to 15 psi above ambient pressure, as previously discussed with reference to FIGS. 7A-7D. After the plunger 22 is inserted, the ejector plate 176 ejects the plunger 22 from the machine tip 172.

Referring again to FIG. 20, each of the vessels 12 may be inserted between the thermal plates of a respective heat-exchanging module 60 either prior to filling and pressurizing the vessel or after filling and pressurizing the vessel. In either case, as shown in FIG. 5, the pressure in the chamber 17 forces the flexible major walls 18 to contact and conform to the inner surfaces of the plates 50. In embodiments in which the vessels are inserted between the plates prior to filling and pressurization, the pick-and-place machine includes a robotic arm (not shown) for picking up the vessels and inserting them into the modules. Robotic arms for picking and placing reaction vessels are well known in the art.

Referring again to FIG. 25, each vessel 12 may alternatively be inserted between the plates of a respective module after filling and pressurization using the machine tip 172. In this embodiment, the vessel 12 is preferably held in a rack, tray, or similar support device during filling and pressurization. After the vessel 12 is filled and pressurized, the machine tip 172 picks up the vessel 12 by the cap 36 of the plunger 22 and inserts the chamber 17 of the vessel between the plates of a heat-exchanging module. The plunger 22 is held in the channel 28 during this movement by the snap ring 38 that engages the annular recess 23. After the vessel 12 is inserted, the ejector plate 176 ejects the cap 36 from the machine tip 172.

Although automated filling and pressurization of the vessel 12 has been described, the vessel may also be manually filled and pressurized by a human operator. This is most easily accomplished by filling the chamber 17 using a hand-held pipette or syringe and by manually inserting the plunger 22 into the channel 28. The operator then inserts the chamber 17 of the vessel into one of the heat-exchanging modules.

Referring again to FIG. 20, once a filled and pressurized reaction vessel 12 is placed between the thermal plates of a heat-exchanging module 60, the reaction mixture contained in the vessel is subjected to the thermal profile selected by the user. The controller 112 preferably implements standard proportional-integral-derivative (PID) control to execute the selected thermal profile. Referring again to FIG. 23, the controller receives signals indicating the temperatures of the plates 50A, 50B from the temperature sensors 52. Polling of the plate temperatures preferably occurs every 100 milliseconds throughout the running of the temperature profile. After each polling, the controller averages the temperatures of the two plates 50A, 50B to determine an average plate temperature. The controller then determines the difference (delta) between the profile target temperature, i.e. the set point temperature defined by the user for the particular time in the profile, and the average plate temperature. Based on the relationship between the average plate temperature and the current target temperature, the controller controls the amount of power supplied to the heating elements on the plates 50A, 50B or to the fan 66 as appropriate to reach or maintain the current set point temperature. Standard PID control is well known in the art and need not be described further herein.

The controller may optionally implement a modified version of PID control described in International Publication Number WO 99/48608 published Sep. 30, 1999, the disclosure of which is incorporated by reference herein. In this modified version of PID control, the controller is programmed to compensate for thermal lag between the plates 50A, 50B and a reaction mixture contained in a reaction vessel inserted between the plates. The thermal lag is caused by the need for heat to transfer from the plates 50A, 50B through the flexible walls of the vessel and into the reaction mixture during heating, or by the need for heat to transfer from the reaction mixture through the walls of the vessel to the plates 50A, 50B during cooling. In standard PID control, the power supplied to a heating or cooling element is dependent upon the difference (error) between the actual measured temperature of the plates and the desired set point temperature. The average power being supplied to either the heating or cooling element therefore decreases as the actual temperature of the plates approaches the set point temperature, so that the reaction mixture does not reach the set point temperature as rapidly as possible. The modified version of PID control overcomes this disadvantage of standard PID control during rapid heating or cooling steps.

To compensate for the thermal lag during heating steps (i.e., to raise the temperature of the reaction mixture to a desired set point temperature that is higher than the previous set point temperature), the controller sets a variable target temperature that initially exceeds the desired set point temperature. For example, if the set point temperature is 95° C., the initial value of the variable target temperature may be set 2 to 10° C. higher. The controller next determines a level of power to be supplied to the heating elements to raise the temperature of the plates 50A, 50B to the variable target temperature by inputting the variable target temperature and the current average plate temperature to a standard PID control algorithm. The level of power to be supplied to the heaters is therefore determined in dependence upon the difference (error) between the average plate temperature and a target temperature that is higher than the desired set point temperature. The higher target temperature ensures that a higher level of power is supplied to heat the plates 50A, 50B, and therefore the reaction mixture, to the set point temperature more rapidly. The controller then sends a control signal to the power and source control circuit in the base instrument to provide power to the heating elements at the level determined.

When the temperature of the plates 50A, 50B is subsequently polled, the controller determines if the actual measured temperature of the plates is greater than or equal to a predetermined threshold value. Suitable threshold values are: the desired set point temperature itself; or 1 to 2° C. below the set point temperature, e.g., 93 to 94° C. for a set point temperature of 95° C. If the average plate temperature does not exceed the predetermined threshold value, then the controller again determines a level of power to be supplied to the heating elements in dependence upon the difference between the average plate temperature and the target temperature and sends another control signal to provide power to the heaters at the level determined. This process is repeated until the average plate temperature is greater than or equal to the threshold value.

When the average plate temperature is greater than or equal to the threshold value, the controller decreases the variable target temperature, preferably by exponentially decaying the amount by which the variable target temperature exceeds the set point temperature. For example, the amount by which the variable target temperature exceeds the desired set point temperature may be exponentially decayed as a function of time according to the equation:

$$\Delta = (\Delta_{max}) * e^{(-t/tau)}$$

where $\Delta$ is equal to the amount by which the variable target temperature exceeds the desired set point temperature, $\Delta_{max}$ is equal to the difference between the initial value of the variable target temperature and the desired set point temperature, t is equal to the elapsed time in seconds from the start of decay, and tau is equal to a decay time constant.

In the system of the present invention, tau preferably has a value in the range of 1 to 4 seconds. It is presently preferred to determine tau empirically for the heat-exchanging module during testing and calibration of the module and to store the value of tau in the memory 160 of the module before shipping it to the end user. Although the exponential equation given above is presently preferred, it is to be understood that many other decay formulas may be employed and fall within the scope of the invention. Moreover, the variable target temperature may be decreased by other techniques, e.g., it may be decreased linearly.

After decreasing the variable target temperature, the controller determines a new level of power to be supplied to the heating elements to raise the temperature of the plates 50A, 50B to the decreased target temperature. The controller determines the level of power by inputting the current plate temperature and decreased target temperature to the PID control algorithm. The controller then sends a control signal to provide power to the heaters at the new level determined. As the time in the thermal profile progresses, the controller continues to decrease the variable target temperature until it is equal to the set point temperature. When the variable target temperature is equal to the set point temperature, standard PID control is resumed to maintain the plates 50A, 50B at the set point temperature.

To compensate for the thermal lag during cooling steps (i.e., to lower the temperature of the reaction mixture to a desired set point temperature that is lower than the previous set point temperature), the controller preferably activates the fan 66 just prior to the completion of the previous set point temperature to allow the fan to achieve maximum speed for cooling (i.e., to allow for spin-up time). The controller then sets a variable target temperature that is initially lower than the desired set point temperature. For example, if the set point temperature is 60° C., the initial value of the variable target temperature may be set 2 to 10° C. lower, i.e., 50 to 58° C. The controller continues cooling with the fan 66 until the actual measured temperature of the plates 50A, 50B is less than or equal to a threshold value, preferably the variable target temperature. When the average plate temperature is less than or equal to the variable target temperature, the controller deactivates the fan 66 and increases the target temperature, preferably by exponentially decaying the amount by which the variable target temperature differs from the set point temperature using the exponential decay equation given above. For cooling, tau is preferably in the range of 1 to 5 seconds with a preferred value of about 3 seconds. As in the heating example given above, tau may be determined empirically for the heat-exchanging module during testing or calibration and stored in the memory 160.

The controller next determines a level of power to be supplied to the heating elements to raise the temperature of the plates 50A, 50B to the increased target temperature by inputting the current average plate temperature and the increased target temperature to the PID control algorithm. The controller then sends a control signal to the power and source control circuit in the base instrument to provide power to the heating elements at the level determined. As time in the thermal profile continues, the controller continues to increase the variable target temperature and issue control signals in this manner until the variable target temperature is equal to the set point temperature. When the variable target temperature is equal to the set point temperature, the controller resumes standard PID control to maintain the plates 50A, 50B at the set point temperature.

Referring again to FIGS. 16 and 18, the reaction mixture in the vessel 12 is optically interrogated in real-time as the thermal profile is executed to determine if the mixture contains one or more target analytes. In the preferred embodiment, the mixture is optically interrogated once per thermal cycle at the lowest temperature in the cycle. Optical interrogation is accomplished by sequentially activating LEDs 100A, 100B, 100C, and 100D to excite different fluorescently-labeled analytes in the mixture and by detecting light emitted (fluorescent output) from the chamber 17 using detectors 102A, 102B, 102C, and 102D. In the following example of operation, the fluorescent dyes FAM, TAMRA, TET, and ROX are used to label the target analytes, e.g., target nucleotide sequences, nucleic acids, proteins, pathogens, or organisms in the reaction mixture.

There are four pairs of LEDs 100A, 100B, 100C, and 100D and four detectors 102A, 102B, 102C, and 102D for a total of sixteen combinations of LED/detector pairs. It is theoretically possible to collect output signals from the detectors for all sixteen combinations. Of these sixteen combinations, however, there are only four primary detection channels. Each primary detection channel is formed by a pair of LEDs in the optics assembly 68 whose excitation beams lie in the peak excitation wavelength range of a particular dye and by one corresponding detection channel in the optics assembly 70 designed to detect light emitted in the peak emission wavelength range of the same dye. The first primary detection channel is formed by the first pair of LEDs 100A and the fourth detector 102D (the ROX channel). The second primary detection channel is formed by the second pair of LEDs 100B and the third detector 102C (the TAMRA channel). The third primary detection channel is formed by the third pair of LEDs 100C and the first detector 102A (the FAM channel). The fourth primary detection channel is formed by the fourth pair of LEDs 100D and the second detector 102B (the TET channel).

Prior to activating any of the LEDs 100A, 100B, 100C, 100D, a "dark reading" is taken to determine the output signal of each of the four detectors 102A, 102B, 102C, 102D when none of the LEDs are lit. The "dark reading" signal output by each detector is subsequently subtracted from the corresponding "light reading" signal output by the detector to correct for any electronic offset in the optical detection circuit. This procedure of obtaining "dark reading" signals and subtracting the dark signals from the corresponding "light reading" signals is preferably performed every time that a reaction vessel is optically interrogated, including those times the vessel is interrogated during the development of calibration data (described in detail below). For clarity and brevity of explanation, however, the steps of obtaining "dark reading" signals and subtracting the dark signals from the corresponding "light reading" signals will not be further repeated in this description.

Following the dark reading, a "light reading" is taken in each of the four primary optical detection channels as follows. The first pair of LEDs 100A is activated and the LEDs generate an excitation beam that passes through the pair of 593 nm low pass filters 203, reflects off of the 593 nm low pass reflector 212, passes through the 555 nm low pass reflector 211, reflects off of the 527 nm high pass reflector 209, and passes through the lens 215 into the reaction chamber 17. The excitation beam from the LEDs 100A is thus filtered to a wavelength range of 555 to 593 nm corresponding to the peak excitation range for ROX. As shown in FIG. 18, emitted light (fluorescence emission radiation) from the chamber 17 passes through the lens 232 of the detection assembly 70 and strikes the 565 nm low pass reflector 229. The portion of the light having a wavelength over 605 nm (corresponding to the peak emission wavelength range of ROX) passes through the 565 nm low pass reflector 229, reflects from the 605 nm high pass reflector 227, reflects from the mirror 228, passes through the pair of 605 nm high pass filters 226, through the lens 242, through the 620 nm Schott Glass® filter 222D, and is detected by the fourth detector 102D. The fourth detector 102D outputs a corresponding signal that is converted to a digital value and recorded.

Next, as shown in FIG. 16, the second pair of LEDs 100B is activated and the LEDs generate an excitation beam that passes through the pair of 555 nm low pass filters 204, reflects off of the 555 nm low pass reflector 211, reflects off of the 527 nm high pass reflector 209, and passes through the lens 215 into the reaction chamber 17. The excitation beam from LEDs 100B is thus filtered to a wavelength range of 527 to 555 nm corresponding to the peak excitation range for TAMRA. As shown in FIG. 18, emitted light from the chamber 17 then passes through the lens 232 of the detection assembly 70 and strikes the 565 nm low pass reflector 229. The portion of the light having a wavelength in the range of about 565 to 605 nm (corresponding to the peak emission wavelength range of TAMRA) passes through the 565 nm low pass reflector 229, through the 605 nm high pass reflector 227, through the pair of 565 nm high pass filters 225, through the lens 242, through the 570 nm Schott Glass® filter 222C, and is detected by the third detector 102C. The third detector 102C outputs a corresponding signal that is converted to a digital value and recorded.

Next, as shown in FIG. 16, the pair of blue LEDs 100C is activated and the LEDs generate an excitation beam that passes through the pair of 495 nm low pass filters 205, through the 495 nm high pass reflector 208, through the 527 nm high pass reflector 209, and through the lens 215 into the reaction chamber 17. The excitation beam from LEDs 100C is thus filtered to a wavelength range of about 450 to 495 nm corresponding to the peak excitation range for FAM. As shown in FIG. 18, emitted light from the chamber 17 then passes through the lens 232 of the detection assembly 70 and strikes the 565 nm low pass reflector 229. The portion of the light having a wavelength in the range of about 505 to 537 nm (corresponding to the peak emission wavelength range of FAM) reflects from the 565 nm low pass reflector 229, passes through the 537 nm high pass reflector 230, reflects from the 505 nm high pass reflector 231, passes through the pair of 505 nm high pass filters 223, through the lens 242, through the 515 nm Schott Glass® filter 222A, and is detected by the first detector 102A. The first detector 102A outputs a corresponding signal that is converted to a digital value and recorded.

Next, as shown in FIG. 16, the fourth pair of LEDs 100D is activated and the LEDs generate an excitation beam that passes through the pair of 527 nm low pass filters 206, reflects off of the mirror 210, reflects off of the 495 nm high pass reflector 208, passes through the 527 nm high pass reflector 209, and passes through the lens 215 into the reaction chamber 17. The excitation beam from LEDs 100D is thus filtered to a wavelength range of 495 to 527 nm corresponding to the peak excitation range for TET. As shown in FIG. 18, emitted light from the chamber 17 then passes through the lens 232 of the detection assembly 70 and strikes the 565 nm low pass reflector 229. The portion of the light having a wavelength in the range of about 537 to 565 nm (corresponding to the peak emission wavelength range of TET) reflects from the 565 nm low pass reflector 229, reflects from the 537 nm high pass reflector 230, passes through the pair of 537 nm high pass filters 224, through the lens 242, through the 550 nm Schott Glass® filter 222B, and is detected by the second detector 102B. The second detector 102B outputs a corresponding signal that is converted to a digital value and recorded. The total time required to activate each of the four LEDs 100A, 100B, 100C, 100D in sequence and to collect four corresponding measurements from the detectors 102A, 102B, 102C, 102D is typically five seconds or less.

The spectrum of the fluorescence that is emitted by the dyes used for detection is usually broad. As a result, when an individual dye (e.g., FAM, TAMRA, TET, or ROX) emits fluorescence from the reaction vessel 12, the fluorescence can be detected in several of the primary detection channels, i.e. several of the detectors 102A, 102B, 102C, and 102D detect the fluorescence and generate an output signal. However, each dye has its own 'signature', i.e., the ratios of the optical signals in each detection channel are unique to each dye. It is also a reasonable assumption that the fluorescent emission from a mixture of dyes are simply additive in each of the detection channels, so that the individual dye concentrations of a dye mixture can be extracted from the mixed signals using linear algebra.

In the preferred embodiment, the controller is programmed to convert the output signals of the detectors to values indicating the true concentration of each dye labeling a respective analyte in the reaction mixture using linear algebra and a calibration matrix. A preferred method for developing the calibration matrix will now be described using the four-channel optical system of the preferred embodiment as an example. First, a reaction vessel containing only reaction buffer is optically read using optics assemblies 68, 70. The reaction buffer should be a fluid similar or nearly identical to the reaction mixtures that will be optically read by the optics assemblies during actual production use of the system to test samples. The reaction buffer should contain no dyes, so that the concentrations of all dyes are zero. The optical reading of the reaction buffer in the four primary detection channels produces four output signals that are converted to corresponding digital values. These four numbers are called Buffer(I), where 'I' is 1, 2, 3 or 4 depending upon which detection channel is read. The buffer values are a measure of the background signal or scattered light detected in each primary detection channel without any added fluorescent signal from dyes.

Next, a reaction mixture containing a known concentration, e.g. 100 nM, of dye #1 is placed into the vessel and again the four channels are read. The four numbers produced are called Rawdye(I, 1). Similar sets of four numbers are obtained for the other three dyes to obtain Rawdye(I, 2), Rawdye(I, 3), and Rawdye(I, 4). The buffer values are then subtracted from the raw dye values to obtain net dye values as follows:

$$Netdye(I,J)=Rawdye(I,J)-Buffer(I);$$

where I indicates the detection channel, and J indicates the dye number.

The matrix Netdye(I, J) is then inverted using standard numerical methods (such as Gaussian elimination) to obtain a new matrix called the calibration matrix Cal(I,J). Note that the matrix product of Netdye(I, J)*Cal(I,J) is the unity matrix. Now, any reaction mixture can be read and the output signals of the detectors in the four detection channels converted to values representative of the true concentrations of dyes labeling analytes in the mixture. The optical reading of the mixture produces four numbers called RawMix(I). The reaction buffer values are then subtracted from the raw mix values to obtain four numbers called Mix(I) as follows:

$$Mix(I)=RawMix(I)-Buffer(I)$$

Next, the true concentrations of the dyes labeling analytes are obtained by matrix multiplication as follows:

$$Truedye(I)=100\ nM*Cal(I,J)*Mix(I)$$

In the above equation, the factor of 100 comes from the fact that a concentration of 100 nM was used for the initial calibration measurements. The concentration of 100 nM is used for purposes of example only and is not intended to limit the scope of the invention.

In general, the dye concentrations for calibration measurements should be somewhere in the range of 25 to 1,000 mM depending upon the fluorescent efficiency (strength) of the dyes and their use in a particular assay or application.

Referring again to FIGS. 22-23, the matrices Cal(I, J) and Buffer(I) are preferably produced during the manufacture of each heat-exchanging module 60 and stored in the memory 160. When the module 60 is plugged into the base instrument 110, the control software application in the base instrument or external computer reads the matrices into memory and uses the matrices to convert the output signals of the detectors 102 to values indicating the concentration of each dye in the reaction mixture. Because the calibration matrices Cal(I, J) and Buffer(I) are dependent upon the particular set of dyes calibrated and the volume of the reaction vessel, it is also preferred to produce and store multiple sets of the matrices for various combinations of dye sets and reaction vessel volumes. This gives the end user greater flexibility in using the system.

As one example, calibration matrices could be stored for three different dye sets to be used with three different sizes of reaction vessels (e.g., 25 µl, 50 µl, 100 µl) for a total of nine different sets of calibration matrices. Of course, this is just one example, and many other combinations will be apparent to one skilled in the art upon reading this description. Further, in alternative embodiments, the control software may include functionality to guide the end user through the calibration procedure to enable the user to store and use calibration data for his or her own desired combination of dyes and reaction vessel size.

It is presently preferred to perform an optical reading of the reaction mixture once per thermal cycle at the lowest temperature in the cycle. Alternatively, the reaction mixture could be optically monitored more frequently or less frequently as desired by the user. One advantage to frequent optical monitoring is that real-time optical data may be used to indicate the progress of the reaction. For example, when a particular predetermined fluorescent threshold is detected in a reaction mixture in a heat-exchanging module, then the temperature cycling for that module may be stopped. Furthermore, optical detection of dye activation, e.g., color change, is useful to control the cycle parameters, not only thermal schedules, but also the state or condition of reactants and products, and quantitative production. Multiple emission wavelengths can be sampled to determine, for example, progression of the reaction, end points, triggers for reagent addition, denaturization (melting), annealing and the like. The data obtained in the real-time monitoring method may be fed back to the controller to alter or adjust the optical "read" parameters. Examples of the optical read parameters include: length of read; power input or frequency to the LEDs; which wavelength should be monitored and when; and the like.

In a typical implementation of the four-channel system, three of the optical channels are used to detect target analytes (e.g., amplified nucleic acid sequences) while the fourth channel is used to monitor an internal control to check the performance of the system. For example, beta actin is often used as an internal control in nucleic acid amplification reactions because it has a predictable amplification response and can be easily labeled and monitored to verify that the amplification is occurring properly.

One advantage of the apparatus of the preferred embodiment is that it provides extremely rapid heating and cooling of a reaction mixture. This rapid heating and cooling is particularly beneficial for nucleic acid amplification because of the increased speed with which the amplification may be accomplished and because it significantly reduces the likelihood of creating unwanted and interfering side products, such as PCR "primer-dimers" or anomalous amplicons. Another advantage of the apparatus is that it provides for sensitive, real-time detection of one or more analytes in a reaction mixture as the reaction is performed. In experimental testing of the apparatus of the preferred embodiment, extraordinary results for nucleic acid amplification and detection were achieved. For example, a 100 μl sample containing bacillus globigii in a starting concentration of 105 copies per ml has been amplified and detected in about 8 minutes (24 thermal cycles having a duration of 21 seconds per cycle).

FIG. 26 shows a reaction vessel 180 according to another embodiment of the invention. The vessel 180 is similar to the vessel of the preferred embodiment (described with reference to FIGS. 1-2), except that the vessel 180 has a smaller reaction chamber 184. The size of the chamber 184 is defined by the side walls 186A, 186B, 188A, 188B and by the thickness of the rigid frame 182. In this embodiment, each of the side walls 186A, 186B, 188A, 188B has a length L of about 5 mm, the chamber has a width W of about 7 mm, and the chamber has a thickness T of 1 mm so that the chamber has a volume capacity of 25 μL. The advantage to the vessel 180 is that it holds a smaller volume of reaction mixture so that the mixture requires less reagent. The disadvantage is that the smaller volume may cause decreased sensitivity in the detection of low concentration analytes, such as nucleic acids. The vessel 180 demonstrates that the reaction vessels of the present invention may be fabricated with chambers having various volume capacities, preferably in the range of 5 to 200 μl. It is presently preferred to fabricate each of the vessels with substantially the same size frame, regardless of the volume capacity of the chamber, so that each of the vessels may be used with the same size heat-exchanging module 60 (FIG. 8).

FIG. 27 shows a reaction vessel 190 according to another embodiment of the invention. The vessel 190 is similar to the vessel of the preferred embodiment (described with reference to FIGS. 1-2), except that the vessel 190 has an elastomeric plunger 192. The plunger 192 is constructed of an elastomeric material, e.g., a thermal plastic elastomer (TPE) or silicone. The elastomeric plunger 192 preferably includes a sealing ring 194 that establishes a seal with the walls of the channel 193 when the plunger is inserted into the channel to compress gas in the vessel and increase pressure in the chamber 191. The plunger 192 may be manually inserted into the channel 193 by human hands, or alternatively, the plunger 192 may include an engagement aperture to permit a pick-and-place machine to pick and place the plunger into the channel.

FIG. 28 shows a reaction vessel 250 according to another embodiment of the invention. The vessel 250 is similar to the vessel of the preferred embodiment (described with reference to FIGS. 1-2), except that the vessel 250 has several additional features. In particular, the plunger 252 of the vessel has a plunger cap 259 on which are formed ramp-shaped protrusions 260A, 260B. The vessel includes corresponding ramp-shaped protrusions 262A, 262B which are preferably formed on the finger grips 26 and positioned on opposite sides of the port 14. The corresponding sets of ramp-shaped protrusions engage each other provide for easy twist-off of the plunger 252, if desired, after the vessel 250 is used.

The plunger 252 also includes a stem 254 that terminates in a tongue 258. As shown in FIG. 29, the stem 254 has a length substantially equal to the length of the channel 28 so that the tip of the tongue 258 is positioned at the end of the channel 28 adjacent the entrance 266 to the chamber 17 when the plunger 252 is fully inserted in the channel. The advantage of the tongue 258 is that it provides a physical barrier for preventing the reaction mixture in the chamber 17 from bubbling up (refluxing) or evaporating into the channel 28 as the mixture is heated. As shown in FIG. 30, the cap 259 may also include an engagement aperture 46 and alignment apertures 48A, 48B to permit automated picking and placing of the plunger into the channel.

FIG. 31 shows a reaction vessel 268 according to another embodiment of the invention. The vessel 268 has a plunger 270 that differs from the plunger of the preferred embodiment (described above with reference to FIGS. 1-2). The plunger 270 includes a stem 272 and an elastomeric ring 274 encircling the stem 272. When the plunger 270 is inserted into the channel 28, the ring 274 establishes a seal with the walls of the channel. With the seal established, further insertion of the plunger 22 into the channel 28 compresses the air in the channel and creates the desired pressurization of the chamber 17 (e.g., 2 to 50 psi above the ambient pressure, or more preferably 8 to 15 psi above the ambient pressure, as previously described in the preferred embodiment). The walls of the channel 28 may have pressure control grooves if desired, as explained above with reference to FIGS. 7A-7D, to provide a controlled pressure stroke of the plunger 270. Alternatively, the pressure control grooves may be omitted so that the pressure stroke begins as soon as the ring 274 enters the channel 28 and establishes a seal with the walls of the channel.

The plunger 270 also includes two flanges 276A, 276B extending radially from the stem 272. The flanges 276A, 276B are positioned on opposite sides of the ring 274 to hold the ring in a fixed position on the stem 272. The plunger 270 may optionally have a head 278 at the end of the stem 272 for providing a physical barrier against evaporation or reflux of the reaction mixture in the chamber 17, similar to the tongue previously described with reference to FIG. 29. With the exception of the elastomeric ring 274, the plunger 270 is preferably fabricated as a one-piece polymeric part (e.g., polypropylene or polycarbonate) using known injection molding processes. After the body of the plunger 270 is molded, the ring 274 is stretched over the head 278 and positioned on the stem 272 between the flanges 276A, 276B. The ring 274 may comprise any suitable elastomeric material, e.g., a thermal plastic elastomer (TPE) or silicone. As shown in FIG. 32, the plunger cap 280 may optionally include an engagement aperture 46 and alignment apertures 48A, 48B to permit automated picking and placing of the plunger into the channel.

FIG. 33 shows an alternative embodiment of the invention in which the pressurization of the vessel 12 is performed by a pick-and-place machine 282 having a machine head 284. The machine head 284 has an axial bore 286 for communicating with the channel 28. The pick-and-place machine 282 also includes a regulated pressure source in fluid communication with the bore 286 for pressurizing the vessel 12 through the bore 286. The pressure source may comprise, e.g., a syringe pump, compressed air source, pneumatic pump, or connection to an external air supply.

The apparatus also preferably includes a disposable adapter 288 for placing the bore 286 in fluid communication with the channel 28. The adapter 288 has an axial bore 290 that connects the bore 286 in the machine head to the channel 28 in the vessel. The adapter 288 is sized to be inserted into the channel 28 such that the adapter establishes a seal with the walls of the channel. The adapter 282 preferably comprises an elastomeric material, e.g., a thermal plastic elastomer (tpe) or silicone. The adapter 288 preferably includes a one-way valve 292 (e.g., a check valve) for preventing fluid from escaping from the vessel 12.

In operation, the vessel 12 is preferably placed into a heat-exchanging module and filled with a reaction mixture as previously described in the preferred embodiment. The vessel may be filled manually by a human operator, or alternatively, the pick-and-place machine 282 may include a pipette for filling the vessel. After the chamber 17 is filled with the reaction mixture, the machine head 284 picks up the adapter 288 and inserts the adapter into the channel 28. To pick and place the adapter 288, the machine head 284 preferably has a collet for gripping and releasing the adapter 288. Alternatively, the machine head may be sized to establish a press or friction fit with the adapter 288. When inserted into the channel 28, the adapter 288 establishes a seal with the walls of the channel. The pick-and-place machine 282 then transmits gas, preferably air, from the pressure source into the channel 28 to increase the pressure in the chamber 17. The flow of air into the vessel 12 is stopped when the desired pressurization of the chamber 17 is achieved.

The desired pressurization of the chamber 17 in this embodiment is the same as that described in the preferred embodiment above. As shown in FIG. 5, the pressure in the chamber 17 should be sufficiently high to ensure that the flexible major walls 18 of the chamber outwardly expand to contact and conform to the surfaces of the plates 50A, SOB. The pressure should not be so great, however, that the walls 18 burst, become unattached from the frame 16, or deform the frame or plates. It is presently preferred to pressurize the chamber 17 to a pressure in the range of 2 to 50 psi above ambient pressure. This range is preferred because 2 psi is generally enough pressure to ensure conformity between the flexible walls 18 and the surfaces of the plates 50A, SOB, while pressures above 50 psi may cause bursting of the walls 18 or deformation of the frame 16 or plates 50A, SOB. More preferably, the chamber 17 is pressurized to a pressure in the range of 8 to 15 psi above ambient pressure. This range is more preferred because it is safely within the practical limits described above to allow for any manufacturing or operational deviations from specification.

Figure 33:
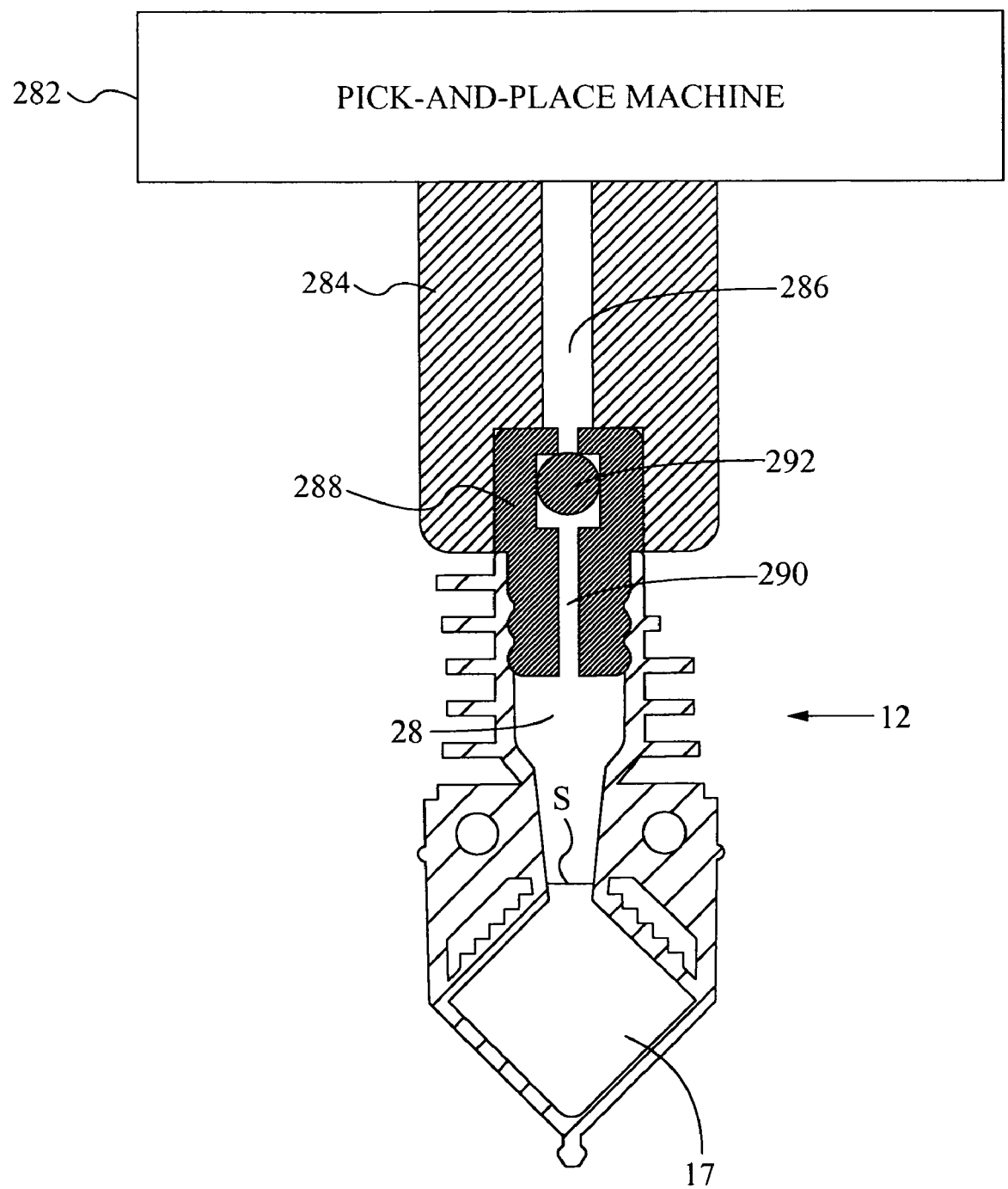
FIG. 33 is a schematic diagram of a pick-and-place machine for pressurizing a reaction vessel according to another embodiment of the invention.

Referring again to FIG. 33, the machine head 284 is disengaged from the adapter 288 following the pressurization of the vessel 12. When the machine head 284 is disengaged from the adapter 288, the valve 292 prevents fluid from escaping from the vessel 12. Thus, the chamber 17 remains pressurized for thermal processing and the vessel 12 is effectively sealed to prevent the reaction mixture in the vessel from contaminating the external environment. The remaining operation of this embodiment is analogous to the operation of the preferred embodiment described above.

Figure 34:
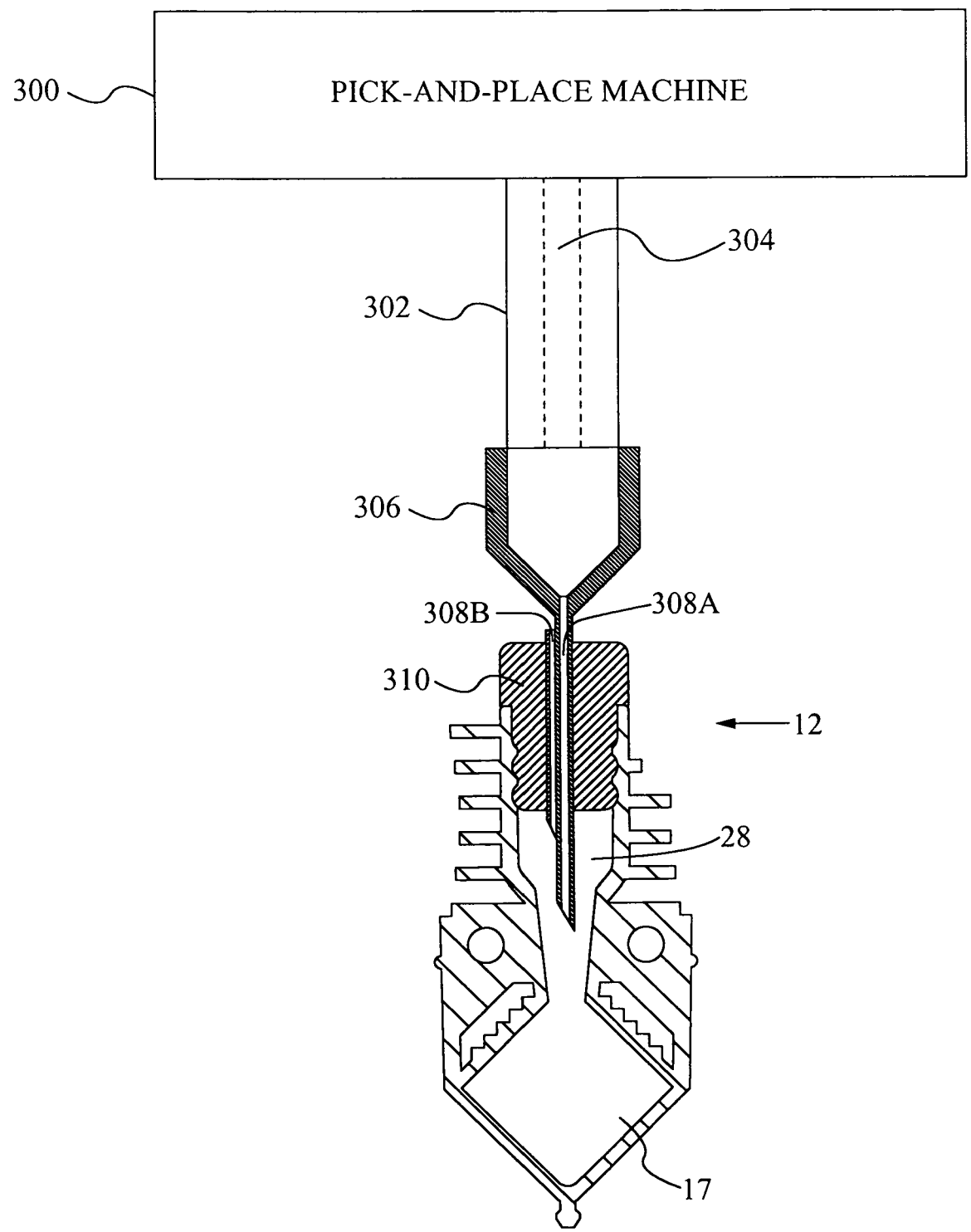
FIGS. 34-35 are a schematic diagrams of a pick-and-place machine using a double-bore needle to fill and pressurize a reaction vessel according to an alternative embodiment of the invention.

FIG. 34 shows another embodiment of the invention in which the filling and pressurization of vessel 12 is performed by a pick-and-place machine 300 having a machine head 302 for manipulating a needle 306. The machine head 302 has an axial bore 304 for communicating with the needle 306. The pick-and-place machine 300 has controllable vacuum and pressure sources in communication with the bore 304 for aspirating and dispensing fluids using the needle 306. The vacuum and pressure sources may comprise, e.g., one or more syringe pumps, compressed air sources, pneumatic pumps, vacuum pumps, or connections to external sources of pressure. The machine head 302 engages the needle 306 using any standard needle fitting, such as a luer lock. The needle 306 is preferably a double-bore needle having a first bore 308A for injecting fluid into the vessel 12 and a second bore 308B for venting gas from the vessel. For reasons that will soon be apparent, the first bore 308A has a length greater than the second bore 308B.

The apparatus also includes an elastomeric plug 310 that is inserted into the channel 28 of the vessel such that the plug forms a seal with the walls of the channel. The needle 306 is inserted through the plug 310 by the machine head 302 to fill and pressurize the chamber 17. The elastomeric plug 310 should be self-sealing so that it seals fluid within the vessel 12 when the needle 306 is withdrawn from the plug 310. The plug 310 is preferably inserted into the channel 28 during manufacture of the vessel 12. Alternatively, the plug 310 may be inserted into the channel 28 just prior to using the vessel 12, e.g., the plug may be inserted by a robotic arm or machine tip of the pick-and-place machine 300 or the plug may be manually inserted by a human operator.

In operation, the vessel 12 is preferably placed into a heat-exchanging module as previously described in the preferred embodiment, e.g., by the pick-and-place machine 300 or by human hands. The vessel 12 is then filled and pressurized by the pick-and-place machine 300 as follows. The machine head 302 picks up the needle 306 and aspirates the reaction mixture into the needle through the first bore 308A. The machine head 302 then inserts the needle through the plug 310 such that the first bore 308A is in fluid communication with the channel 28 and such that the second bore 308B has one end disposed in the channel 28 and a second end positioned outside of the vessel 12 and plug 310. The pick-and-place machine 300 then dispenses the reaction mixture into the chamber 17 through the first bore 308A of the needle. As the chamber 17 is filled, displaced air in the vessel 12 is vented to the atmosphere through the second bore 308B.

Figure 35:
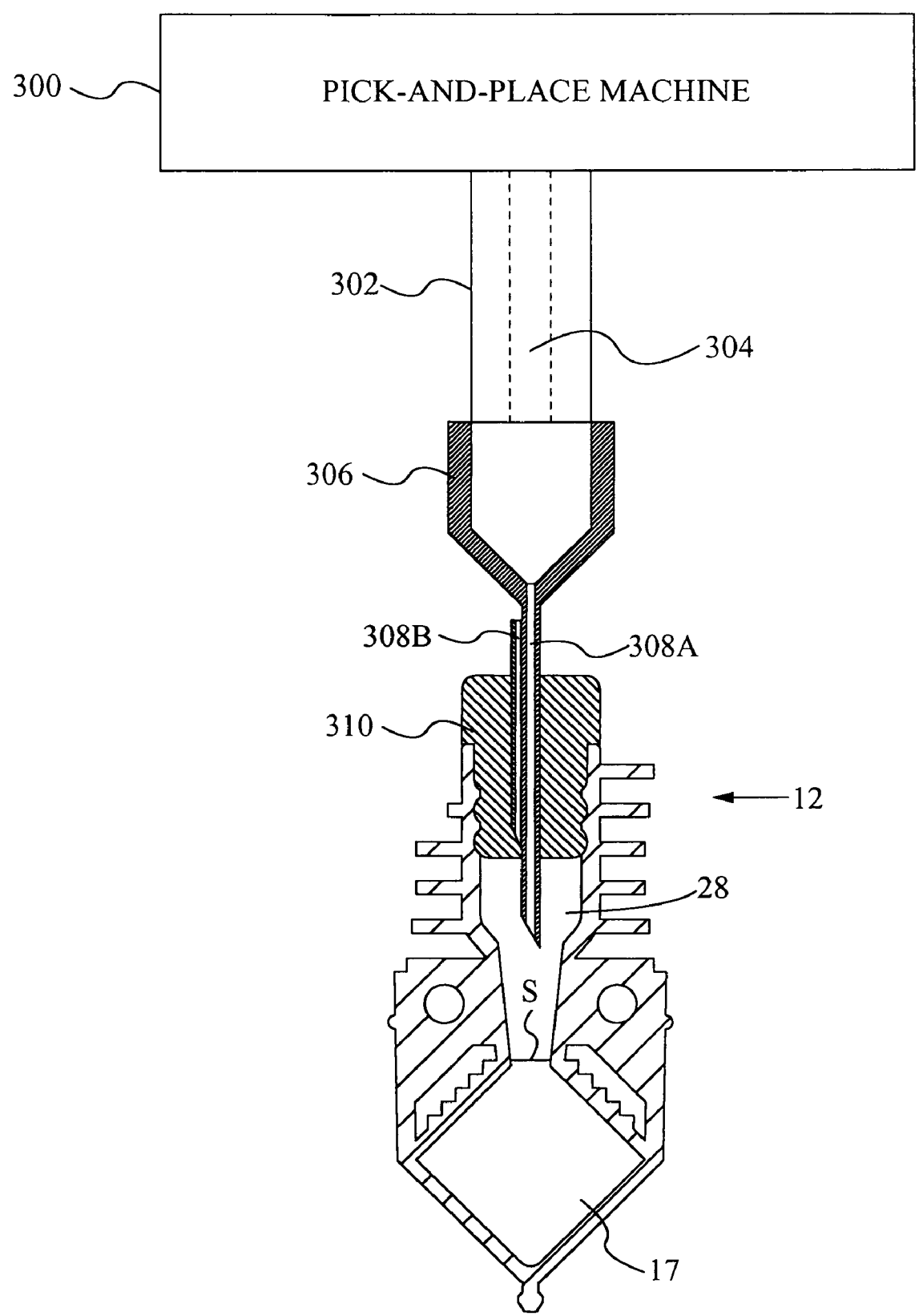

As shown in FIG. 35, the machine head 302 then partially retracts the needle 306 from the plug 310 after the chamber 17 is filled with the reaction mixture. The needle 306 is partially retracted such that the end of the first bore 308A is still in fluid communication with the channel 28, but the end of the second bore 308B is enclosed within the plug 310. In this position, the second bore 308B can no longer vent air from the channel 28. The pick-and-place machine 300 then flows gas, preferably air, from the controllable pressure source into the channel 28 through the first bore 308A to increase pressure in the chamber 17. The machine 282 then stops the flow of air when the desired pressurization of the chamber 17 is achieved.

The desired pressurization of the chamber 17 in this embodiment is the same as that described in previous embodiments, e.g., 5 to 50 psi and more preferably 8 to 15 psi for the reasons discussed above. Following pressurization, the machine head 302 fully retracts the needle 306 from the plug 310, and the plug 310 self seals to maintain the desired pressure in the vessel 12 for thermal processing. The needle 306 is preferably disposable to prevent cross contamination of fluid samples. The remaining operation of this embodiment is analogous to the operation of the preferred embodiment described above.

Figure 36:
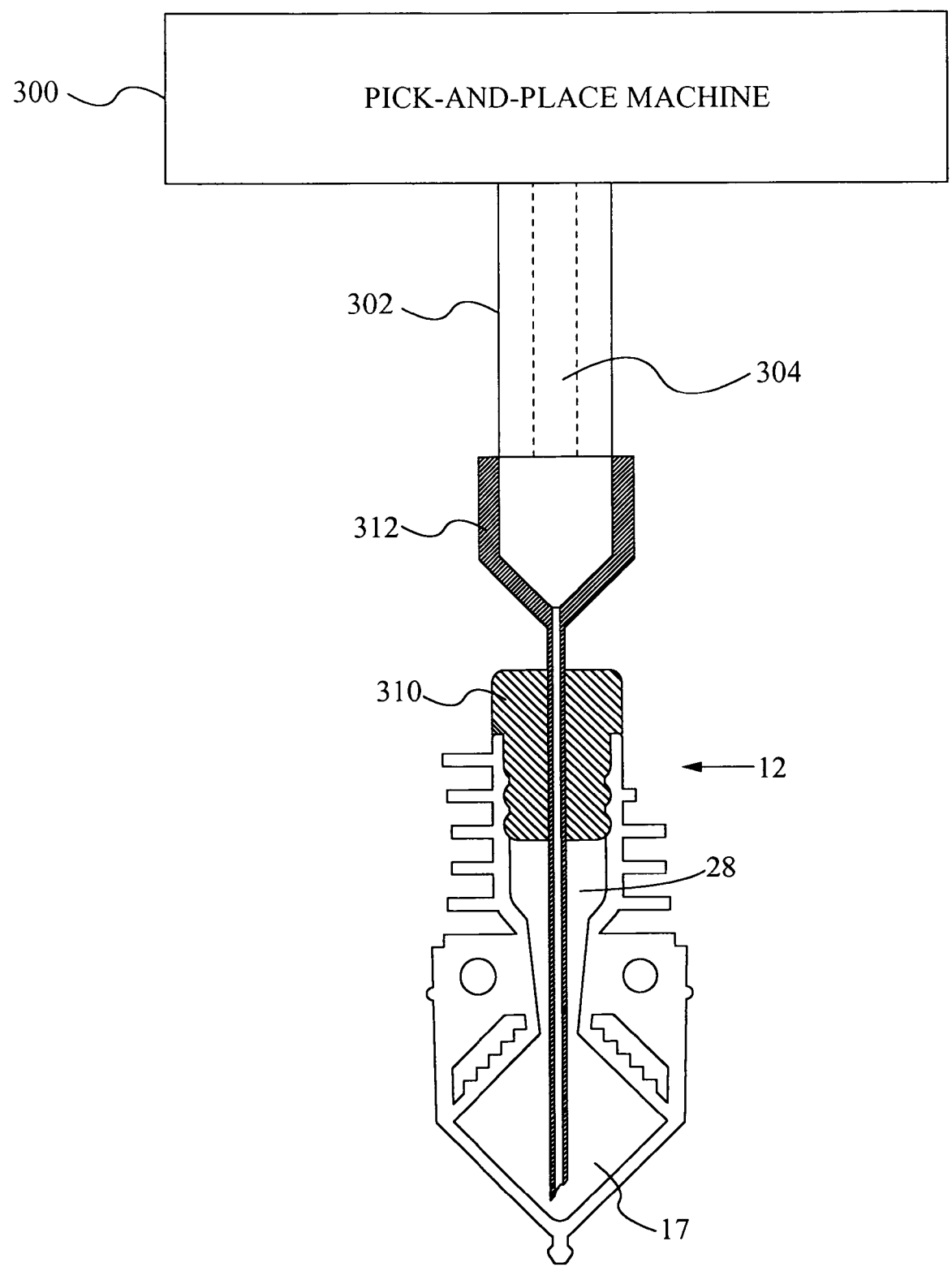
FIGS. 36-37 are schematic diagrams of a pick-and-place machine using a single-bore needle to fill and pressurize a reaction vessel according to another embodiment of the invention.

FIG. 36 shows a slightly different embodiment of the invention in which the machine head 302 manipulates a single-bore needle 312 to fill and pressurize the chamber 17 in a single step. In operation, the machine head 302 picks up the needle 312 and aspirates the reaction mixture into the needle. The machine head 302 then inserts the needle 312 through the plug 310 and dispenses the reaction mixture into the chamber 17. It is presently preferred that the chamber 17 be filled from the bottom up by initially inserting the needle 312 close to the bottom of the chamber 17 and by slowly retracting the needle as the chamber 17 is filled. Filling the chamber 17 in this manner reduces the likelihood that air bubbles will form in the chamber.

Figure 37:
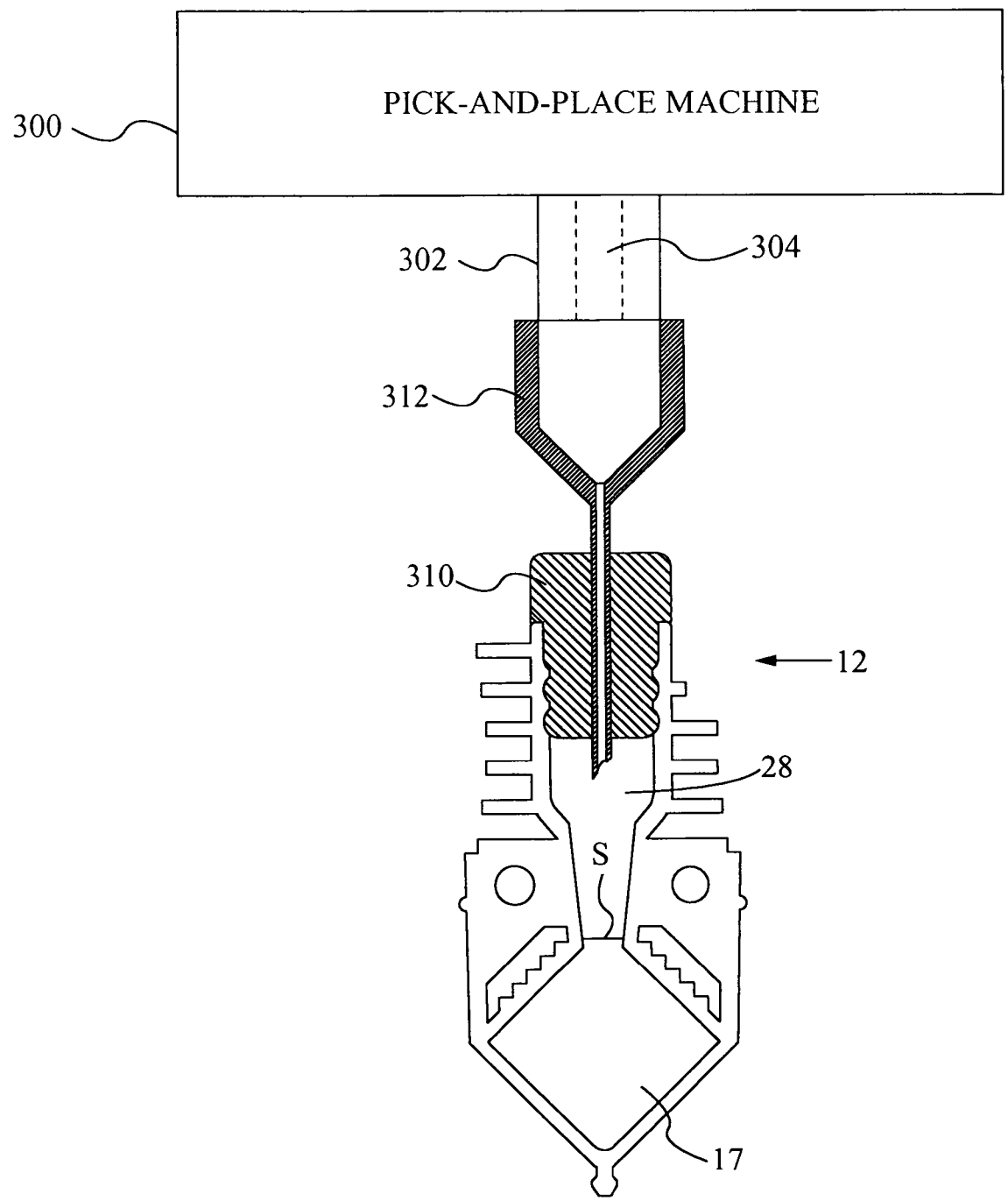

Referring to FIG. 37, as the reaction mixture is added to the chamber 17, the mixture displaces air in the vessel. The displaced air is trapped between the liquid surface level S and the plug 310 so that the air compresses in the channel 28. The compression of the air is usually sufficient to cause the desired pressurization of the chamber 17, e.g., 2 to 50 psi above the ambient pressure, and more preferably 8 to 15 psi above the ambient pressure.

Thus, the filling of the chamber 17 also provides for quick and convenient pressurization in a single step. Alternatively, the pick-and-place machine 300 may be programmed to increase or decrease the pressure in the vessel 12 by adding air to the channel 28 or releasing air from the channel through the needle 312, as appropriate, to achieve the desired pressure in the chamber 17. The machine 300 preferably includes a pressure regulator for this purpose. Suitable pressure regulators are well known in the art.

After the desired pressurization of the chamber 17 is achieved, the machine head 302 retracts the needle 312 from the plug 310, and the plug 310 seals itself to maintain the pressure in the vessel 12 for thermal processing. Many variations to this embodiment are possible. For example, there may be low pressure or a vacuum in the vessel 12 prior to adding the reaction mixture to the chamber 17. To fill and pressurize the chamber 17, the pick-and-place machine 300 first dispenses the reaction mixture into the chamber 17 through the needle 312 and retracts the end of the needle into the channel 28. The machine 300 then flows air from the controllable pressure source into the channel 28 through the needle 312 to achieve the desired pressurization of the chamber 17. The machine head 302 then retracts the needle 312 from the plug 310, and the plug 310 seals itself to maintain the pressure in the vessel 12 for thermal processing. The remaining operation of this embodiment is the same as the operation of the preferred embodiment described above.

Figure 38:
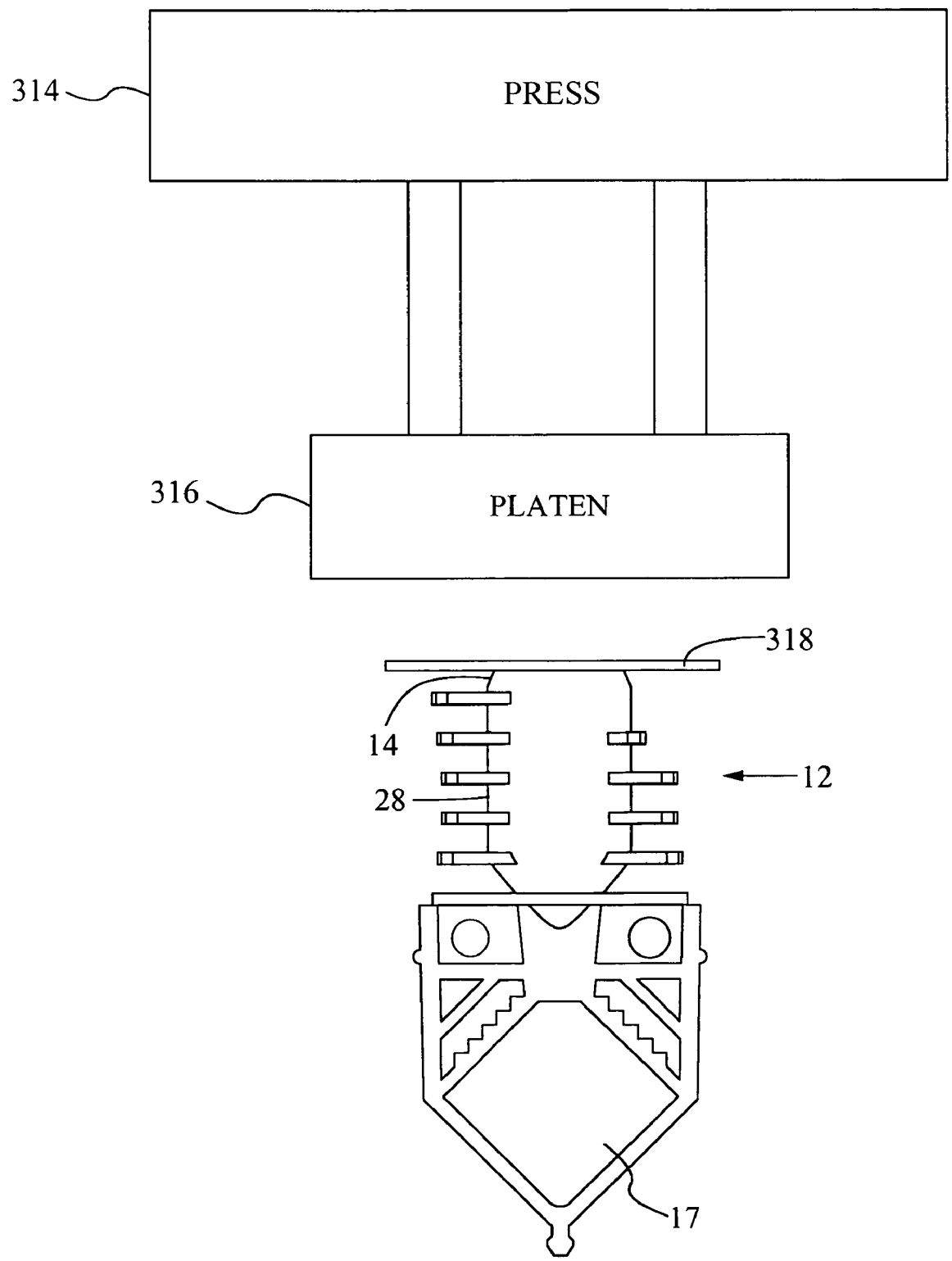
FIGS. 38-39 are schematic diagrams of a press machine having a platen for sealing a port of a reaction vessel according to an alternative embodiment of the invention.

FIG. 38 shows another embodiment of the invention in which the sealing and pressurization of vessel 12 is performed by a press 314 having a heated platen 316 for heat sealing a film or foil 318 to the portion of the frame 16 forming the port 14. The foil 18 is preferably a laminate comprising a layer of metal (e.g., aluminum) on top of a layer of polymeric material (e.g., polypropylene or polyester). In operation, the vessel 12 is preferably placed in a holder (e.g., a tray or nest) that moves on an assembly line for automated filling, sealing, and pressurization of the vessel. In a first step, the chamber 17 of the vessel is filled with a reaction mixture using, e.g., a pipette or syringe. After the chamber 17 is filled, the foil 318 is placed on top of the port 14 with the metal layer facing up. The foil 318 may be placed on the vessel manually by a human operator, or more preferably, by the robotic arm of a pick-and-place machine. The vessel 12 is then moved under the heated platen 316 for sealing and pressurization. The platen 316 is then pressed to the top of the vessel 12 and the platen 316 heat seals the foil 318 to the vessel to seal the port 14.

Figure 39:
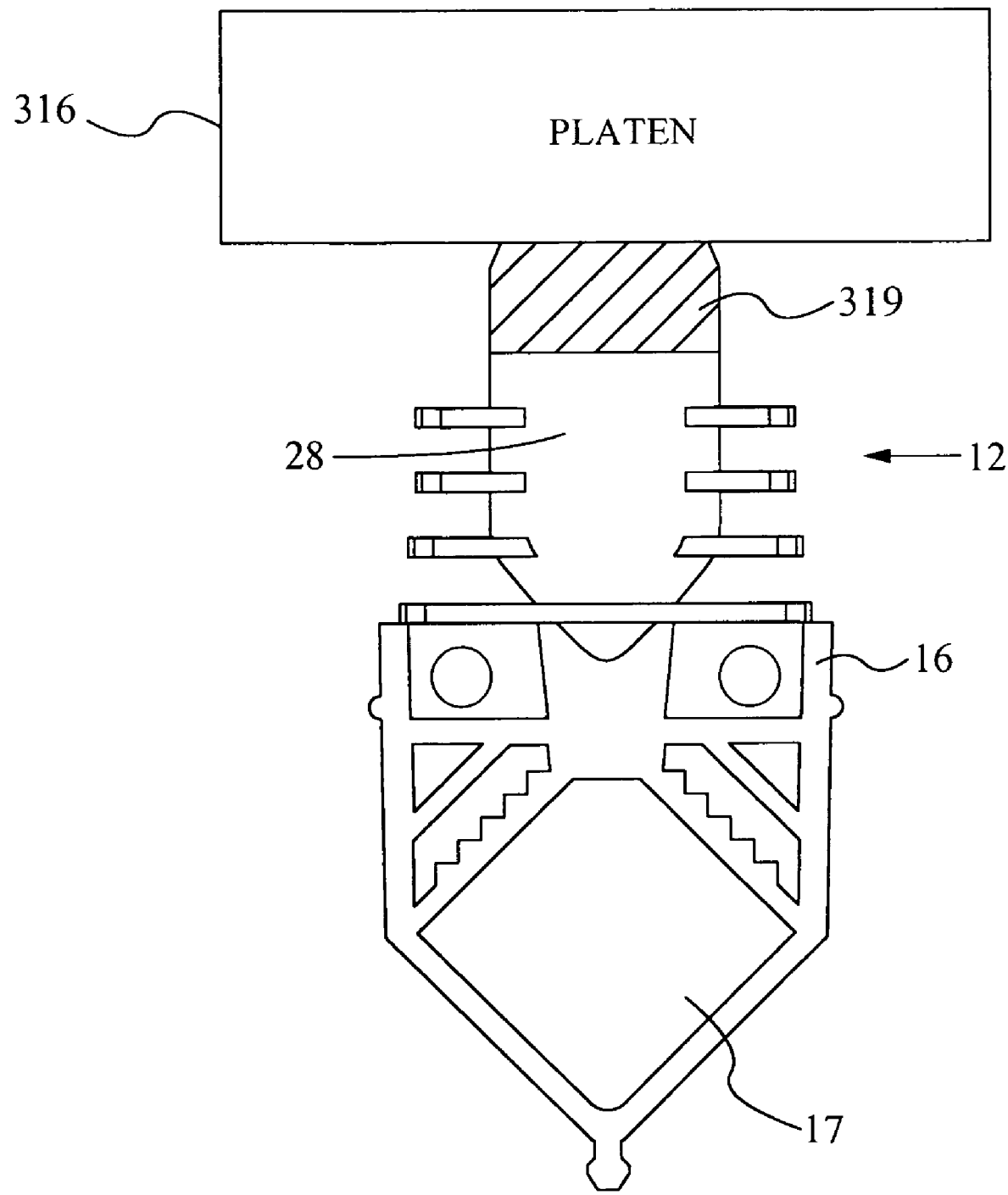

As shown in FIG. 39, the heat from the platen 316 also melts the top portion of the frame 16, thereby collapsing an end of the channel 28 to produce a collapsed zone 319. The volume of the channel 28 is therefore reduced. The reduction of the volume of the channel 28 after the port is sealed compresses air trapped in the channel and causes the desired pressurization of the chamber 17. The desired pressurization of the chamber 17 in this embodiment is the same as that described in the previous embodiments, e.g., 2 to 50 psi above the ambient pressure, and more preferably 8 to 15 psi above the ambient pressure. After the vessel 12 is sealed and pressurized in this manner, it is picked and placed into one of the heat-exchanging modules 60 (FIG. 20) for thermal processing and optical detection. The remaining operation of this embodiment is the same as the operation of the preferred embodiment described above.

The desired pressurization of the chamber 17 may be achieved by use of the equation:

$$P_i * V_i = P_f * V_f;$$

where:

$P_i$ is equal to the initial pressure in the vessel 12 prior to sealing the port;

$V_i$ is equal to the initial volume of the channel 28 prior to collapsing an end of the channel;

$P_f$ is equal to the desired final pressure in the chamber 17; and $V_f$ is equal to the final volume of the channel 28 after collapsing an end of the channel.

To ensure the desired final pressure $P_f$ in the chamber 17, the heat-sealing of the vessel should reduce the volume of the channel 28 such that the ratio of the volumes $V_i:V_f$ is substantially equal to the ratio of the pressures $P_f:P_i$. An engineer having ordinary skill in the art will be able to select suitable values for the volumes $V_i$ and $V_f$ using the description and equation given above. For example, if the initial pressure $P_i$ in the vessel is equal to standard atmospheric pressure of about 14 psi, the desired final pressure $P_f$ is equal to 26 psi (the desired 12 psi above ambient pressure), and the initial volume $V_i$ of the channel is equal to 150 µl, then the heat sealing of the vessel should reduce the volume of the channel to a final volume $V_f$ of about 80 µl. This is just one example of suitable values for the initial and final volumes, and it is to be understood that the scope of the invention is not limited to this example. Many other suitable values may be selected to achieve the desired ratios, as will be apparent to one having ordinary skill in the art.

The various embodiments of the apparatus of the present invention may find use in many applications. The apparatus may be utilized to perform chemical reactions on samples, e.g., nucleic acid amplification, and to optically detect amplified target sequences. Although amplification by PCR has been described herein, it will be appreciated by persons skilled in the art that the apparatus may be utilized for a variety of other polynucleotide amplification reactions and ligand-binding assays. Such additional reactions may be thermally cycled or they may be carried out at a single temperature, e.g., isothermal nucleic acid amplification. Polynucleotide amplification reactions that may be practiced in the system of the invention include, but are not limited to: (1) target polynucleotide amplification methods such as self-sustained sequence replication (3 SR) and strand-displacement amplification (SDA): (2) methods based on amplification of a signal attached to the target polynucleotide, such as "branched chain" DNA amplification; (3) methods based on amplification of probe DNA, such as ligase chain reaction (LCR) and QB replicase amplification (QBR); (4) transcription-based methods, such as ligation activated transcription (LAT) and nucleic acid sequence-based amplification (NASBA); and (5) various other amplification methods, such as repair chain reaction (RCR) and cycling probe reaction (CPR). Other applications of the apparatus are intended to be within the scope of the invention where those applications require the transfer of thermal energy to a reaction mixture and/or optical detection of reaction products.

SUMMARY, RAMIFICATIONS, AND SCOPE

Although the above description contains many specificities, these should not be construed as limitations on the scope of the invention, but merely as examples of some of the presently preferred embodiments. Many modifications or substitutions may be made to the apparatus and methods described without departing from the scope of the invention. For example, in one alternative embodiment, the reaction vessel has only one flexible sheet forming a major wall of the reaction chamber. The rigid frame defines the other major wall of the chamber, as well as the side walls of the chamber. In this embodiment, the major wall formed by the frame should have a minimum thickness of about 0.05 inches (the practical minimum thickness for injection molding), while the flexible sheet may be as thin as 0.0005 inches. The advantage to this embodiment is that the manufacturing of the reaction vessel is simplified, and hence less expensive, since only one flexible sheet need be attached to the frame. The disadvantage is that the heating and cooling rates of the reaction mixture are likely to be slower since the major wall formed by the frame will probably not permit as high a rate of heat transfer as the thin, flexible sheet.

In addition, the apparatus only requires one thermal surface for contacting a flexible wall of the reaction vessel and one thermal element for heating and/or cooling the thermal surface. The advantage to using one thermal surface and one thermal element is that the apparatus may be manufactured less expensively. The disadvantage is that the heating and cooling rates are likely to be about twice as slow. Further, although it is presently preferred that the thermal surfaces be formed by thermally conductive plates, each thermal surface may be provided by any rigid structure having a contact area for contacting a wall of the vessel. The thermal surface preferably comprises a material having a high thermal conductivity, such as ceramic or metal. Moreover, the thermal surface may comprise the surface of the thermal element itself. For example, the thermal surface may be the surface of an ultrasonic transducer that contacts the flexible wall of the chamber for ultrasonic heating and/or lysing of the sample in the chamber. Alternatively, the thermal surface may be the surface of a thermoelectric device that contacts the wall to heat and/or cool the chamber.

The filters used in the optics assemblies may be designed to provide excitation and emission light in any wavelength ranges of interest, not just the specific wavelength ranges described above. The choice of fluorescent dyes for any given application depends upon the analytes of interest. One skilled in the art will realize that different combinations of light sources, filters, or filter wavelengths may be used to accommodate the different peak excitation and emission spectra of the selected dyes. Moreover, although blue and green light sources are presently preferred, different color light sources, such as blue-green, red, or amber LEDs, may be used in the apparatus. Further, infrared or ultraviolet light sources may be used.

Moreover, although fluorescence excitation and emission detection is a preferred embodiment, optical detection methods such as those used in direct absorption and/or transmission with on-axis geometries may also be applied to the apparatus of the present invention. Alternative geometries, such as on-axis alignments of light sources and detectors, can be used to monitor changes in dye concentrations and physical conditions (temperature, pH, etc.) of a reaction by measuring absorption of the illumination. The optics may also be used to measure time decay fluorescence. Additionally, the optics are not limited to detection based upon fluorescent labels. The optics system may be applicable to detection based upon phosphorescent labels, chemiluminescent labels, or electrochemiluminescent labels.

Therefore, the scope of the invention should be determined by the following claims and their legal equivalents.

What is claimed is:

1. An apparatus for controlling the temperature of a reaction mixture, the apparatus comprising:
    a) a reaction vessel having a chamber for holding the mixture, the vessel comprising:
        i) a rigid frame defining side walls of the chamber, wherein the frame further includes a port and a channel connecting the port to the chamber; and
        ii) at least one flexible sheet attached to the rigid frame to form a major wall of the chamber;
    b) at least one thermal surface for contacting the major wall;
    c) an automated machine, comprising a pick-and-place machine for inserting a plunger into the channel to compress gas in the vessel, thereby increasing the pressure in the chamber, wherein the pressure increase in the chamber is sufficient to force the major wall to conform to the thermal surface; and
    d) at least one thermal element for heating or cooling the surface to induce a temperature change within the chamber.

2. The apparatus of claim 1, wherein the vessel includes first and second flexible sheets attached to opposite sides of the rigid frame to form opposing major walls of the chamber, the apparatus includes first and second thermal surfaces formed by opposing plates positioned to receive the chamber between them, and the pressure increase in the chamber is sufficient to force the major walls to contact and conform to the inner surfaces of the plates.

3. The apparatus of claim 2, wherein each of the plates comprises a ceramic material, and wherein each of the plates has a thickness less than or equal to 1 mm.

4. The apparatus of claim 2, wherein each of the plates has a resistive heating element coupled thereto.

5. The apparatus of claim 4, wherein the heating element comprises a film.

6. The apparatus of claim 2, wherein each of the plates has a thermal mass less than 5 J/° C.

7. The apparatus of claim 2, wherein each of the plates has a thermal mass less than 3 J/° C.

8. The apparatus of claim 2, wherein each of the plates has a thermal mass less than 1 J/° C.

9. The apparatus of claim 2, further comprising a support structure for holding the plates in an opposing relationship to each other, the support structure comprising:
    a) a mounting plate having a slot therein;
    b) spacing posts extending from the mounting plate on opposite sides of the slot, wherein each of the spacing posts has indentations formed on opposite sides thereof for receiving the edges of the plates; and
    c) retention clips for holding the edges of the plates in the indentations.

10. The apparatus of claim 1, wherein the frame includes an inner surface defining the channel, and wherein the inner surface has at least one pressure control groove formed therein, the pressure control groove extending to a predetermined depth in the channel to allow gas to escape from the vessel until the plunger reaches the predetermined depth.

11. The apparatus of claim 1, wherein the plunger has a pressure stroke sufficient to increase the pressure in the chamber to at least 2 psi above the ambient pressure external to the vessel.

12. The apparatus of claim 1, wherein the automated machine comprises:
    a) a machine head having an axial bore for communicating with the channel of the vessel; and
    b) a pressure source for pressurizing the chamber through the bore in the machine head.

13. The apparatus of claim 12, further comprising an adapter for placing the bore in fluid communication with the channel, wherein the adapter is sized to be inserted into the channel such that the adapter establishes a seal with the walls of the channel.

14. The apparatus of claim 13, wherein the adapter includes a valve for preventing fluid from escaping from the vessel.

15. The apparatus of claim 1, further comprising an elastomeric plug inserted into the channel, wherein the automated machine comprises:
   a) means for inserting a needle through the plug; and
   b) a pressure source for injecting fluid into the vessel through the needle.

16. The apparatus of claim 15, wherein the needle includes a first bore for dispensing the fluid into the vessel and a second bore for venting gas from the vessel, and wherein the first bore has a length greater than the second bore.

17. The apparatus of claim 1, wherein the automated machine comprises a platen for heat sealing a film or foil to the vessel to seal the port and reduce the volume of the channel.

18. The apparatus of claim 1, wherein:
   a) at least two of the side walls of the chamber are optically transmissive and angularly offset from each other;
   b) the apparatus further comprises an optics system having at least one light source for exciting the mixture through a first one of the optically transmissive side walls and having at least one detector for detecting light emitted from the chamber through a second one of the optically transmissive side walls.

19. The apparatus of claim 18, wherein:
   a) the apparatus includes first and second thermal surfaces formed by opposing plates positioned to receive the chamber of the vessel between them; and
   b) each of the plates has first and second edges angularly offset from each other by substantially the same angle that the optically transmissive side walls are offset from each other, and the plates are positioned to receive the chamber between them such that the first optically transmissive side wall is positioned substantially adjacent and parallel to the first bottom edge of each plate and such that the second optically transmissive side wall is positioned substantially adjacent and parallel to the second bottom edge of each plate.

20. The apparatus of claim 18, wherein the optically transmissive side walls are angularly offset from each other by about 90°.

21. The apparatus of claim 18, wherein at least two additional side walls of the chamber have retro-reflective faces.

22. The apparatus of claim 18, wherein the ratio of the width the chamber to the thickness of the chamber is at least 4:1, and wherein the chamber has a thickness in the range of 0.5 to 2 mm.

23. The apparatus of claim 18, wherein the plates, thermal element, and optics system are incorporated into a heat-exchanging module, the apparatus further comprises a base instrument for receiving the heat-exchanging module, and the base instrument includes processing electronics for controlling the operation of the module.

24. The apparatus of claim 23, wherein the heat-exchanging module further comprises a housing and a cooling element disposed within the housing for cooling the reaction mixture contained in the chamber.

25. The apparatus of claim 23, wherein the base instrument is constructed to receive and control a plurality of such heat-exchanging modules.

26. The apparatus of claim 25, further comprising at least one computer for controlling the base instrument.

27. An apparatus for controlling the temperature of a reaction mixture, the apparatus comprising:
   a) a reaction vessel having a reaction chamber and at least one port for adding fluid to the chamber, and wherein the chamber has at least one flexible wall;
   b) a thermal surface for contacting the flexible wall;
   c) an automated machine for increasing the pressure in the chamber, comprising
      i) a machine head having a bore for communicating with the vessel; and
      ii) a pressure source for pressuring the chamber through the machine head,
      wherein the pressure increase in the chamber is sufficient to force the flexible wall to contact and conform to the thermal surface; and
   d) at least one thermal element for heating or cooling the thermal surface to induce a temperature change within the chamber.

28. The apparatus of claim 27, wherein the vessel further comprises a first and a second major flexible wall, and wherein the apparatus includes first and second thermal surfaces formed by opposing plates positioned to receive the chamber of the vessel between them, and wherein each of the plates has a heating element coupled thereto.

29. The apparatus of claim 28, wherein each of the plates has a thermal mass less than 5 J/° C.

30. The apparatus of claim 28, wherein each of the plates has a thermal mass less than 1 J/° C.

31. The apparatus of claim 27, wherein the vessel includes a channel connecting the port to the chamber, and wherein the automated machine comprises a pick-and-place machine for inserting a plunger into the channel to compress gas in the vessel.

32. The apparatus of claim 27, further comprising an adapter for placing the machine head in fluid communication with the vessel, wherein the vessel includes a channel connecting the port to the chamber, and wherein the adapter is sized to be inserted into the channel such that the adapter establishes a seal with the walls of the channel.

33. The apparatus of claim 27, further comprising an adapter for placing the machine head in fluid communication with the vessel, wherein the adapter includes a valve for preventing fluid from escaping from the vessel.

34. The apparatus of claim 27, wherein the automated machine further comprises
   means for dispensing fluid into the vessel through the machine head.

35. The apparatus of claim 27, wherein the vessel further comprises:
   a) a channel connecting the port to the chamber;
   b) an elastomeric plug inserted into the channel; and
   wherein the automated machine further comprises:
   a) a needle for inserting through the plug;
   b) means for inserting the needle through the plug; and
   c) means for injecting fluid into the vessel through the needle.

36. The apparatus of claim 35, wherein the needle includes a first bore for dispensing the fluid into the vessel and a second bore for venting gas from the vessel, and wherein the first bore has a length greater than the second bore.

37. The apparatus of claim 27, wherein the automated machine comprises a platen for heat sealing a film or foil to the vessel to seal the port.

38. The apparatus of claim 27, further comprising an optics system for optically interrogating the mixture contained in the chamber through first and second optically transmissive walls of the vessel, the optics system having at least one light source for exciting the mixture through the first wall and having at least one detector for detecting light emitted from the chamber through the second wall.

39. The apparatus of claim 38, wherein the plates, heating elements, and optics system are incorporated into a heat-exchanging module, the apparatus further comprises a base instrument for receiving the heat-exchanging module, and the base instrument includes processing electronics for controlling the operation of the module.

40. The apparatus of claim 28, wherein each of the plates comprises a ceramic material, and wherein each of the plates has a thickness less than or equal to 1 mm.

41. The apparatus of claim 28, wherein the heating element comprises a film.

42. The apparatus of claim 28, further comprising a support structure for holding the plates in an opposing relationship to each other, the support structure comprising:
   a) a mounting plate having a slot therein;
   b) spacing posts extending from the mounting plate on opposite sides of the slot, wherein each of the spacing posts has indentations formed on opposite sides thereof for receiving the edges of the plates; and
   c) retention clips for holding the edges of the plates in the indentations.

43. The apparatus of claim 31, wherein an inner surface of the channel has at least one pressure control groove formed therein, the pressure control groove extending to a predetermined depth in the channel to allow gas to escape from the vessel until the plunger reaches the predetermined depth.

44. The apparatus of claim 43, wherein the plunger has a pressure stroke sufficient to increase the pressure in the chamber to at least 2 psi above the ambient pressure external to the vessel.

45. The apparatus of claim 27, wherein a rigid frame defines side walls of the chamber, and wherein:
   a) at least two of the side walls of the chamber are optically transmissive and angularly offset from each other;
   b) the apparatus further comprises an optics system having at least one light source for exciting the mixture through a first one of the optically transmissive side walls and having at least one detector for detecting light emitted from the chamber through a second one of the optically transmissive side walls.

46. The apparatus of claim 45, wherein:
   a) the apparatus includes first and second thermal surfaces formed by opposing plates positioned to receive the chamber of the vessel between them; and
   b) each of the plates has first and second edges angularly offset from each other by substantially the same angle that the optically transmissive side walls are offset from each other, and the plates are positioned to receive the chamber between them such that the first optically transmissive side wall is positioned substantially adjacent and parallel to the first bottom edge of each plate and such that the second optically transmissive side wall is positioned substantially adjacent and parallel to the second bottom edge of each plate.

47. The apparatus of claim 45, wherein the optically transmissive side walls are angularly offset from each other by about 90°.

48. The apparatus of claim 45, wherein at least two additional side walls of the chamber have retro-reflective faces.

49. The apparatus of claim 45, wherein the ratio of the width of the chamber to the thickness of the chamber is at least 4:1, and wherein the chamber has a thickness in the range of 0.5 to 2.0 mm.

50. The apparatus of claim 39, wherein the heat-exchanging module further comprises a housing and a cooling element disposed within the housing for cooling the reaction mixture contained in the chamber.

51. The apparatus of claim 39, wherein the base instrument is constructed to receive and control a plurality of such heat-exchanging modules.

52. The apparatus of claim 51, further comprising at least one computer for controlling the base instrument.

* * * * *